US012708328B2

(12) United States Patent
Mills et al.

(10) Patent No.: US 12,708,328 B2
(45) Date of Patent: Aug. 18, 2026

(54) SYSTEM AND METHODS FOR MONITORING AND DISPLAY OF A HEMODYNAMIC STATUS OF A PATIENT

(71) Applicant: Masimo Corporation, Irvine, CA (US)

(72) Inventors: Eric Stephen Mills, Irvine, CA (US); Matthew Giovanni Sassone, Irvine, CA (US); Keith Ward Indorf, Lake Elsinore, CA (US); Sebastian T. Frey, Laguna Niguel, CA (US); Heyi Wang, Foothill Ranch, CA (US)

(73) Assignee: Masimo Corporation, Irvine, CA (US)

( * ) Notice: Subject to any disclaimer, the term of this patent is extended or adjusted under 35 U.S.C. 154(b) by 742 days.

(21) Appl. No.: 17/938,649

(22) Filed: Oct. 6, 2022

(65) Prior Publication Data

US 2023/0116371 A1 Apr. 13, 2023

Related U.S. Application Data

(60) Provisional application No. 63/253,486, filed on Oct. 7, 2021.

(51) Int. Cl.
*A61B 5/00* (2006.01)
*A61B 5/02* (2006.01)
(Continued)

(52) U.S. Cl.
CPC .............. *A61B 5/743* (2013.01); *A61B 5/002* (2013.01); *A61B 5/02028* (2013.01); (Continued)

(58) Field of Classification Search
None
See application file for complete search history.

(56) References Cited

U.S. PATENT DOCUMENTS 4,576,181 A 3/1986 Wallace
4,679,567 A 7/1987 Hanlon
(Continued)

OTHER PUBLICATIONS

US 2024/0016391 A1, 01/2024, Lapotko et al. (withdrawn)
(Continued)

*Primary Examiner* — Meredith Weare
(74) *Attorney, Agent, or Firm* — Knobbe, Martens, Olson & Bear, LLP

(57) ABSTRACT

Systems and methods for monitoring and display of a hemodynamic status of a patient. Hemodynamic status may be monitored using, for example, a transducer, an adapter and one or more monitor devices. The adapter may be in communication with the transducer and the one or more monitor devices. The adapter can be configured to receive and process data from the transducer such as unprocessed physiological data. The adapter can be configured to transmit data to the monitor device(s) such as processed and/or unprocessed physiological data. The adapter can be configured to generate, and transmit to the monitor devices(s), user interface data for rendering interactive graphical user interfaces to display information such as physiological information relating to a hemodynamic status of the patient. The adapter can be configured to receive and process, from the monitor device(s) user commands or instructions to control an operation of the system or its components.

22 Claims, 40 Drawing Sheets

(51) Int. Cl.
*A61B 5/021* (2006.01)
*A61B 5/024* (2006.01)
*A61B 5/029* (2006.01)

(52) U.S. Cl.
CPC .............. *A61B 5/021* (2013.01); *A61B 5/024* (2013.01); *A61B 5/029* (2013.01); *A61B 5/748* (2013.01)

(56) References Cited

U.S. PATENT DOCUMENTS 4,776,343 A 10/1988 Hubbard
4,960,128 A 10/1990 Gordon et al.
4,964,408 A 10/1990 Hink et al.
4,970,900 A 11/1990 Shepherd
4,974,593 A 12/1990 Ng
4,997,421 A 3/1991 Palsrok
5,161,764 A 11/1992 Roney
5,280,789 A 1/1994 Potts
5,319,355 A 6/1994 Russek
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
5,417,395 A 5/1995 Fowler
D359,546 S 6/1995 Savage et al.
5,431,170 A 7/1995 Mathews
5,436,499 A 7/1995 Namavar et al.
D361,840 S 8/1995 Savage et al.
D362,063 S 9/1995 Savage et al.
D363,120 S 10/1995 Savage et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,551,300 A 9/1996 Vurek
5,561,275 A 10/1996 Savage et al.
5,566,676 A 10/1996 Rosenfeldt
5,590,649 A 1/1997 Caro et al.
5,602,924 A 2/1997 Durand et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,769,083 A 6/1998 MacEachern
5,829,723 A 11/1998 Brunner
5,890,929 A 4/1999 Mills et al.
5,919,134 A 7/1999 Diab
5,944,677 A 8/1999 Richard
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,071,243 A 6/2000 MacEachern
6,115,673 A 9/2000 Malin et al.
6,117,086 A 9/2000 Shulze
6,124,597 A 9/2000 Shehada et al.
6,128,521 A 10/2000 Marro et al.
6,129,675 A 10/2000 Jay
6,139,503 A 10/2000 Muller
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,255,708 B1 7/2001 Sudharsanan et al.
6,280,381 B1 8/2001 Malin et al.
6,285,896 B1 9/2001 Tobler et al.
6,296,614 B1 10/2001 Pruter
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,606,511 B1 8/2003 Ali et al.
6,635,020 B2 10/2003 Tripp, Jr.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Al-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,920,345 B2 7/2005 Al-Ali et al.
6,934,570 B2 8/2005 Kiani et al.
6,943,348 B1 9/2005 Coffin IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,220,230 B2 * 5/2007 Roteliuk ................ A61B 5/029 600/485
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,284,729 B2 10/2007 Walsh

(56) References Cited

U.S. PATENT DOCUMENTS 7,284,730 B2 10/2007 Walsh
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Ai-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Ai-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,790,268 B2 7/2014 Ai-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,897,847 B2 11/2014 Al-Ali
8,911,377 B2 12/2014 Al-Ali
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,138,180 B1 9/2015 Coverston et al.
9,153,112 B1 10/2015 Kiani et al.
9,192,329 B2 11/2015 Al-Ali
9,192,351 B1 11/2015 Telfort et al.
9,195,385 B2 11/2015 Al-Ali et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,375,180 B2 6/2016 Russell
9,392,945 B2 7/2016 Al-Ali et al.
9,408,542 B1 8/2016 Kinast et al.

(56) References Cited

U.S. PATENT DOCUMENTS 9,436,645 B2 9/2016 Al-Ali et al.
9,445,759 B1 9/2016 Lamego et al.
9,474,474 B2 10/2016 Lamego et al.
9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,622,692 B2 4/2017 Lamego et al.
D788,312 S 5/2017 Al-Ali et al.
9,649,054 B2 5/2017 Lamego et al.
9,656,044 B2 5/2017 Nokes, Jr.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,749,232 B2 8/2017 Sampath et al.
9,750,442 B2 9/2017 Olsen
9,750,461 B1 9/2017 Telfort
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,936,917 B2 4/2018 Poeze et al.
9,955,937 B2 5/2018 Telfort
9,965,946 B2 5/2018 Al-Ali et al.
D820,865 S 6/2018 Muhsin et al.
9,986,952 B2 6/2018 Dalvi et al.
D822,215 S 7/2018 Al-Ali et al.
D822,216 S 7/2018 Barker et al.
10,010,276 B2 7/2018 Al-Ali et al.
10,029,085 B1 7/2018 Heyman
10,086,138 B1 10/2018 Novak, Jr.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
RE47,353 E 4/2019 Kiani et al.
10,279,247 B2 5/2019 Kiani
10,292,664 B2 5/2019 Ai-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Ai-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,567 B2 7/2022 O'Brien et al.
11,389,093 B2 7/2022 Triman et al.
11,406,286 B2 8/2022 Al-Ali et al.

(56) References Cited

U.S. PATENT DOCUMENTS 11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Ai-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.
12,478,272 B2 11/2025 Telfort et al.
12,478,293 B1 11/2025 Al-Ali et al.
12,495,967 B2 12/2025 Muhsin et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0124903 A1* 6/2005 Roteliuk ................ A61B 5/029 600/526
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2008/0255438 A1* 10/2008 Saidara .............. A61B 5/14532 600/365
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.

(56) References Cited

U.S. PATENT DOCUMENTS

2011/0118561 A1 5/2011 Tari et al.
2011/0137297 A1 6/2011 Kiani et al.
2011/0172498 A1 7/2011 Olsen et al.
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0060147 A1 3/2013 Welch et al.
2013/0096405 A1 4/2013 Garfio
2013/0296672 A1 11/2013 O'Neil et al.
2013/0345921 A1 12/2013 Al-Ali et al.
2014/0166076 A1 6/2014 Kiani et al.
2014/0180160 A1 6/2014 Brown et al.
2014/0187973 A1 7/2014 Brown et al.
2014/0275871 A1 9/2014 Lamego et al.
2014/0275872 A1 9/2014 Merritt et al.
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0073241 A1 3/2015 Lamego
2015/0080754 A1 3/2015 Purdon et al.
2015/0099950 A1 4/2015 Al-Ali et al.
2017/0024748 A1 1/2017 Haider
2017/0173632 A1 6/2017 Al-Ali
2017/0251974 A1 9/2017 Shreim et al.
2018/0228386 A1* 8/2018 McCall ................ A61B 5/0215
2018/0242926 A1 8/2018 Muhsin et al.
2018/0247712 A1 8/2018 Muhsin et al.
2019/0239787 A1 8/2019 Pauley et al.
2019/0320906 A1 10/2019 Olsen
2020/0060869 A1 2/2020 Telfort et al.
2020/0111552 A1 4/2020 Ahmed
2020/0113520 A1 4/2020 Abdul-Hafiz et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0329983 A1 10/2020 Al-Ali et al.
2020/0329984 A1 10/2020 Al-Ali et al.
2020/0329993 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.
2021/0256267 A1 8/2021 Ranasinghe et al.
2021/0256835 A1 8/2021 Ranasinghe et al.
2021/0259629 A1* 8/2021 Smith ................ A61B 5/02405
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Ai-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0151521 A1 5/2022 Krishnamani et al.
2022/0218244 A1 7/2022 Kiani et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Al-Ali
2023/0058342 A1 2/2023 Kiani
2023/0069789 A1 3/2023 Koo et al.
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Ai-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0255764 A1 8/2025 Stead
2025/0278512 A1 9/2025 Koo et al.
2025/0281059 A1 9/2025 Avendano
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.

OTHER PUBLICATIONS

"HemoSphere Advanced Monitor Operator's Manual." Edwards Lifesciences. Aug. 31, 2017. 238 pages. (Year: 2017).*

Letter from Bram D. Zuckerman to Masimo Corporation re 510(k) No. K023960, U.S. Food & Drug Administration, dated Jan. 9, 2003 in 3 pages.

Letter from Bram D. Zuckerman to Masimo Corporation re 510(k) No. K122247, U.S. Food & Drug Administration, dated Mar. 20, 2013 in 3 pages.

Letter from Owen P. Faris to Masimo Corporation re 510(k) No. K131048, U.S. Food & Drug Administration, dated Aug. 28, 2013 in 3 pages.

Letter from Bram D. Zuckerman to Masimo Corporation re 510(k) No. K152935, U.S. Food & Drug Administration, dated Mar. 17, 2016 in 3 pages.

(56) References Cited

OTHER PUBLICATIONS

Letter from Bram D. Zuckerman to Masimo Corporation re 510(k) No. K163334, U.S. Food & Drug Administration, dated Jun. 5, 2017 in 4 pages.

Letter from T.K. O'Brien to Masimo Corporation re 510(k) No. K962918, U.S. Food & Drug Administration, dated Jan. 8, 1999 in 9 pages.

* cited by examiner

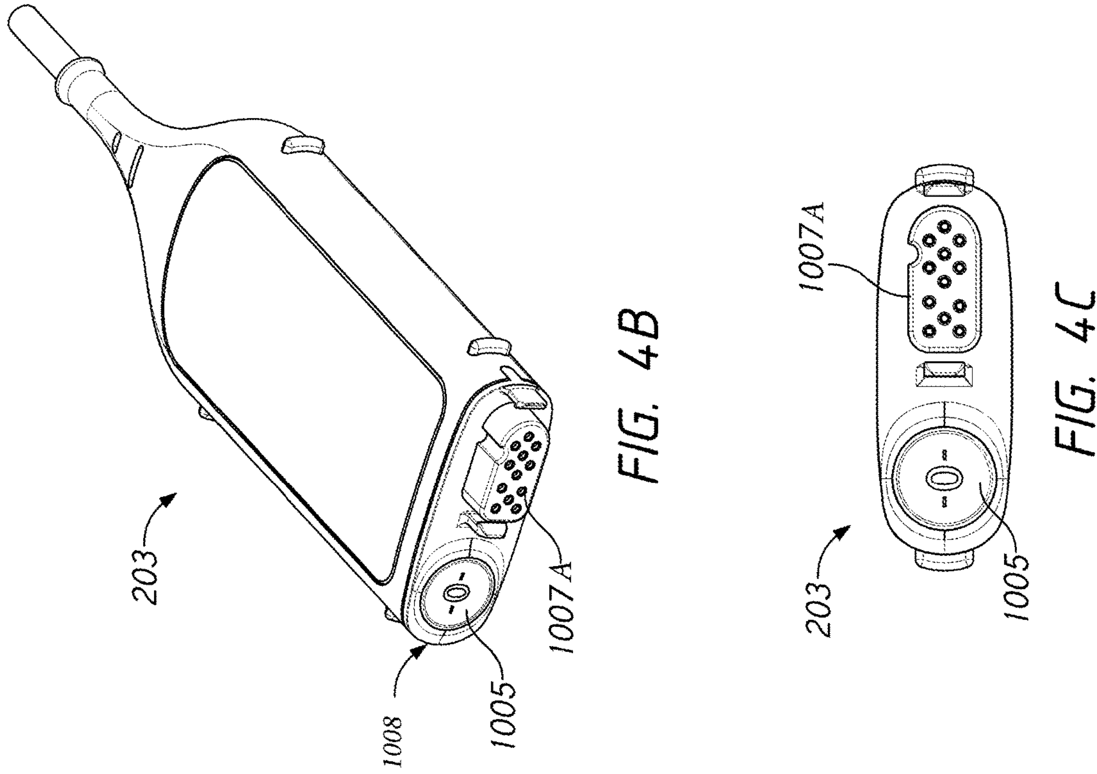
FIG. 4B
FIG. 4C
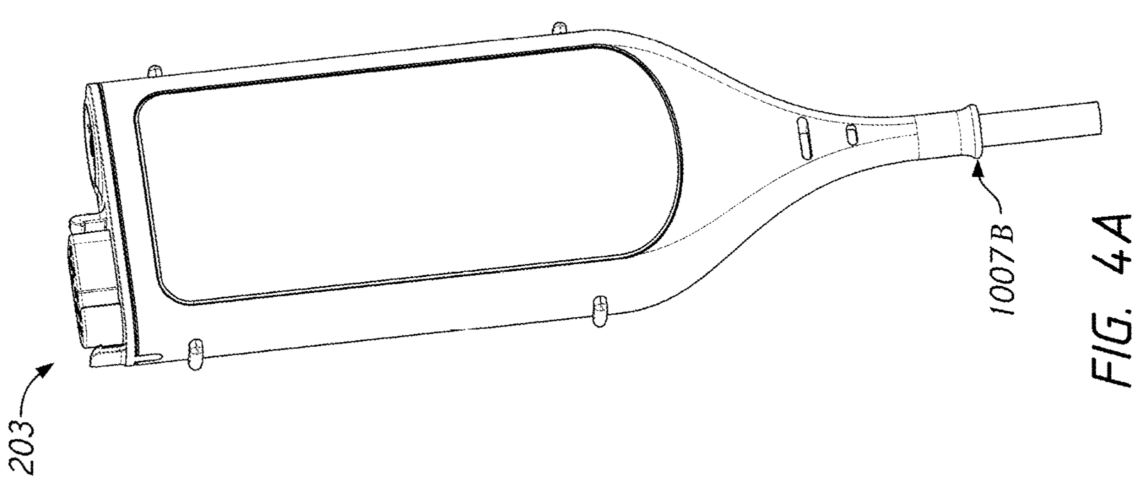
FIG. 4A 1019
1003

| | Baseline | Current | Nadir | Δ(%) |
|---|---|---|---|---|
| SV | 50 | 50 | 50 | -0% |

×
Tidal Volume Challenge
Prep 〉Start 〉Results
Tidal Volume challenge is a transient increase in Vt from 6ml/Kg PBW to 8ml/kg PBW to observe changes in SVV or PPV that may indicate fluid responsiveness.
Gender
female
Predicated body weight
70kg
auto predict weight
ON
Vt at 6ml/Kg PBW
420
Vt at 8ml/Kg PBW
560
Next
901

SYSTEM AND METHODS FOR MONITORING AND DISPLAY OF A HEMODYNAMIC STATUS OF A PATIENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application claims priority to U.S. Provisional Application No. 63/253,486, titled SYSTEM AND DEVICES FOR MONITORING A HEMODYNAMIC STATUS OF A PATIENT and filed on Oct. 7, 2021, the entire content of which is incorporated by reference herein in its entirety and for all purposes and forms a part of this specification.

FIELD

The present disclosure relates to devices, methods, and/or systems for monitoring a patient's hemodynamic status and/or cardiac output.

BACKGROUND

An accurate knowledge of the hemodynamic status/cardiac output of the heart of a patient helps medical practitioners assess a patient's medical condition. The constituents of cardiac output (measured, for example, in liters/minute), heart rate (measured, for example in beats per minute) and stroke volume (measured for example in mls) may also provide useful information. The stroke volume, or cardiac stroke volume, is the volume of blood ejected by the left ventricle during systole across the aortic valve forwards into the aorta during each cardiac contraction. This volume normally corresponds to the volume of blood in the left ventricle at the end of the systole minus the pre-systole diastolic volume of the left ventricle. This is particularly true in acute situations, such as, for example, for patients in intensive care units or patients undergoing an operation where for example it is used in fluid and drug management during anesthesia and after. Knowledge of a patient's cardiac output, or its constituents, may, moreover, be beneficial in less critical or less life threatening situations, such as in situations where the monitoring of the patient is generally desirable.

SUMMARY

For purposes of summarizing the disclosure, certain aspects, advantages, and novel features are discussed herein. It is to be understood that not necessarily all such aspects, advantages, or features will be embodied in any particular embodiment of the disclosure, and an artisan would recognize from the disclosure herein a myriad of combinations of such aspects, advantages, or features.

The present disclosure provides a system for monitoring a hemodynamic status of a patient. The system may comprise: a transducer configured to couple to the patient and measure a hemodynamic status of the patient; a monitor comprising a display and configured to display graphical user interfaces via the display and receive user input via the display; and an adapter in communication with the transducer and the display and comprising one or more hardware processors. The one or more hardware processors of the adapter may be configured to: generate one or more signals in response to the measurement of the transducer; process the one or more signals to generate one or more physiological parameters; generate, based at least in part on the one or more signals or the one or more physiological parameters, user interface data for rendering a graphical user interface; transmit, to the monitor, the user interface data; transmit, to the monitor, the one or more signals or the one or more physiological parameters; receive, from the monitor, user input; and execute instructions to control an operation of the adapter or transducer or monitor, according to the user input.

In some implementations, the hemodynamic status may comprise a cardiac output of the patient.

In some implementations, the transducer uses a lithium chloride indicator method to measure the hemodynamic status of the patient.

In some implementations, the one or more hardware processors may be configured to not transmit, to the monitor, the one or more signals, and to transmit, to the monitor, the one or more physiological parameters.

In some aspects, the techniques described herein relate to a system for monitoring a hemodynamic status of a patient, the system including: a transducer configured to couple to the patient and measure a hemodynamic status of the patient; a monitor including a display and configured to display graphical user interfaces via the display and receive user input via the display; and an adapter in communication with the transducer and the display and including one or more hardware processors, wherein the one or more hardware processors are configured to: generate one or more signals in response to the measurement of the transducer; process the one or more signals to generate one or more physiological parameters; generate, based at least in part on the one or more signals or the one or more physiological parameters, user interface data for rendering a graphical user interface without additional signal processing by the monitor; transmit, to the monitor, the user interface data; transmit, to the monitor, the one or more signals or the one or more physiological parameters; receive, from the monitor, user input; and execute instructions to control an operation of the adapter or transducer or monitor, according to the user input.

In some aspects, the techniques described herein relate to a system, wherein the hemodynamic status includes a cardiac output of the patient.

In some aspects, the techniques described herein relate to a system, wherein the transducer uses a lithium chloride indicator method to measure the hemodynamic status of the patient.

In some aspects, the techniques described herein relate to a system, wherein the one or more hardware processors are configured to not transmit, to the monitor, the one or more signals, and to transmit, to the monitor, the one or more physiological parameters.

In some aspects, the techniques described herein relate to a system, wherein the adapter includes a button configured to cause the one or more hardware processors to alter a value of the one or more physiological parameters to an altered value.

In some aspects, the techniques described herein relate to a system, wherein the altered value includes a default value or zero value.

In some aspects, the techniques described herein relate to a system, wherein the adapter is configured to couple to a medical IV pole.

In some aspects, the techniques described herein relate to a system wherein the adapter is configured to couple to the medical IV pole through a clip connector.

In some aspects, the techniques described herein relate to a system, wherein the clip connector includes a spring loaded clip configured to engage the medical IV pole.

In some aspects, the techniques described herein relate to a system wherein the clip connector is configured to removably receive the adapter.

In some aspects, the techniques described herein relate to a system wherein the clip connector includes a material configured to improve engagement of the connector clip with the medical IV pole and reduce movement of the connector clip with respect to a position of the connector clip on the medical IV pole.

In some aspects, the techniques described herein relate to a system wherein the clip connector includes a material configured to improve engagement of the connector clip with the adapter and reduce movement of the adapter with respect to the connector clip.

In some aspects, the techniques described herein relate to a system for monitoring a hemodynamic status of a patient, the system including: a transducer configured to couple to the patient and measure a hemodynamic status of the patient; a holder configured to couple the transducer to a mounting plate including a first bracket arm and a second bracket arm, wherein the first bracket is separated from the second bracket by a width, wherein the holder includes a first flexible arm configured to engage the first bracket arm and a second flexible arm configured to engage the second bracket arm of the mounting plate, In some aspects, the techniques described herein relate to wherein the holder is configured to secure to a plurality 13, wherein the first or second flexible arm includes a partially cut out portion of the holder configured to couple the transducer to the mounting plate.

In some aspects, the techniques described herein relate to a system wherein the first or second flexible arm is configured to be depressed inwards towards a central axis of the transducer.

In some aspects, the techniques described herein relate to a system wherein the first or second flexible arm is configured to provide an outward force towards the at least one bracket when depressed inwards.

In some aspects, the techniques described herein relate to a system wherein the first or second flexible arm are integrated into the holder.

In some aspects, the techniques described herein relate to a system, wherein the first or second flexible arm are cutout of a portion of the holder.

In some aspects, the techniques described herein relate to a system wherein the holder is configured to secure to a plurality of mounting plates with varying depths of bracket arms.

In some aspects, the techniques described herein relate to a system, wherein the transducer is configured to communicate with a patient monitor through an adapter.

In some aspects, the techniques described herein relate to a system, wherein the width includes a distance between 26 and 30 mm.

In some aspects, the techniques described herein relate to a system for displaying a physiological status of a patient, the system including: a monitor including a display and configured to display graphical user interfaces via the display and receive user input via the display; and one or more hardware processors in communication with the display, the one or more hardware processors configured to: generate one or more signals in response to a measurement of a physiological sensor; process the one or more signals to generate one or more physiological parameters; generate, based at least in part on the one or more signals or the one or more physiological parameters, user interface data for rendering a graphical user interface, wherein the graphical user interface includes: at least one first radial dial gauge associated with a first physiological parameter derived from a second parameter of the one or more physiological parameters; at least one second radial dial gauge displayed on a level below the first radial gauge, the second radial gauge associated with the second physiological parameter having an influencing relationship with the first physiological parameter; a branch displayed between the at least one first radial gauge and the at least on second radial gauge, the branch indicating a influencing relationship between the first parameter and the second parameter, the branch being displayed differently based on one or more values or trends of at least the first physiological parameter or the second physiological parameter; and cause to display on the monitor, the user interface data.

In some aspects, the techniques described herein relate to a system, wherein the physiological sensor includes a transducer.

In some aspects, the techniques described herein relate to a system, wherein the branch is emphasized based on an abnormal value of the second physiological parameter and the first physiological parameter.

In some aspects, the techniques described herein relate to a system, wherein an emphasis of the branch includes a highlighting or coloring of the branch a different color than a default color.

In some aspects, the techniques described herein relate to a system wherein the branch is emphasized based on an abnormal trend of the second physiological parameter or first physiological parameter.

In some aspects, the techniques described herein relate to a system wherein the at least one first radial gauge includes at least one radial gauge segment, wherein each segment is associated with a range of physiological parameter values.

In some aspects, the techniques described herein relate to a system, wherein a first range associated with a first segment includes a normal range and a second range associated with a second segment includes an abnormal range.

In some aspects, the techniques described herein relate to a system, wherein the at least one radial gauge includes a dial configured to indicate a current value of the first physiological parameter.

In some aspects, the techniques described herein relate to a system, wherein the at least one first physiological parameter includes a blood pressure parameter and wherein the second physiological parameter includes CI or SVRI.

In some aspects, the techniques described herein relate to a system, wherein the first physiological parameter includes CI and wherein the second physiological parameter includes SVI or HR.

In some aspects, the techniques described herein relate to a system, wherein first physiological parameter includes SVI and the second physiological parameter includes PPV.

In some aspects, the techniques described herein relate to a system, wherein the at least one first radial gauge includes at least one textual and graphical representation of a value the first physiological parameter.

In some aspects, the techniques described herein relate to a system, wherein the at least one first radial gauge includes a graphical indication of a trend associated with the first physiological parameter.

In some aspects, the techniques described herein relate to a system, wherein the first physiological parameter is based on a function of at least the second physiological parameter.

In some aspects, the techniques described herein relate to a system, wherein the first physiological parameter is based on a function of the second physiological parameters and a third physiological parameter.

In some aspects, the techniques described herein relate to a system, wherein the second physiological is a function of the third physiological parameter.

In some aspects, the techniques described herein relate to a system for displaying a physiological status of a patient, the system including: a monitor including a display and configured to display graphical user interfaces via the display and receive user input via the display; and one or more hardware processors in communication with the display, the one or more hardware processors configured to: generate one or more signals in response to a measurement of a physiological sensor; process the one or more signals to generate one or more physiological parameters; generate, based at least in part on the one or more signals or the one or more physiological parameters, user interface data for rendering a graphical user interface, wherein the graphical user interface includes: a tree diagram of graphical representations of a plurality of physiological parameters, wherein a location of a graphical representation of a physiological parameter of the plurality of physiological parameters is associated with an influencing relationship of the physiological parameter with a primary physiological parameter; and cause to display on the monitor, the user interface data.

In some aspects, the techniques described herein relate to a system, wherein branches of the tree diagram are highlighted based on a current value or trend of at least one physiological parameter of the plurality of physiological parameters.

In some aspects, the techniques described herein relate to a system, wherein a branch between a primary parameter of the plurality of physiological parameters and an influencing parameter of the plurality of physiological parameters is highlighted if the current value of at primary parameter and the influencing parameter are outside respective normal ranges.

In some aspects, the techniques described herein relate to a system, wherein the primary parameter includes a blood pressure parameter and the influencing parameter includes CL CI or SVRI.

In some aspects, the techniques described herein relate to a system, wherein the primary parameter includes CI and wherein the influencing parameter includes SVI or HR.

In some aspects, the techniques described herein relate to a system, wherein the primary parameter includes SVI and the influencing parameter includes PPV.

In some aspects, the techniques described herein relate to a system, wherein at least one graphical representation of a physiological parameter includes a radial gauge.

Any of the aspects or examples disclosed herein may be combined in whole or in part.

BRIEF DESCRIPTION OF THE DRAWINGS

Certain features of this disclosure are described below with reference to the drawings. The illustrated embodiments are intended to illustrate, but not to limit, the embodiments. Various features of the different disclosed embodiments can be combined to form further embodiments, which are part of this disclosure.

FIGS. 4A-4C illustrate example views of the example connector illustrated in FIGS. 3A-3B.

FIGS. 8A-8L, 9A-9G, 10A-10D, 11A-11D, 12A-12C, 13A-13F illustrate example user interfaces that may be displayed by a monitor device of the system described herein.

DETAILED DESCRIPTION

Figure 1:
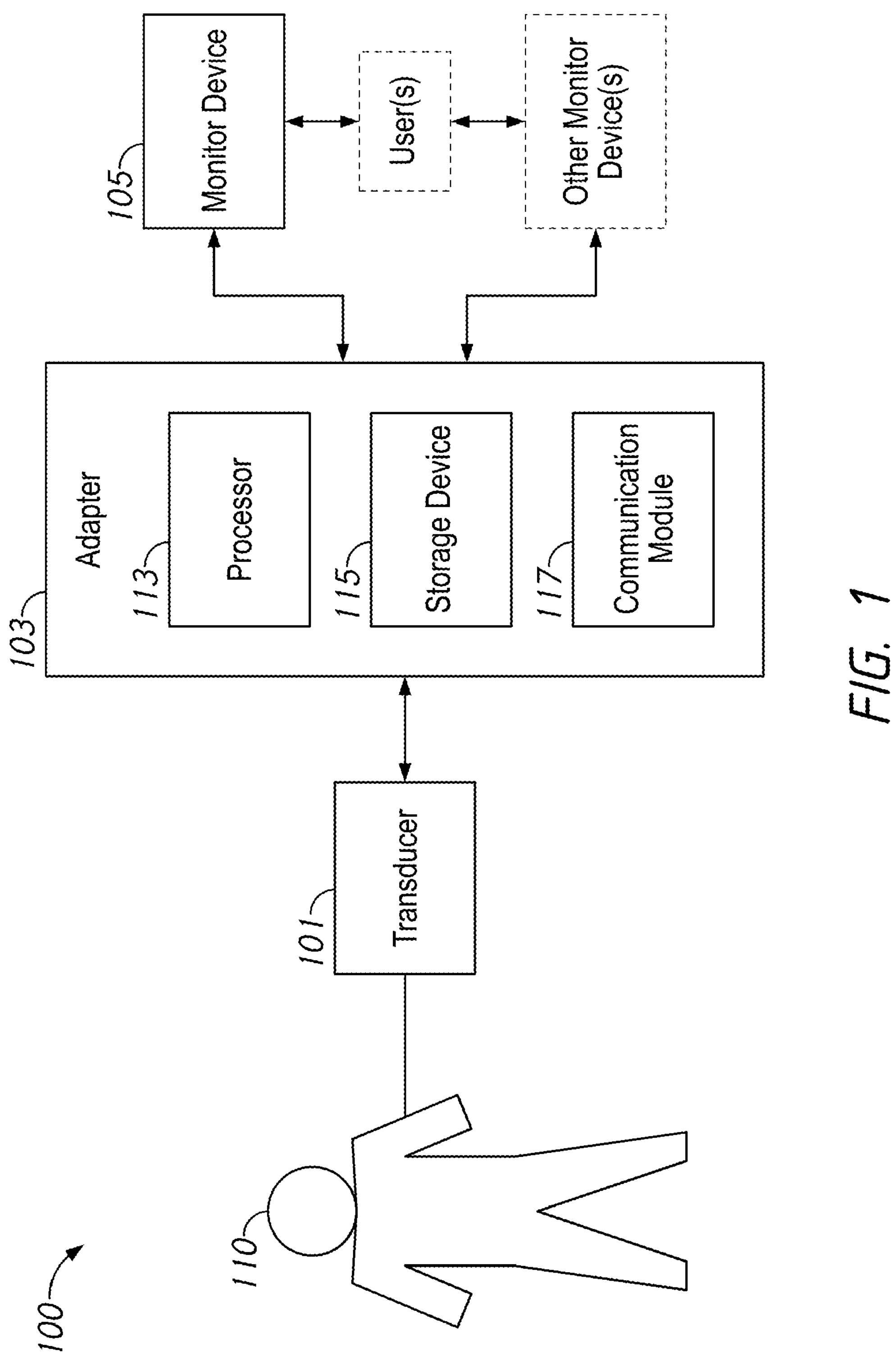
FIG. 1 is a schematic block diagram illustrating an example system and devices for monitoring a patient's hemodynamic status.

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

Example Overview of Systems and Devices

FIG. 1 is a schematic block diagram illustrating an example system 100 and devices for monitoring a patient's hemodynamic status. The system 100 can include a transducer 101, an adapter 103, and one or more monitoring devices 105. The transducer 101 may be configured to monitor a hemodynamic status of the patient 110 such as cardiac output. The transducer 101 may be configured to connect to a patient 110. For example, the transducer 101 may be coupled to tubing, catheter, cannula, or the like coupled to a patient. The transducer 101 may be in wired or wireless communication with the adapter 103. The adapter 103 may be in wired or wireless communication with the one or more monitor devices 105.

The system 100 may include a transducer 101 which may be configured to detect a hemodynamic status of the patient and, in response, generate one or more signals. The transducer 101 may be configured to generate one or more signals indicating a patient's hemodynamic status. The transducer 101 may generate and/or transmit the one or more signals indicating the patient's hemodynamic status continuously, discretely in real-time, or on a delay with the patient's actual hemodynamic status. The transducer 101 may be configured to implement one or more methods to measure a hemodynamic status. In some examples, a transducer 101 may be configured to implement a bolus indicator dilution method and/or a lithium chloride indicator dilution method to measure hemodynamic status. The transducer 101 may additionally or alternatively be configured to measure physiological parameters, such as cardiac output.

In an example method, transducer 101 may be configured to inject or cause to inject, via a central or peripheral venous cannula, a bolus of lithium chloride to the patient 110. The transducer 101 may be configured to measure a resulting arterial lithium concentration time curve of the patient, for example, by withdrawing past a lithium sensor which may be attached to the patient's existing arterial line. In response, the transducer 101 may be configured to generate one or more signals indicating the hemodynamic status of the patient 110.

The system 100 may include an adapter 103. The adapter 103 can include at least one hardware processor 113, a storage device 115, a communication module 117. The processor(s) 113 can be configured, among other things, to process data, execute instructions to perform one or more functions, and/or control the operation of the transducer 101 and/or monitor devices 105. For example, the processor(s) 113 can be configured to process physiological data obtained from the transducer 101 and/or other physiological sensors or sources of measured and/or stored physiological data. Advantageously, the processor(s) 113 may be configured to independently perform one or more signal processing instructions without additional processing from a monitor and/or external processor(s). The processor(s) 113 may be configured to output physiological data for receipt by a variety of different types of monitors. Thus, the adapter 103 may be connected to a plurality of different types of monitors, thus simplifying use of the system described herein in a setting where different types of monitors or different manufacturer monitors may be in use. Similarly, physiological data may be packaged so as to connect to a variety of types of monitors. The processor(s) 113 may be configured to generate and display, in some examples, aspects of a user interface, such as described herein. The processor(s) 113 can be configured to execute instructions to perform functions related to the physiological data. For example, the processor(s) 113 can be configured to execute instructions to perform functions related to storing and/or transmitting such physiological data, for example to the monitor device 105. In some further examples, the processor(s) 113 can be configured to execute instructions associated with one or more graphical user interfaces. For example, the processor(s) 113 can be configured to generate data for rendering graphical user interfaces, to transmit to the monitor device(s) 105 for the monitor device(s) 105, and/or to display graphical user interfaces that may be useful for monitoring a hemodynamic status of a patient. In some examples, the adapter 103 may be configured to analyze a plurality of physiological data, including but not limited to non-invasive and minimally invasive physiological sensors. Thus, the adapter may simplify a connection to a monitoring system of a number of physiological sensor types and reduce the need to have multiple sensors with multiple connection points to a patient monitor. In some examples, the processor(s) 113 may be included on board or internal to the adapter 103 and/or external to the adapter 103. For example, the adapter 103 may be connected wirelessly or via wires to an external processor 113 configured to perform some or all of the processing described herein.

The one or more storage devices 115 can include one or more memory devices that store data, including without limitation, dynamic and/or static random access memory (RAM), programmable read-only memory (PROM), erasable programmable read-only memory (EPROM), electrically erasable programmable read-only memory (EEPROM), and the like. Such stored data can, for example, include processed and/or unprocessed physiological data obtained from the transducer 101.

The communication module 117 can facilitate communication (via wired and/or wireless connection) between the adapter 103 (and/or components thereof) and separate devices, such as the transducer 101 and/or monitoring device(s) 105. For example, the communication module 117 can be configured to allow the adapter 103 to wirelessly, and/or via a wired connection, communicate with other devices, systems, and/or networks over any of a variety of communication protocols. The communication module 117 can be configured to use any of a variety of wired or wireless communication protocols, such as Wi-Fi (802.11x), Bluetooth®, ZigBee®, Z-wave, cellular telephony, infrared, near-field communications (NFC), RFID, satellite transmission, proprietary protocols, combinations of the same, and the like. The communication module 117 can allow data and/or instructions to be transmitted and/or received to and/or from the adapter 103 and separate devices such as the transducer 101 and/or monitoring device(s) 105. The communication module 117 can be configured to transmit (for example, wirelessly) processed physiological data (such as physiological parameters) and/or unprocessed physiological data (such as raw signals) or other information to the monitor device(s) 105 or to separate computing devices, which can include, among others, a mobile device (for example, an iOS or Android enabled smartphone, tablet, laptop), a desktop computer, a server or other computing or processing device for display and/or further processing, among other things. As another example, the communication module 117 of the adapter 103 can be configured to wirelessly transmit processed and/or unprocessed obtained physiological information and/or other information (for example, motion and/or location data) to a mobile phone which can include one or more hardware processors configured to execute an application that generates a graphical user interface displaying information representative of the processed or unprocessed physiological and/or other information obtained from the adapter 103. The communication module 117 can be embodied in one or more components that are in communication with each other. The communication module 117 can include a wireless transceiver, an antenna, and/or a near field communication (NFC) component, for example, NFC transponder.

The system 100 may include one or more monitor devices 105. A monitor device 105 may be a physiological monitor device for monitoring a patient and/or a patient's physiological data or parameters. A monitor device 105 may include a display configured to display interactive graphical user interfaces. A monitor device 105 may receive processed and/or unprocessed physiological data or other information from the adapter 103 (for example, via the communication module). The monitor device 105 may additionally or alternatively receive user interface data for rendering a graphical user interface from the adapter 103. A monitor device 105 may generate interactive user interfaces. The interactive user interface(s) may be generated according to the data or information received from the adapter 103, for displaying on a display of the monitor device 105.

The monitor device(s) 105 may be native to the system 100 and/or may be natively compatible with the adapter 103 for example the monitor device 105 and the adapter 103 may be manufactured by the same manufacturer and/or include the same operational settings, parameters, specifications etc. In some embodiments, the monitor device(s) 105 may not be native to the system 105, for example, the monitor device 105 and adapter 103 may be manufactured by different manufacturers and/or include different operational settings and/or parameters. In some embodiments, the communication module 117 may be configured to communicate with non-native (e.g., third party monitor devices) to allow the system 100 to operate and function as if the monitor devices were native and as described herein.

In some embodiments, a user may interact with the monitor device(s) 105, for example, via an interactive user interface on a display of the monitor device 105. A user may control, via the monitor device 105, the operation or functionality of the system 100 or its components and devices such as the transducer 101, the adapter 103, or the monitor device(s) 105. As discussed above, the adapter 103 may be configured to receive user commands or instructions (e.g., via the communication module 117) and may process said user commands or instructions (e.g., by the processor 113) and may accordingly execute instructions to perform one or more functions, and/or control the operation of the transducer 101 and/or monitor devices 105.

Figure 2:
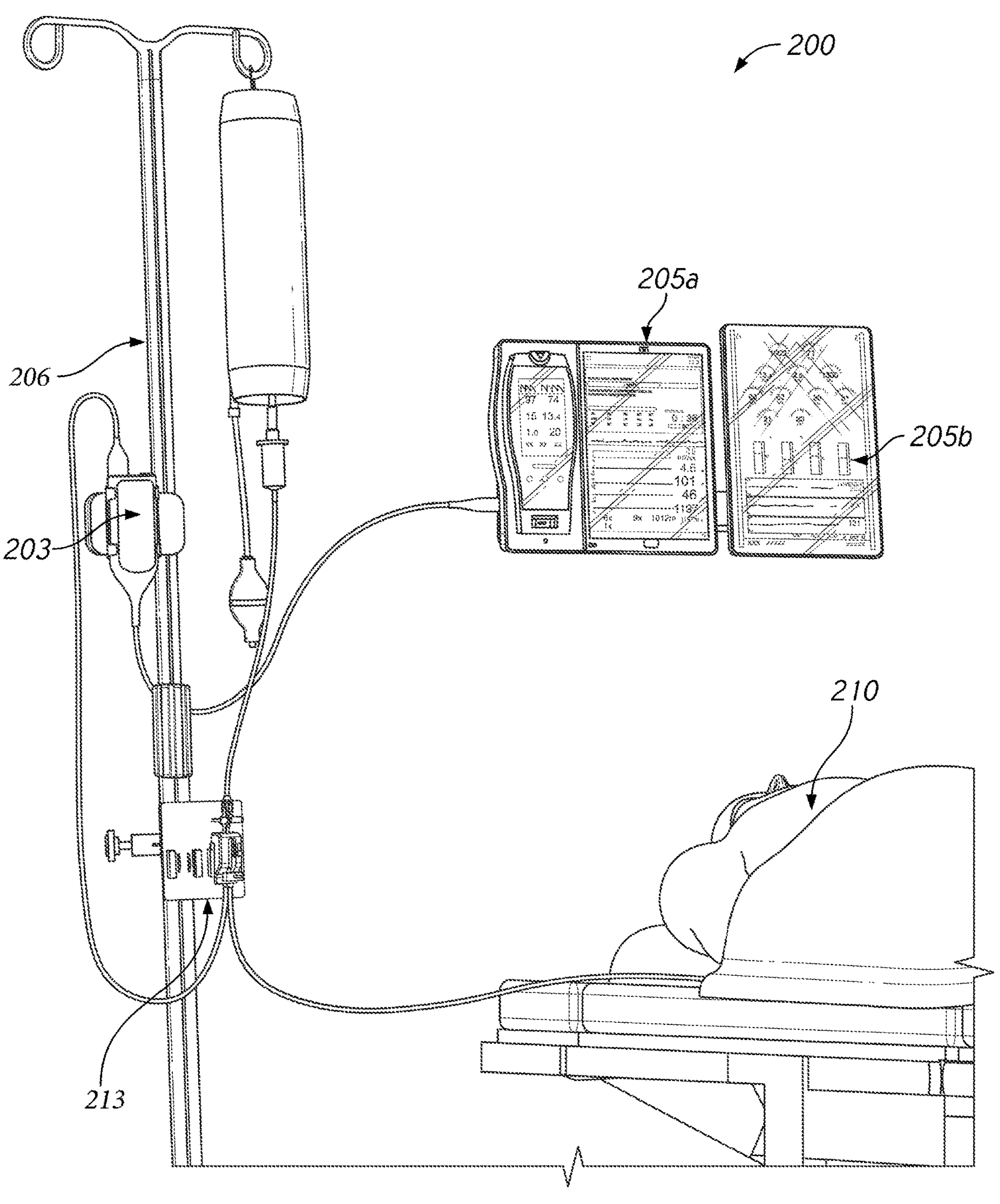
FIG. 2 illustrates an example implementation of a system and devices for monitoring a patient's hemodynamic status.

FIG. 2 illustrates an example implementation of a system 200 for monitoring a patient's hemodynamic status. The system 200 and its various devices and components may include similar structural and/or operational features as described with reference to FIG. 1. The system 200 can include a transducer 213 coupled to a patient 210 and configured to detect a patient's hemodynamic status. The system 200 can also include an adapter 203 configured to be in communication with the transducer 213 as well as one or more monitor devices 205*a*, 205*b* configured to be in communication with the adapter 203. The components may operate as discussed above with reference to FIG. 1.

FIGS. 3A-3B, 4A-4C, and 5A-5D illustrates aspects of an example adapter and adaptor connector or holder that may be part of a system 100 as described in FIG. 1 and/or system 200 as described in FIG. 2.

Figure 3B:
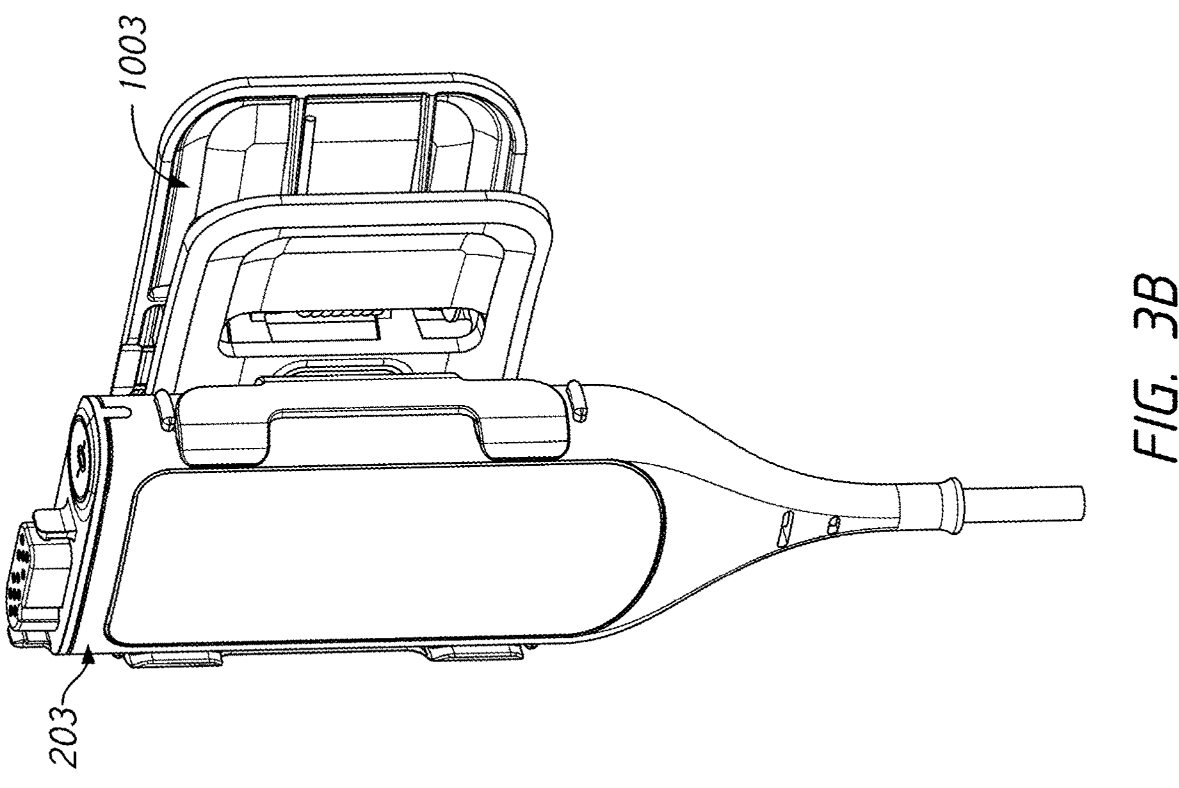
FIG. 3A-3B illustrate example views of a connector and clip system of the example system of FIGS. 1 and/or 2.
Figure 3A:
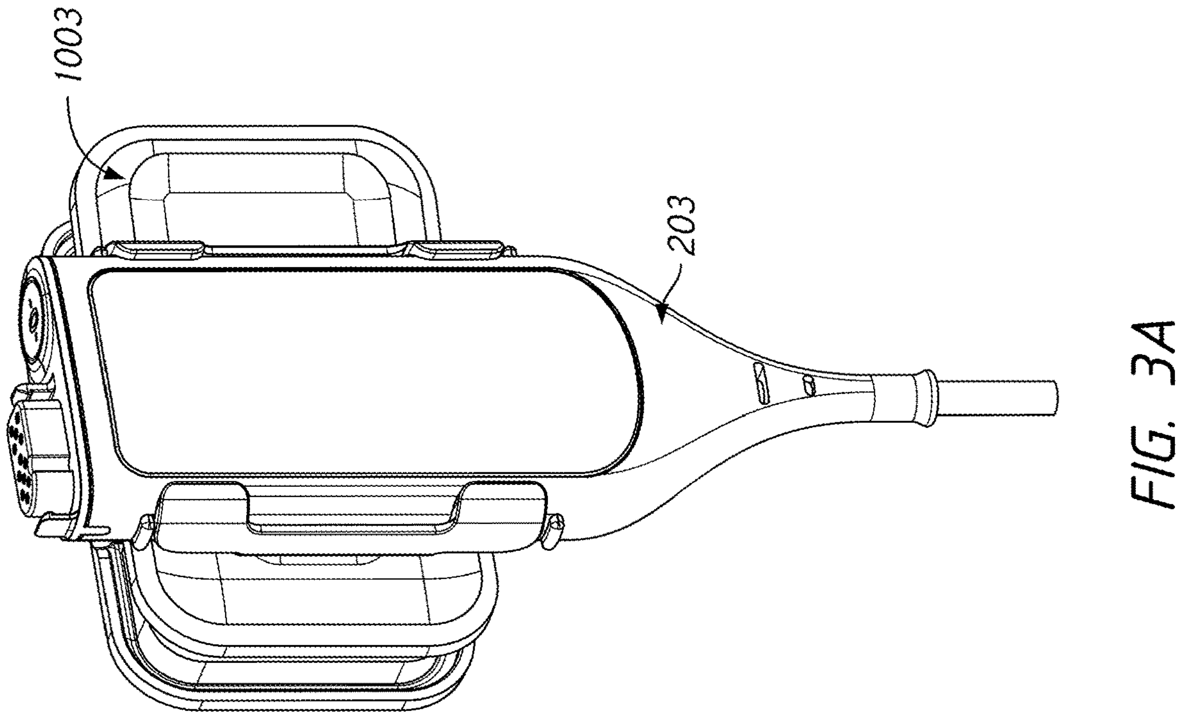
Figure 5B:
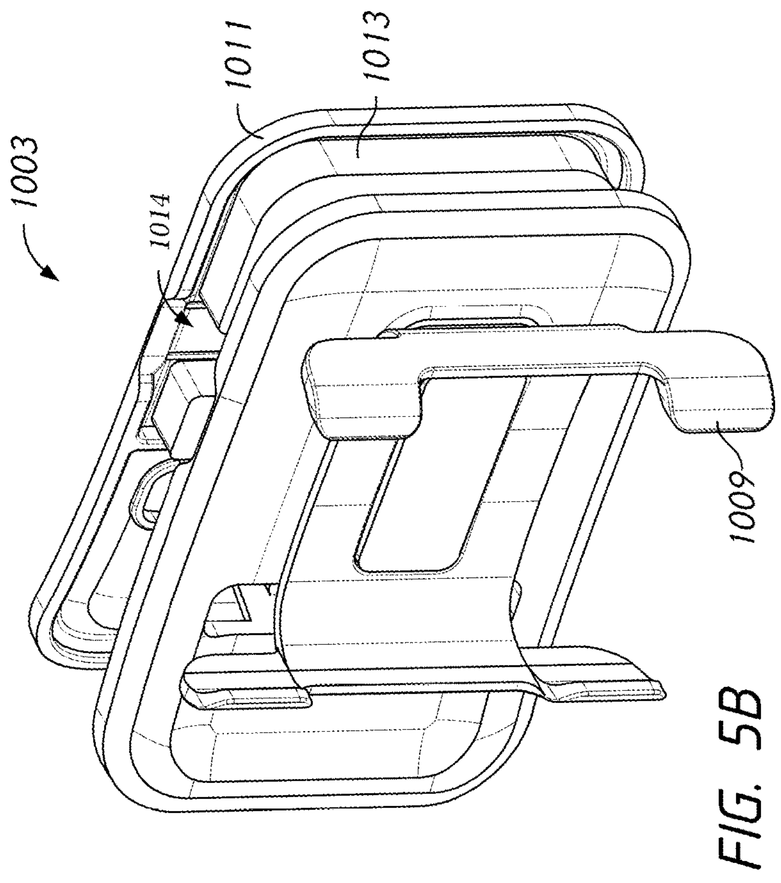
FIGS. 5A-5D illustrate example views of the example clip of FIGS. 3A-3B.
Figure 5A:
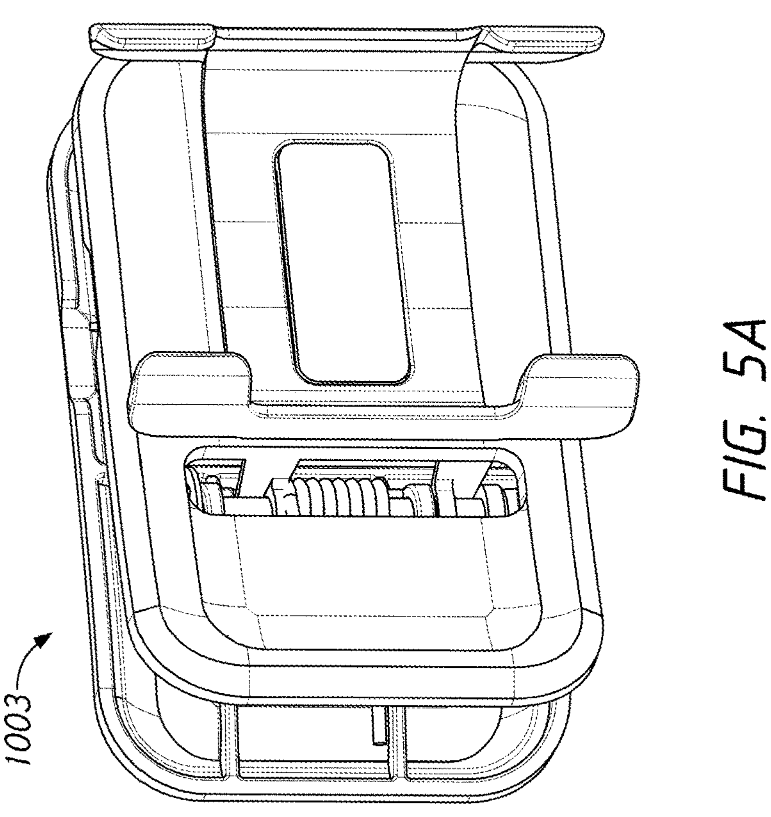
Figure 5D:
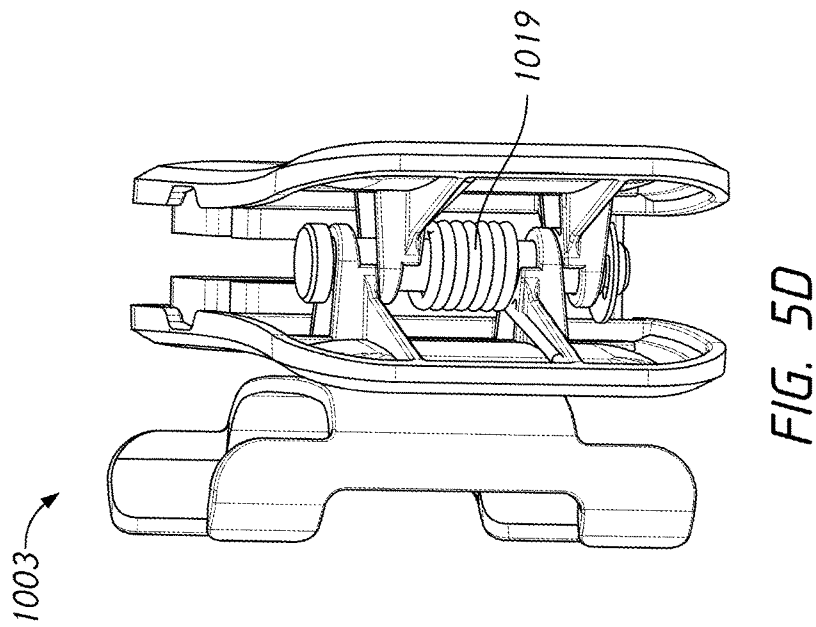
Figure 5C:
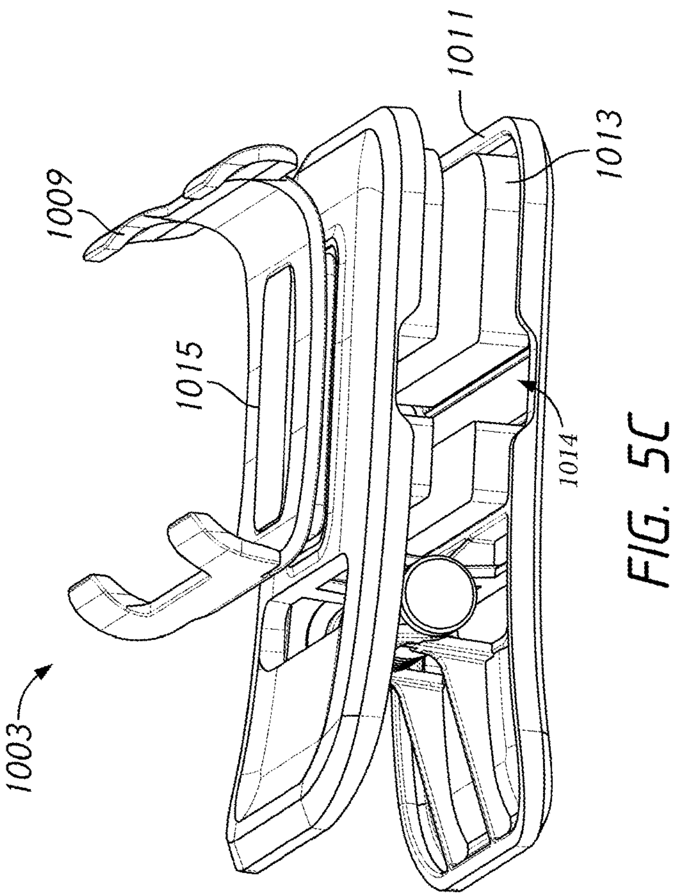
Figure 5E:
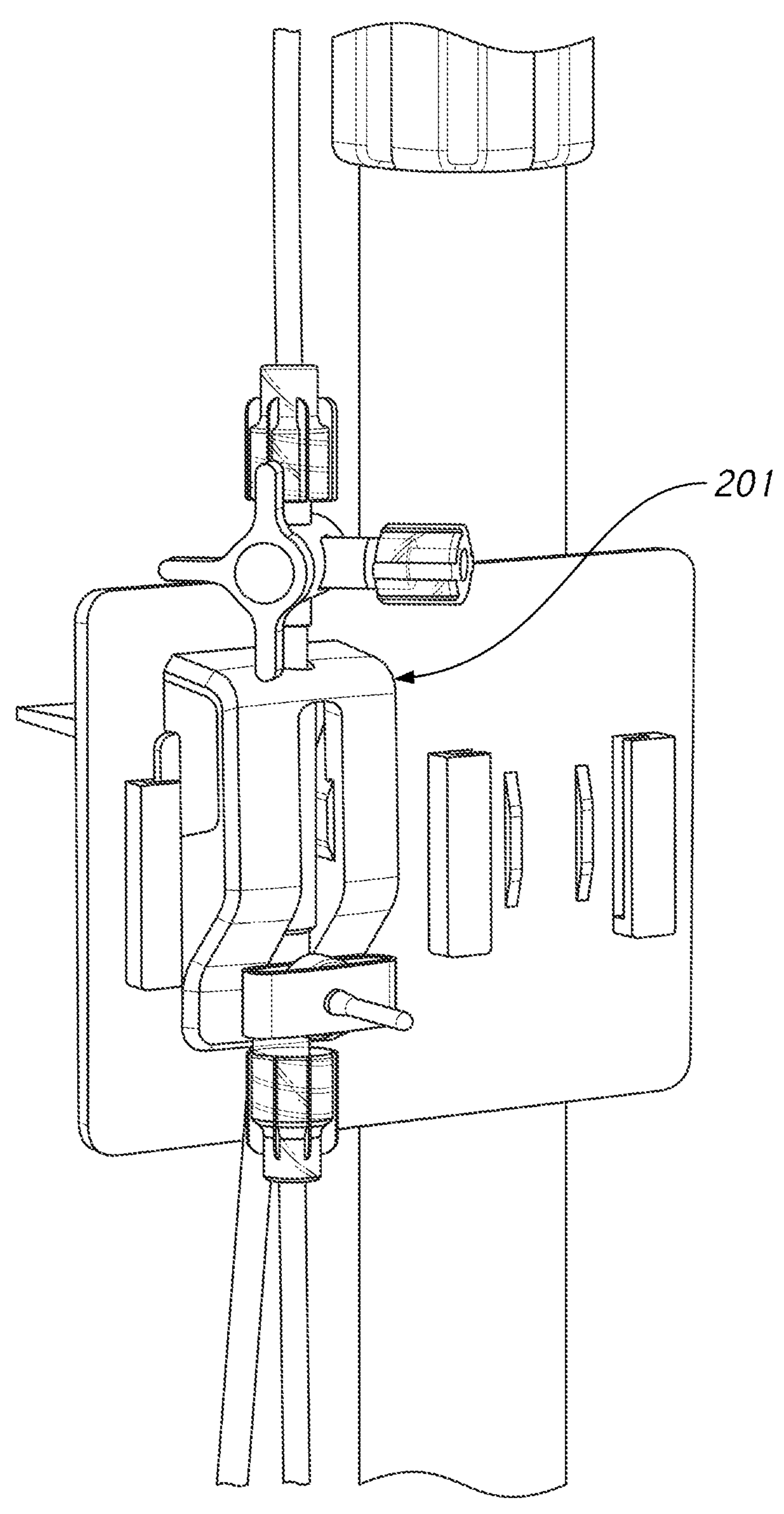
FIGS. 5E, 6A-6D and 7A-7C illustrate aspects of an example transducer and transducer shroud as illustrated in FIGS. 1 and/or 2.

As illustrated in FIGS. 3A-3B, an adapter 203 may be configured to mount or couple to a location in a patient environment, such as a medical IV pole, such as shown in FIG. 2, directly or indirectly. The adapter 203 may be configured to couple to a holder 1003. The holder 1003 may be configured to couple to a location in the environment of the patient, such as, for example, a medical IV pole 206 or another location adjacent to the patient. The connector 203 may include one or more hardware processors configured to perform one or more processes associated with at least one physiological parameter. For example, the one or more hardware processors may be configured to process at least one physiological parameter measured by a transducer 213, such as the transducer 213 shown in FIG. 2.

With reference to FIGS. 4A-4C, an adapter 203 may be configured to be in electronic communication with the transducer 213 and/or a patient monitor. In some examples, the adapter 203 may include at least one wired connection and/or connector 1007 configured to facilitate communication with the transducer 213 and adapter 203. In some examples, the adapter 203 may additionally or alternatively include a wireless connection to the transducer 213 and/or patient monitor 205. In some examples, a wired connector 1007 may be a coupled or attached cable. The cable may be configured to connect to a transducer 213 and/or other medical device. Additionally, in some examples, the wired connector 1007 may be a connection port for coupling the adapter 203 to a cable or other connective component, such as a wired or wireless connection. A connection port may be configured to connect to a specific patient monitor and/or a variety of patient monitors. In the illustrated example, the connector 203 includes a first connector 1007*a* and a second connector 1007*b*. The first connector 1007*a* may be a connection port configured to couple to a cable. The first connector 1007*a* may be configured to couple to an output and/or input. In some examples, the first connector 1007*a* may couple to a patient monitor through a connection cable (not shown). The connection port 1007*a* may be proprietary or unique to the monitor and/or a universal connector and capable of connecting to a plurality of different types of outputs or inputs. In some examples, a connector 203 may include more than one connection port 1007*a*. A second connector 1007*b* may include a permanent or semi-permanent cable connection. For example, the cable may be configured to connect to a medical device, such as a transducer 213. In some examples, the connector 203 may include more than two connectors 1007.

With continued reference to FIGS. 4A-4C, in some examples, an adapter 203 may include a "zero" button 1005. The "zero" button 1005 may be configured to calibrate, reset, or otherwise manipulate actions of the transducer 213 or other physiological sensor and/or cause a controller to manipulate data associated with data from the transducer 213 or other physiological sensor. The "zero" button may be configured to be on a top surface 1008 of the adapter 203. A top surface 1008 may be a minor surface associated with a first connector 1007*a* or second connector 1007*b*. The location of the "zero" button may be ergonomically comfortable for a person to reach and use. The location of the "zero" button may be located so as to reduce potential accidental engagement from the user. For example, a minor surface of the connector 203 may be less accidentally engaged than the major surface and thus a press of the "zero" button on the minor surface may be more likely intentional than if the "zero" button were located on a major surface.

FIG. 5A-5D illustrate views of an example connector clip 1003. The connector clip 1003 is configured to couple a connector 203 to a location in the environment of the patient. The connector clip 1003 may be configured to have a connector coupling section 1009. The connector coupling section 1009 may be configured to receive and/or hold a connector 203. The connector coupling section 1009 may, for example, have a shape configured to conform to at least a portion of the connector 203 so that the connector 203 may fit within the shape. In some examples, the connector coupling section 1009 may function as a clip, snap, or other fastener configured to removably hold the connector 203 in place on the clip 1003. In some examples, the shape may be configured to hold the connector 203 with enough force so as to reduce or limit unintentional vertical and/or horizontal movement of the connector 203. In some examples, a connector clip 1003 may include a rubberized or other material 1015 configured to make contact with a connector 203 when coupled to a connector clip 1003. The material 1015 may be configured to facilitate a friction coupling of the connector clip 1003 and the connector 203. The material 1015 may be configured to reduce or limit unintentional vertical and/or horizontal movement of the connector 203 when coupled to the connector clip 1003.

The connector clip 1003 may be an alligator clip or other spring loaded clip. However, other coupling mechanisms to a location in the environment of the patient may additionally or alternatively be used, such as adhesive, clasp, magnetic connection, the like or a combination thereof. The clip may include one or more separate components 1011 configured to close based on a tension from a spring 1019 around a pivot point 1017. An interior portion of the components 1011 may include one or more surfaces 1013. In some examples, the one or more surfaces 1013 may be textured so as to increase a frictional force between the clip and a component placed between the components 1101 of the clip 1003, such as a medical IV pole. In some examples, the one or more surfaces 1013 may be padded and/or rubberized. In some examples, the one or more surfaces 1013 may be a plurality of surfaces 1013 on each of the one or more components 1011. For example, one or more of the components 1011 may have two or more surfaces 1013. The two or more surfaces 1013 may have a gap 1014 configured to allow for a medical IV pole to be received between the two or more surfaces 1013. In some examples, the one or more surfaces 1013 may be indented to receive a medical IV pole. In some examples, the one or more surfaces 1013 on one component 1011 may be approximately parallel in whole or in part with one or more surfaces 1013 on an opposing component 1011 of the alligator clip 1003.

Figure 6A:
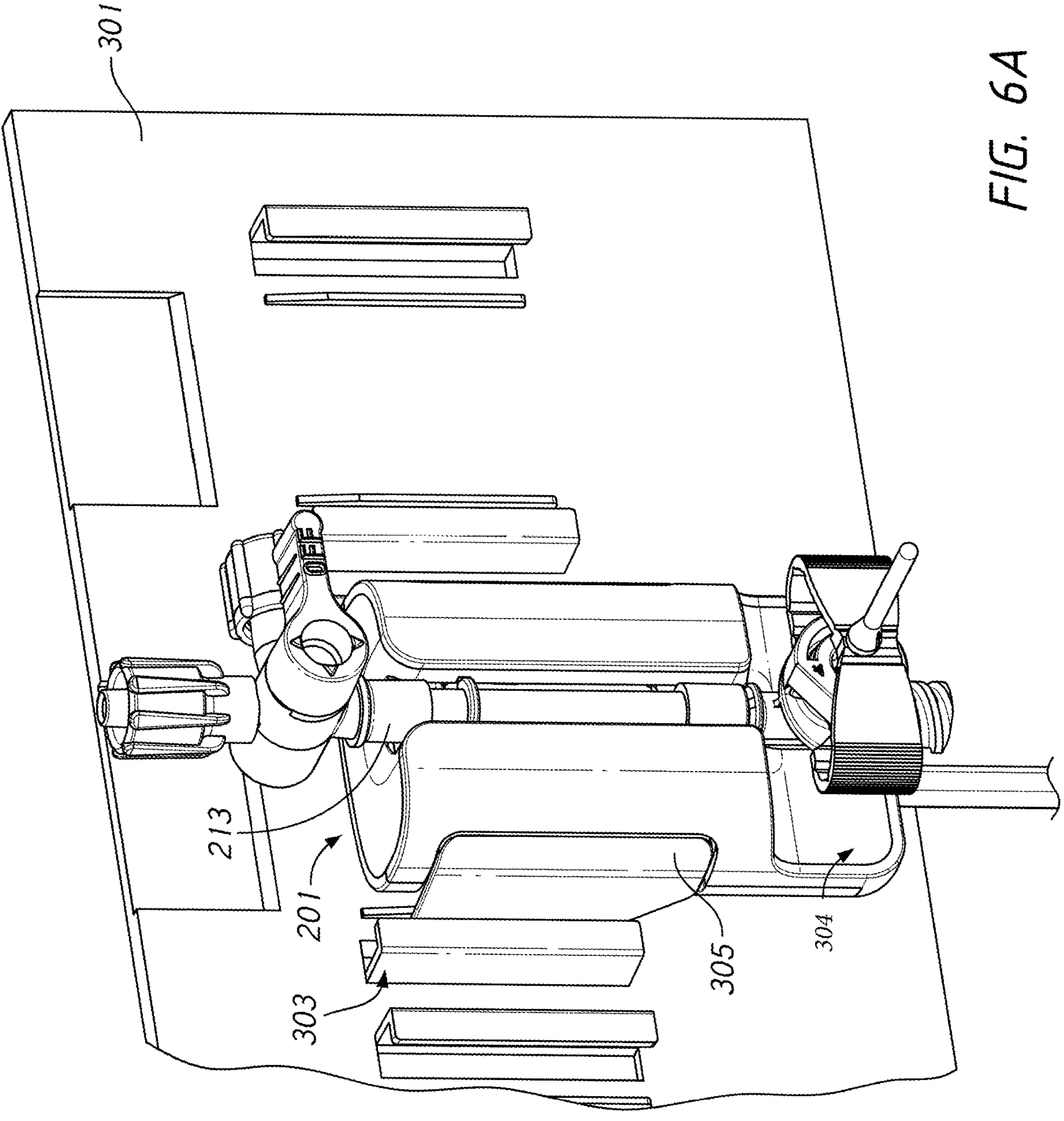
Figure 6C:
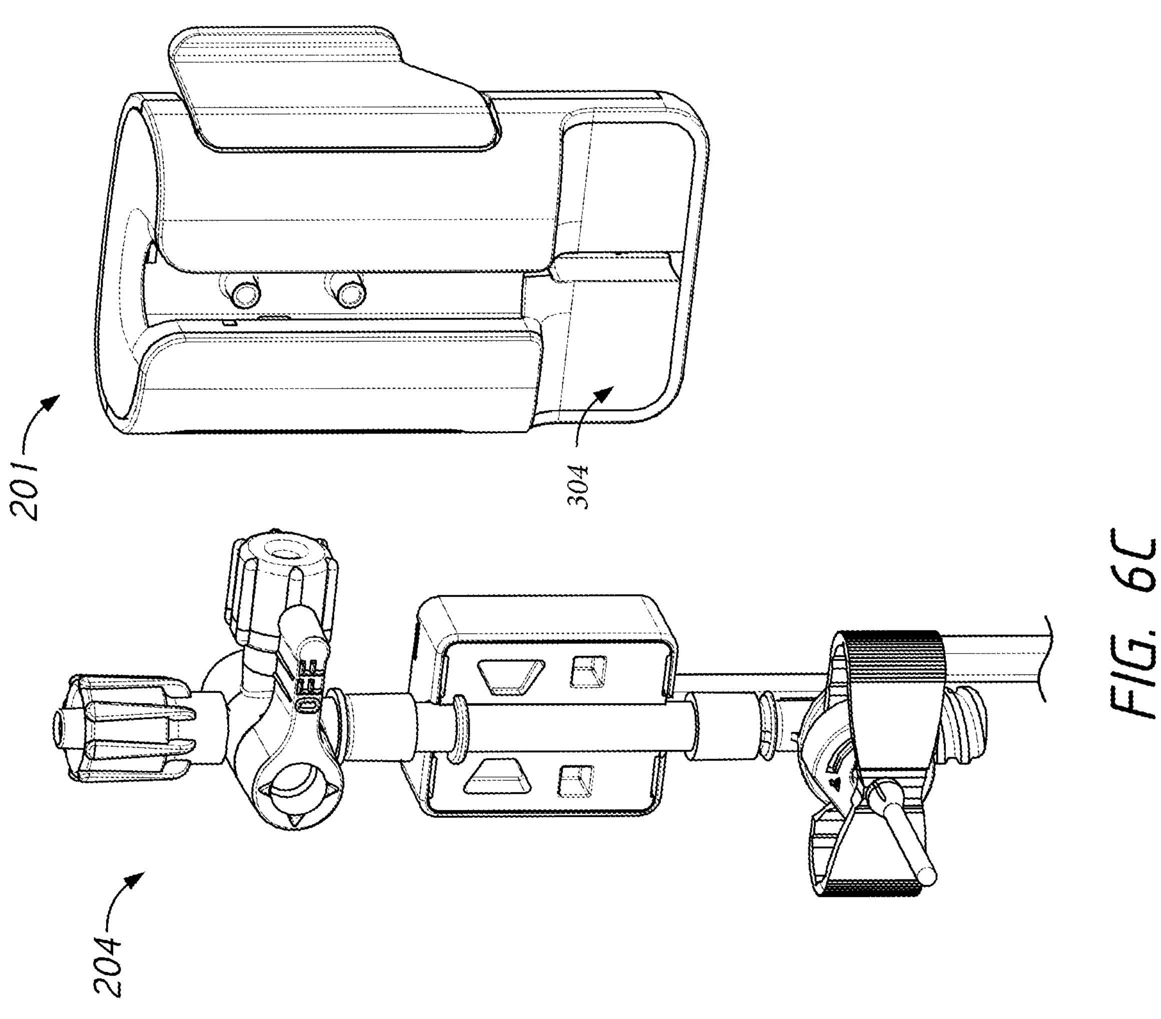
Figure 6B:
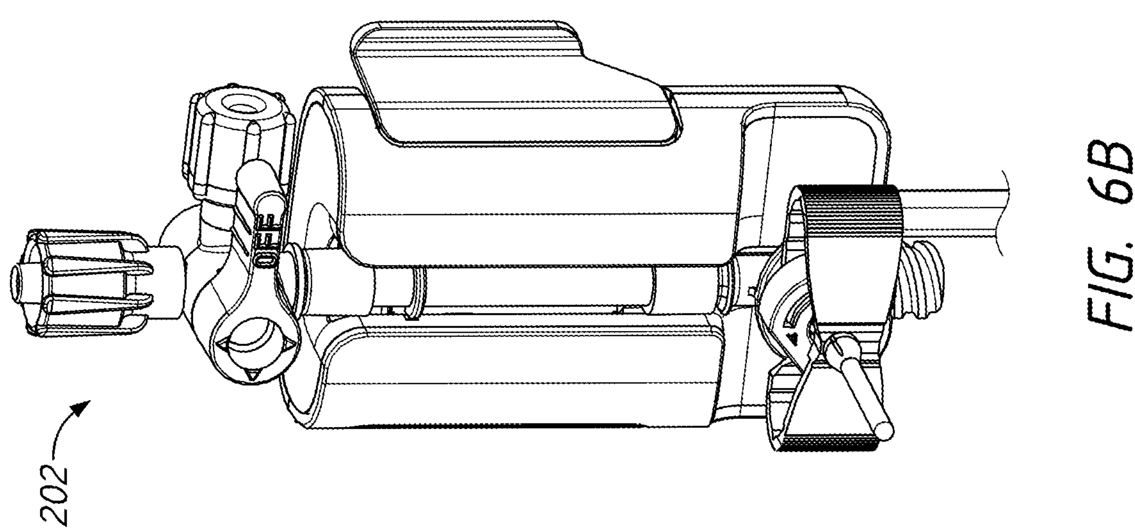
Figure 6D:
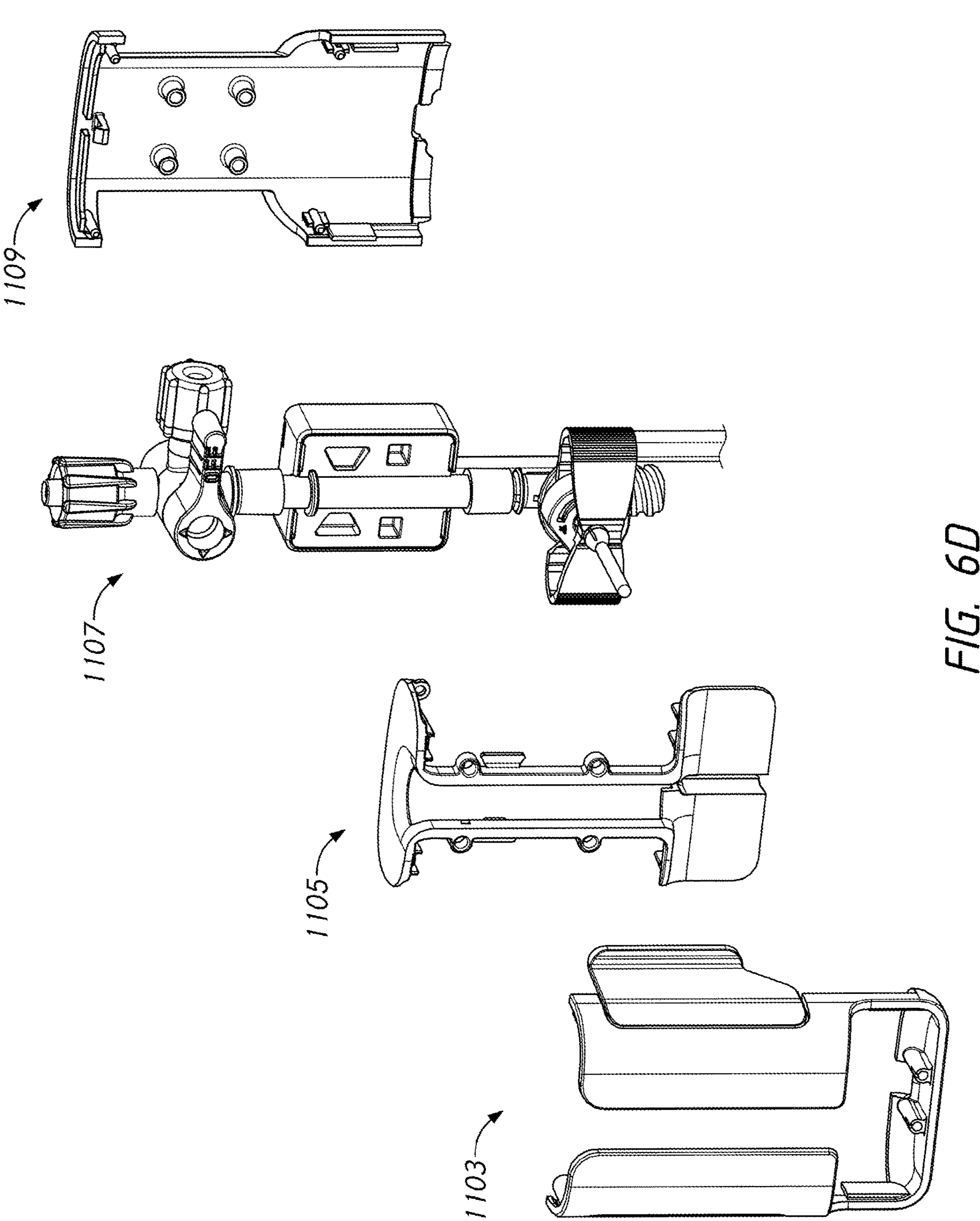

FIGS. 5E, 6A-6D illustrate views of example implementations of the transducer shroud 201. The example transducer shroud 201 may include similar structural and/or operational features described with reference to example transducer 101 of FIG. 1. FIG. 6A illustrates an example transducer shroud 201 mounted to a mounting plate 301 through engagement of a transducer wings 305 with mounting plate brackets 303. The transducer shroud 201 may be configured to hold a transducer 213 coupled to a patient. FIG. 6B illustrates a shroud system 202 that may include a transducer shroud 201 and transducer 213. FIG. 6C illustrates an exploded view of the shroud system 202 that includes a transducer 204 and transducer shroud 201. As shown, the shroud may include one or more components for holding or coupling one or more transducer components 204. In some examples, the transducer shroud may include a back securing component or portion 304 configured to secure one or more parts of the transducer and/or cannula tubing from unintentional forward and/or backward movement. In some examples, the back securing portion 304 may not include a front securing portion so as to allow easier access to components of the transducer 204. FIG. 6D illustrates an exploded view of the shroud 201. As illustrated, the shroud 201 may have a plurality of components, including but not limited to a back plate or back component 1109 configured to receive the transducer 1107. The shroud 201 may have a middle component 1105 configured to secure the transducer to within the shroud. The shroud 201 may include a cover plate or cover component 1103 configured to cover the front of the transducer 1107. The cover component 1103 may include wings such as described in FIGS. 7A-7C.

Figure 7A:
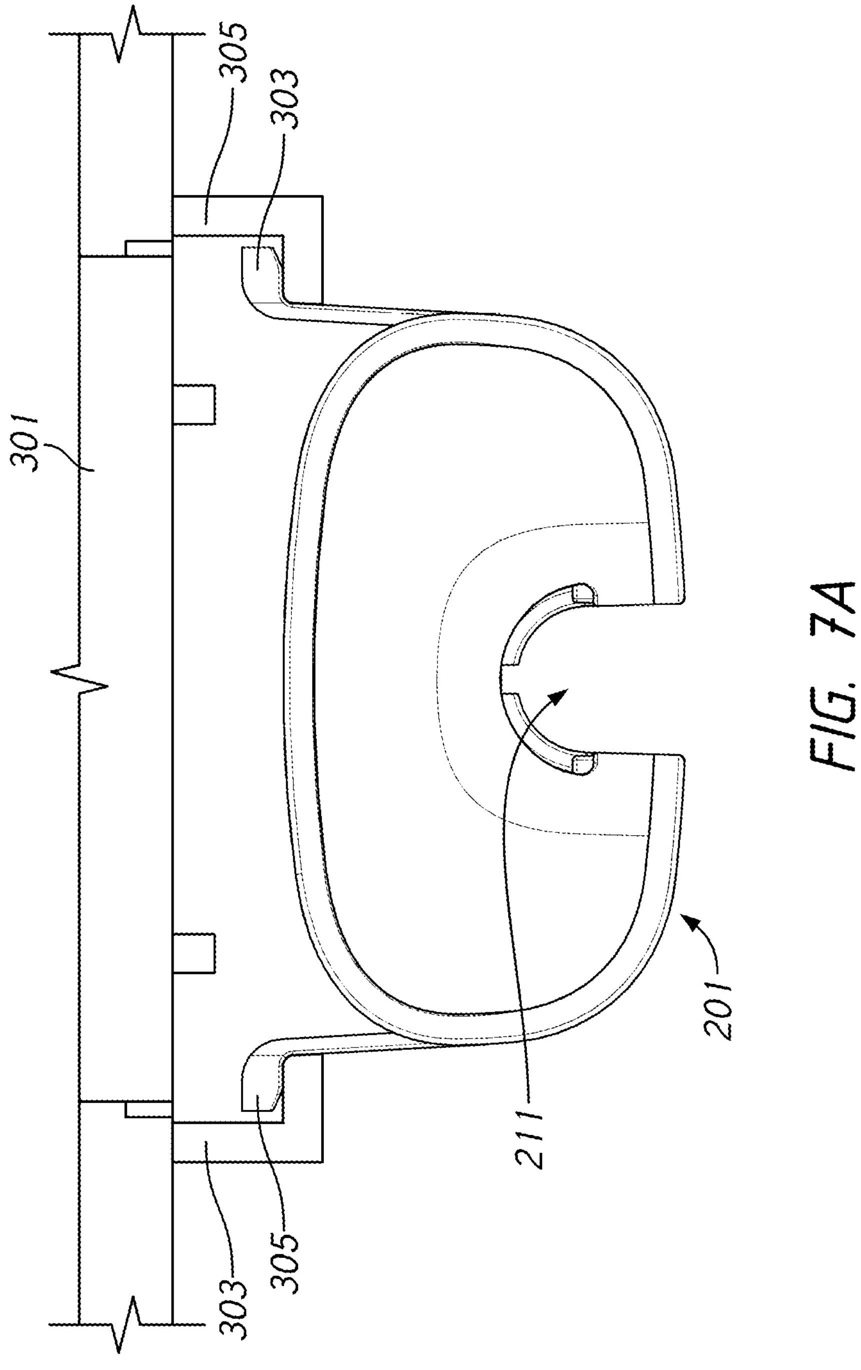
Figure 7C:
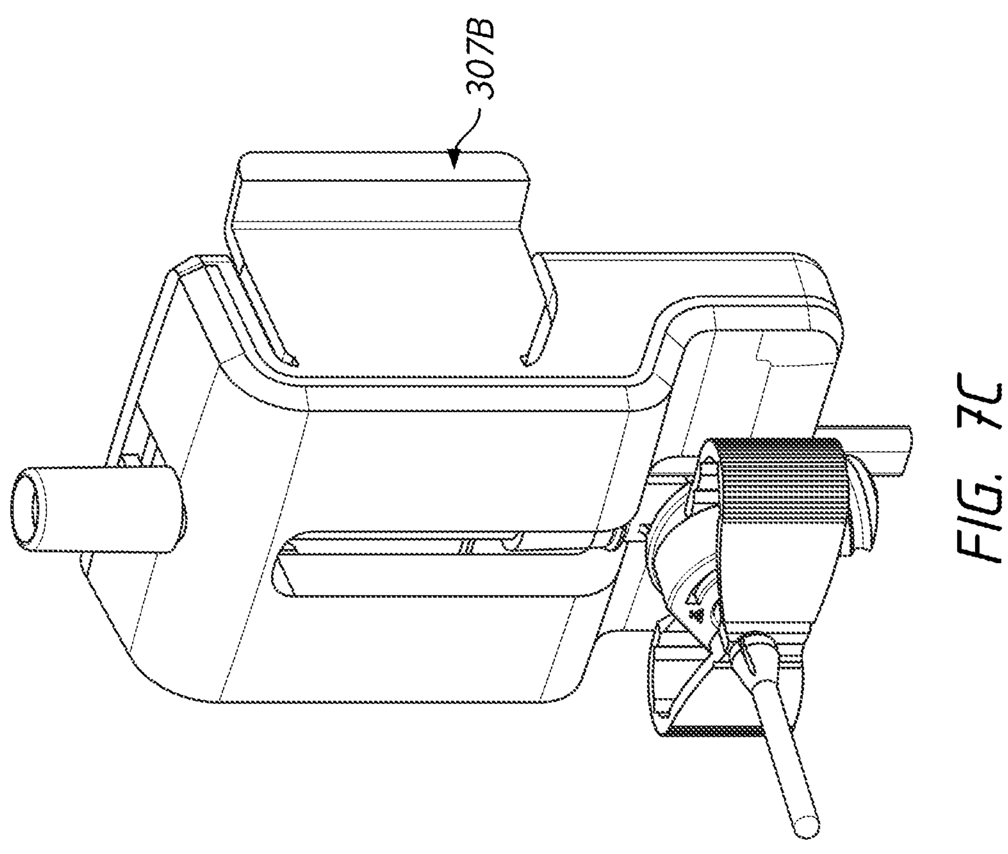
Figure 7B:
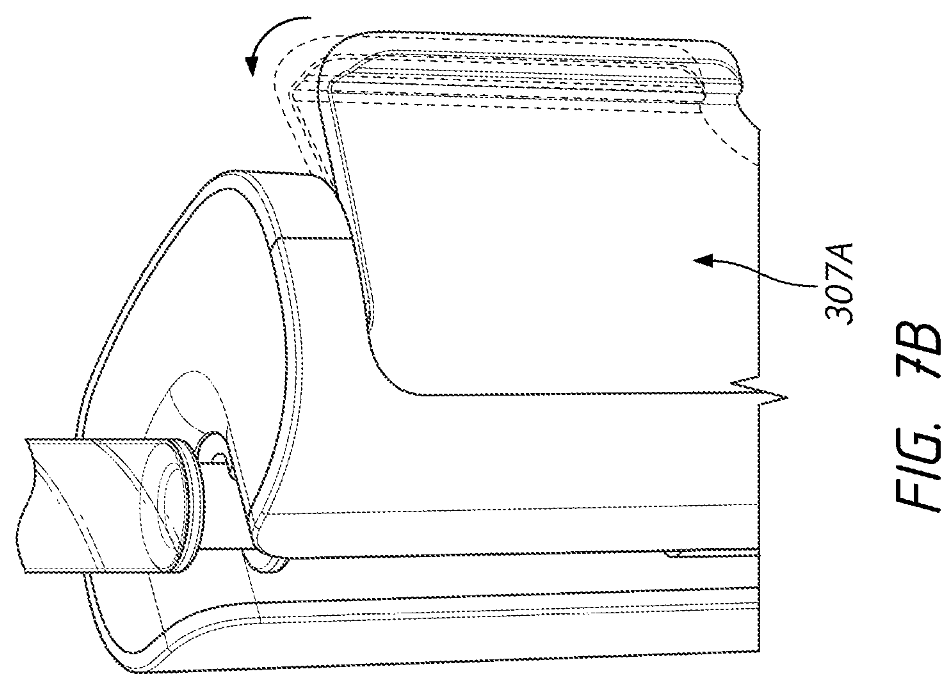

As shown in FIGS. 7A-7C, a transducer shroud 201 can include one or more movable wings 305. The wings may be configured to engage with a mounting plate 301 through a mount 303. The mounting plate 301 and mount 303 may be any number of shapes or configurations. One or more of the movable wings 305 may be configured to provide an outward force when moved or deformed towards a center of the transducer shroud 201. The outward force may provide sufficient outward tension or force to removably couple the transducer shroud 201 to the mounting plate 301. FIG. 7A illustrates an example top view of a transducer shroud 201 mounted on a mounting plate 301. As illustrated in FIG. 7A, the wings 205 may be configured to engage with brackets 303 of a mounting plate 301. The brackets 303 may be any number of sizes and/or distances from each other on the mounting plate 301. Advantageously, the wings 305 may be configured to couple the transducer shroud 201 to the mounting plate 301 with brackets 303 that are configured to be of different distances from each other and/or shapes and/or sizes. Accordingly, the transducer shroud 201 may be mounted to a variety of different types of mounting plates with different bracket 303 orientations. In some examples, the transducer shroud 201 may be configured to mount to brackets 303 having a distance between the first and second bracket of 30 mm, 28 mm, 26 mm, any distance between, or greater than or less than 30 mm or 26 mm. In some examples, the distance between brackets may be referred to as a slot. A depth of the slot may be any number of depths, including, but not limited to 2.5 to 5.5 mm or a value outside of that range.

FIGS. 7B and 7C illustrate perspective views of example wings 307A, 307B. The wings 307A, 307B may facilitate universal or near universal mounting to a plate 301. For example the wings 307A, 307B may be integrated and flex with a large enough range so as to mount the shroud 201 to mounting plates with small and large distances between mounting brackets 303. As illustrated, a transducer 204 may have different shapes, including, but not limited to a curved shape, such as illustrated in FIG. 7B, or a substantially flat shape, such as illustrated in FIG. 7C. The shape of the wing may be similar to the shape of the transducer 204. For example, in a curved shape example, a flex arm or wing 307A may be curved. In another example, a flex arm or wing 307B may be substantially flat or a hinged petal. The flex arm or wing 307A, 307B may be part of a molded shape of the transducer shroud, such as illustrated in FIGS. 6A-6D. For example, the shroud may include a single unit of rigid or semi-rigid material on at least a side portion of the transducer 204. A wing may, in some examples, form a part of that single unit with cutouts to allow for movement of the wing from a main part of the single unit of material. In some examples, the wing may be a separate component. For example, the wing may be a separate component coupled to a spring system to allow for movement of the wing in coupling the transducer 204 to a mounting plate.

Example Graphical User Interfaces

FIGS. 8A-8G, 9A-9G, 10A-10D, 11A-11D, 12A-12C, 13A-13F illustrate example user interfaces that may be displayed by a monitor device of the system described herein, such as example monitor device 105 described with reference to FIG. 1 or example monitor devices 205*a* or 205*b* described with reference to FIG. 2. The data for rendering the graphical user interfaces described below may be generated by an adapter of the system described herein, such as example adapter 103 described with reference to FIG. 1 or example adapter 203 described with reference to FIG. 2.

FIGS. 8A-8G show example user interfaces that may display parameters or information relating to a patient's hemodynamic status and/or other physiological parameters or information. The user interfaces of FIGS. 8A-8G may be interactive and may be configured to receive a user input. For example, a user may touch the display at various portions of the user interface which may cause the user interface to update, display different data, display a different user interface etc.

FIGS. 8A-8E illustrate aspects of an example interface that may include at least one graphical representation of physiological conditions of a patient. The graphical representation may include a graphical representation of a patient's physiology. In some examples, aspects of the physiology may be accented or highlighted, such as the lungs or the brain in the graphical representation, based on physiological parameters associated with the patient. For example, a color, brightness, or other aspect of the representation of the physiology may be changed based on a physiological parameter. For example, if a patient's physiological parameters indicate healthy lung function, the lungs of the patient may be shown as green or another color. If the patient's physiological parameters indicate abnormal lung function, the lungs of the patient may be shown as a different color than green. In some examples, the graphical representation of the patient's physiology may be emphasized or changed based on the selected physiological parameters to display. For example, if SpO2 is selected for display, a patient's lung function or other parameter associated physiology may be graphically represented or highlighted. A size of the graphical representation may be changed based on a selected layout of parameters.

In some examples, different types and/or aspects of a graphical representation may be emphasized or shown based on a user selection. For example, one or more of a graphical representation of a patient physiology, radial gauge associated with a physiological parameter value, textual representation of a physiological parameter value, graphical or waveform representation of a physiological parameter value, or other aspect or representation of a measured physiological parameter may be displayed on a monitor. The size, location, and presence of one or more of the aforementioned representations may be adjusted based on a user input. FIGS. 8A-8E illustrate example screens with alternative orientations and selections for display of physiological parameters.

Figure 8A:
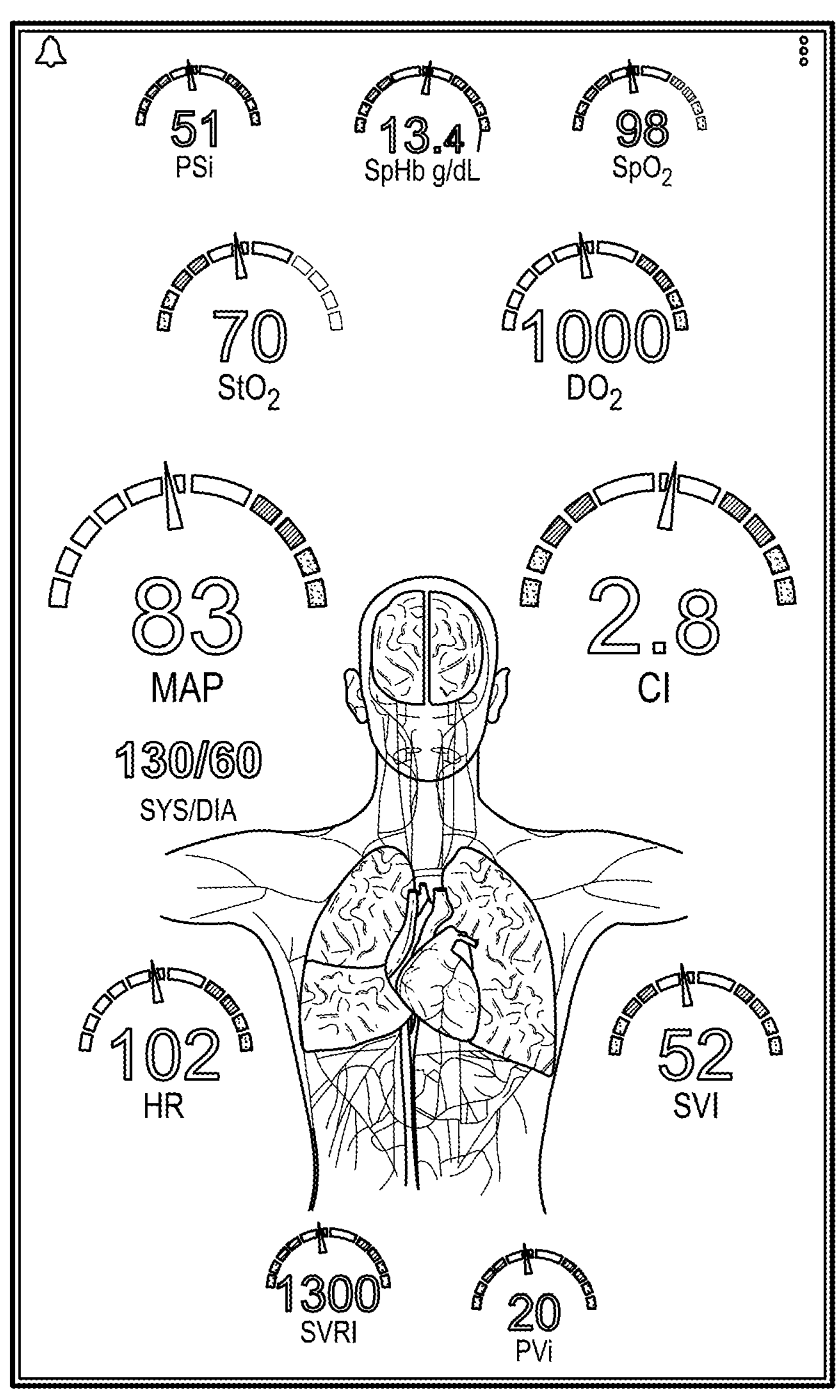
Figure 8B:
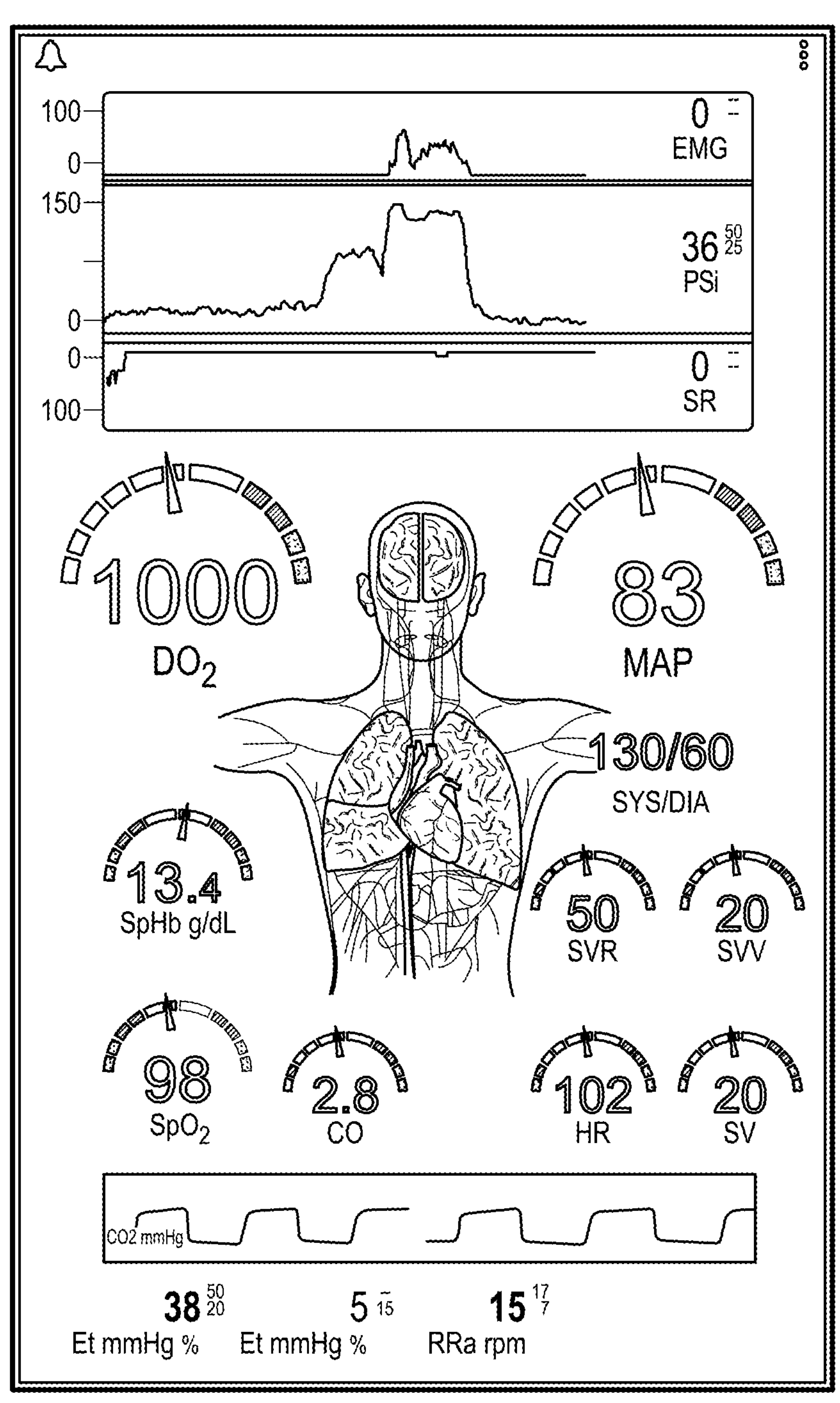
Figure 8C:
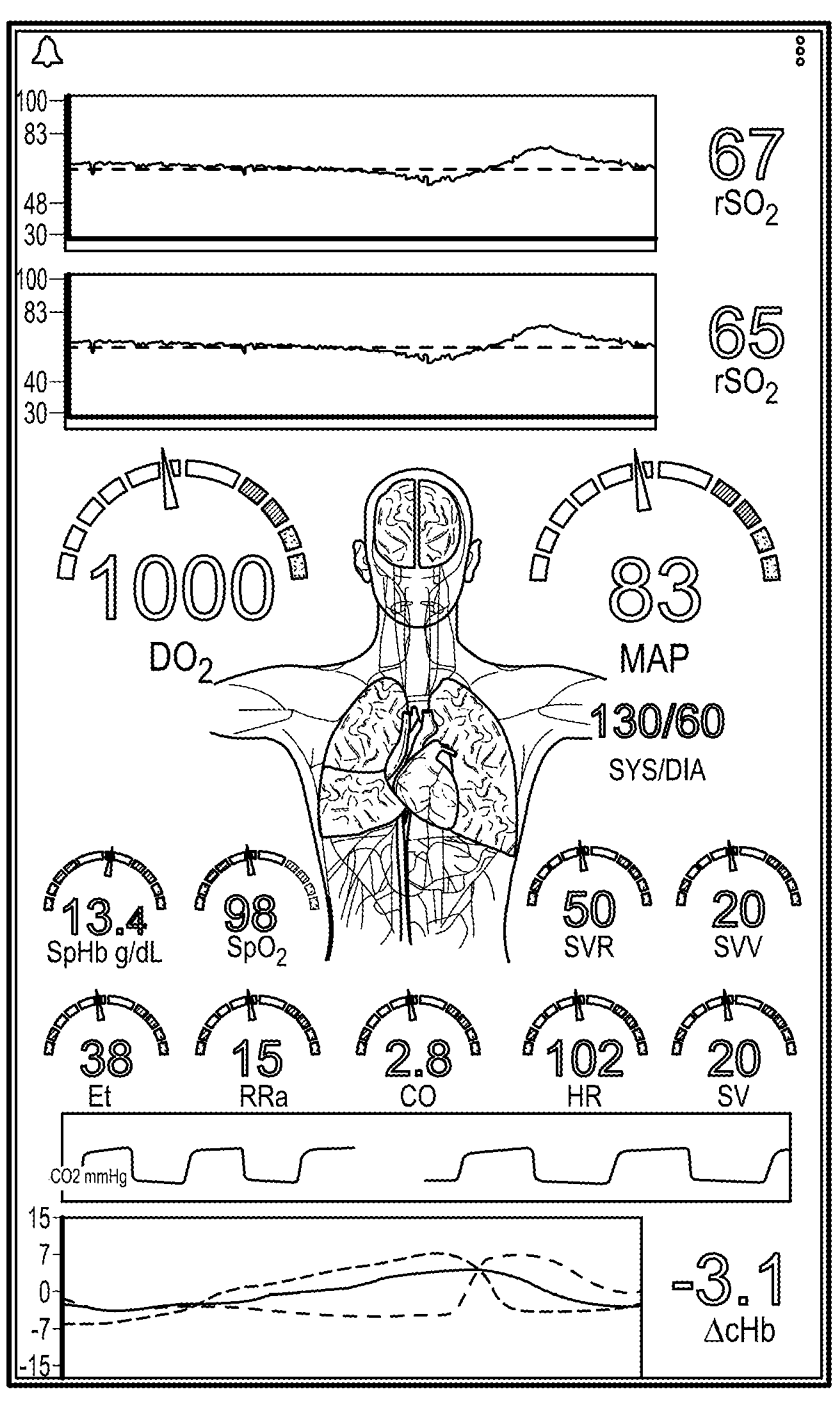
Figure 8D:
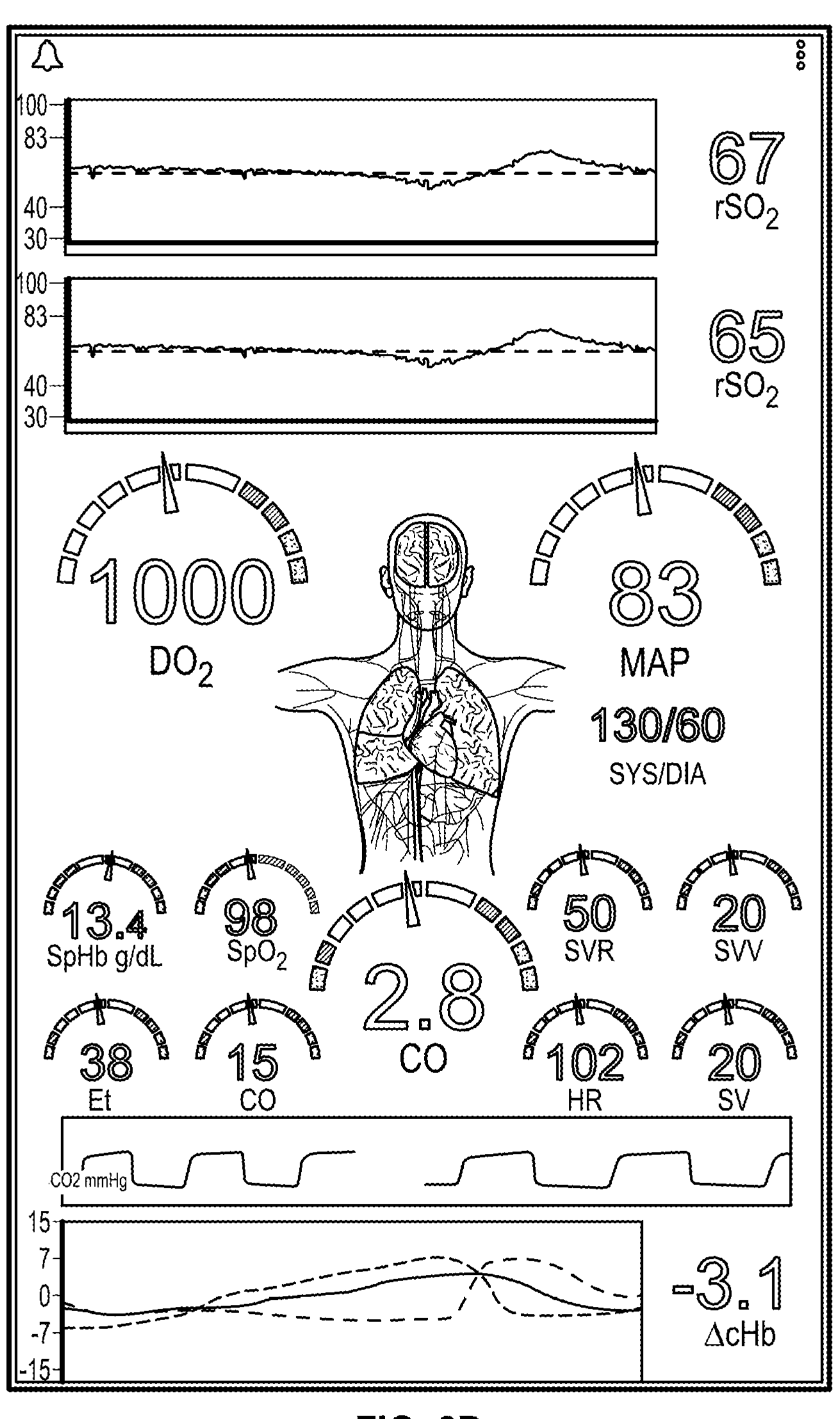
Figure 8E:
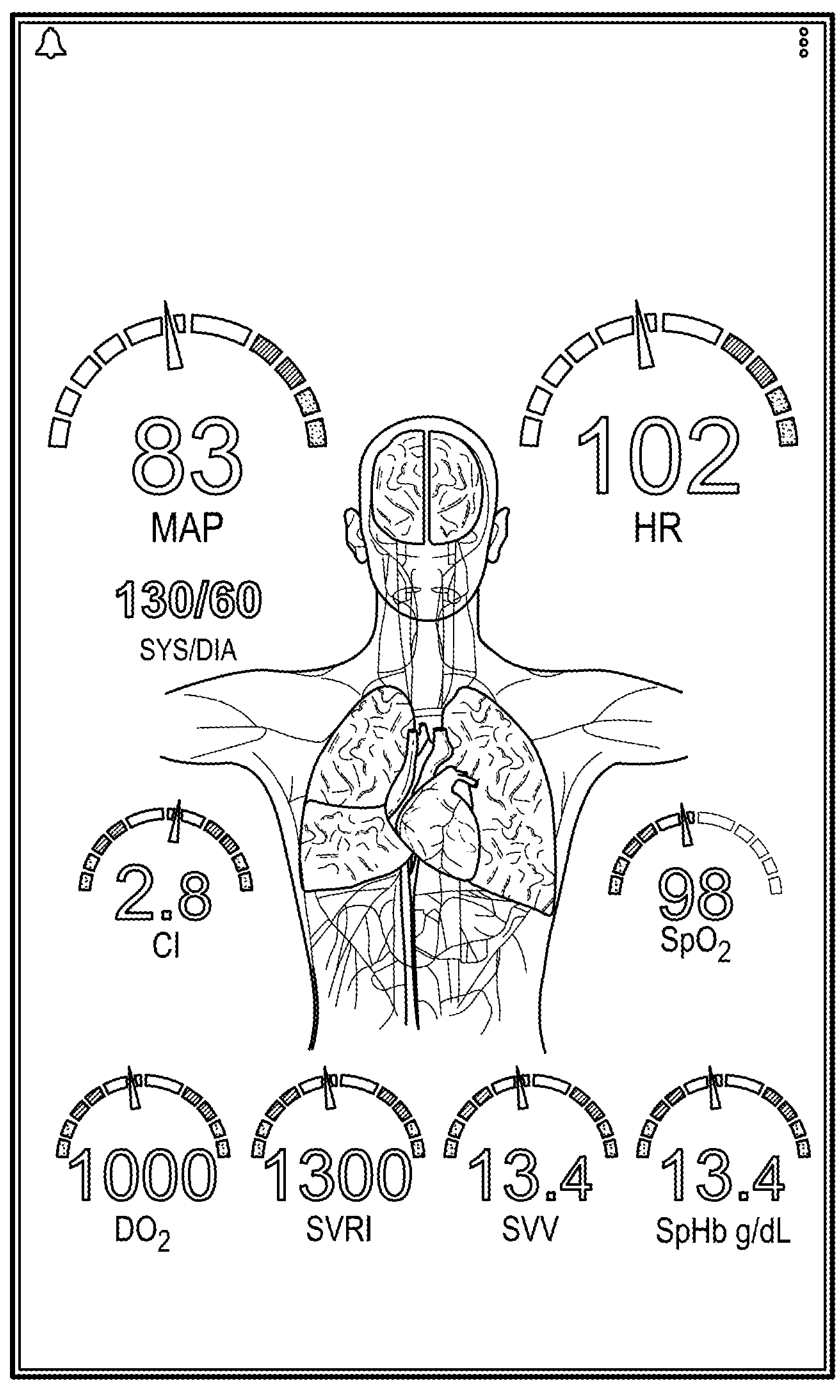
Figure 8F:
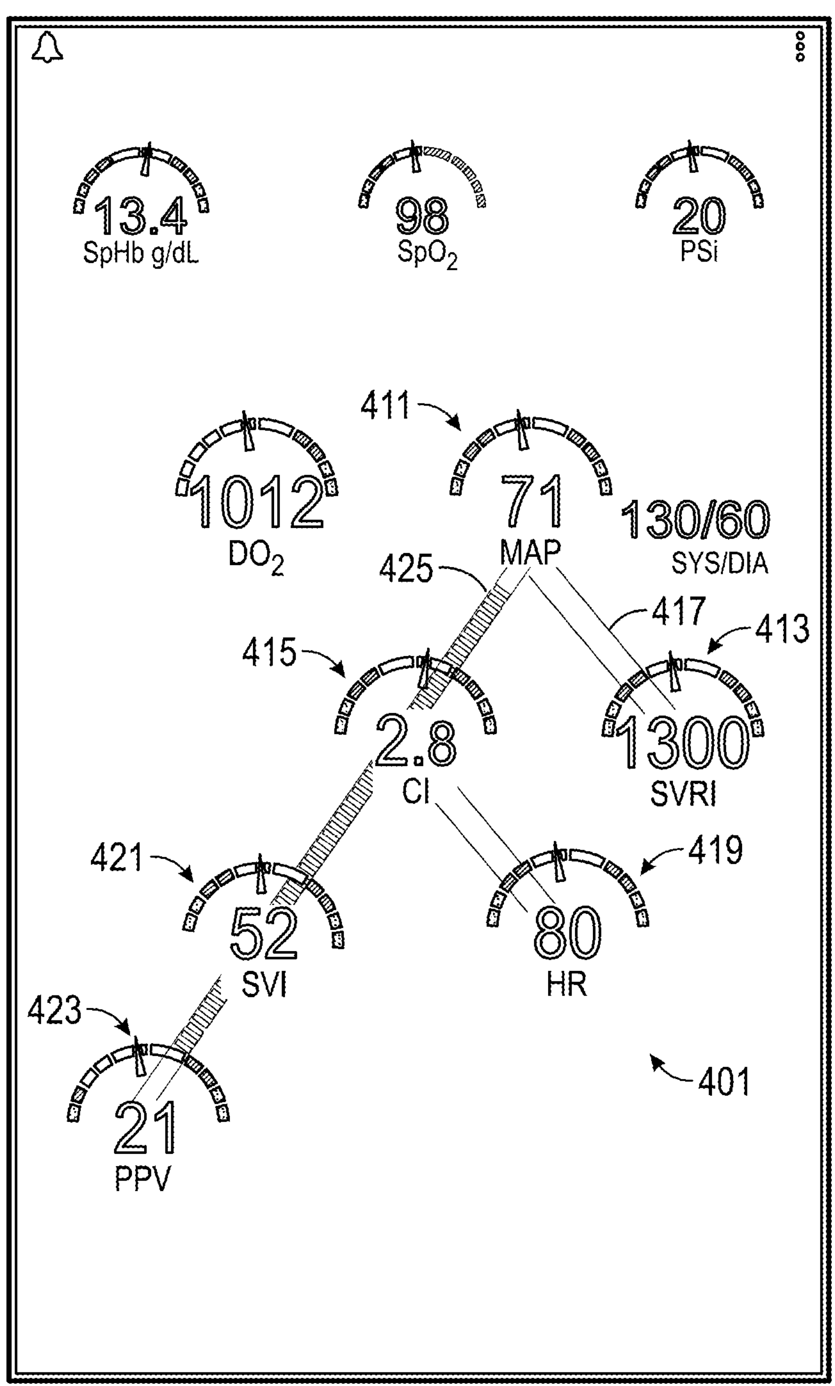
Figure 8G:
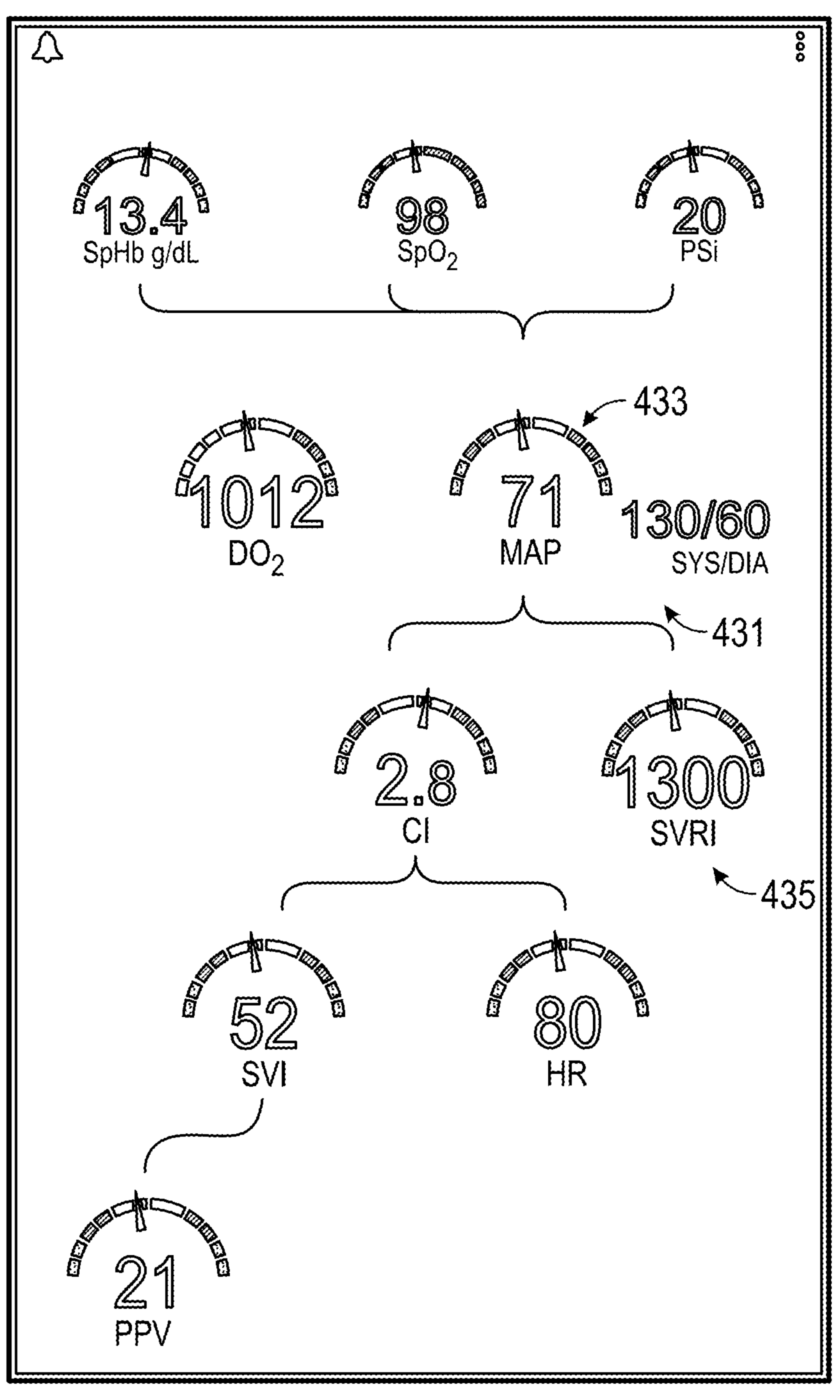

FIGS. 8F-8G illustrate some example interfaces for display of relationships between physiological parameters. For example, as illustrated in FIG. 8E, a GUI may be configured to display one or more relationships in a tree or factorial structure. Advantageously, the configuration of the interface may facilitate easy and fast understanding of the relationship between parameters in addition to the value of parameters themselves. For example, the layout, order and/or emphasis of physiological parameters may help transmit information to the user of the interface.

FIG. 8F illustrates an example layout of parameters in a hierarchical tree 401. The hierarchical tree 401 may include a plurality of related parameters associated with one or more physiological parameters. For example, a blood pressure associated score (such as a mean arterial pressure or MAP score) 411 may be related to cardiac output (CO), cardiac index (CI), oxygen delivery (DO2), oxygen delivery index (DO2I), system vascular resistance (SVR), system vascular resistance index (SVRI), stroke volume (SV), heart rate (HR), pulse pressure variation (PPV), level of consciousness (BIS), dynamic arterial elastance (EA-dyn). The interface may be configured to show a mathematical or influencing relationship between parameters by arranging the parameters in a hierarchy (such as a pyramid).

The level at which a parameter is displayed in the hierarchy may be associated with the influencing relationship of the parameter with the at least one main or primary parameter. For example, the interface may display at least one main or primary parameter on a first level and influencing parameters (or parameters that may influence the at least one main or primary parameter) on lower levels. In some examples, the level below a main or primary parameter at which an influencing parameter is displayed may be associated with the relative importance of the influencing parameter on the main or primary parameter. In some examples, the level below a main or primary parameter may be associated with the relative dependence of the influencing parameter on the main or primary parameter. Other associations may additionally or alternatively be used for determining a location for display of a parameter in the hierarchy 401. In some examples, the interface may display at least one main or primary parameter at the top of a geometry and at least one first influencing parameter immediately below the at least one main or primary parameter. Parameters that influence the at least one first influencing parameter may be displayed below the at least one primary or main parameter, such as a mean arterial pressure, and lower areas of the geometry are populated by parameters that influence the main parameter. For example, the MAP 411 may be influenced by CO 415 and SVR 413. Thus, CO 415 and SVR 413 may be displayed below the MAP 411 in the tree or geometry 401. In another example, the CO 415 may be influenced by SV 421 and HR 419. Thus, SV 421 and HR 419 may be displayed below the CO 415 in the tree or geometry 401. In another example, SVR 413 may be influenced by BIS (not shown). Thus, BIS may be displayed below SVR 413. In another example, SV 421 may be influenced by PPV (or SVV) 423. Thus, PPV (or SVV) 423 may be displayed below SV 421. Other parameters may additionally or alternatively be displayed in the same or other positions.

Relationships between parameters may be additionally or alternatively be displayed using lines, connectors, or other graphics configured to indicate a connection between a first and second parameter. FIG. 8F illustrates at least one graphic 417, 425 between parameters in the shape of a line or dashed line configured to indicate a connection between two or more parameters. FIG. 8G illustrates an alternative method indicating relationships between parameters. For example, one or more brackets 431 may be used to indicate that one or more influencing parameters 435 are related to one or more other parameters 433. Other types of graphics may additionally or alternatively be used.

In some cases, relationships between parameters may be highlighted or otherwise accented based on whether an influencing parameter is currently influencing or more strongly influencing a value or trend of a particular parameter. For example, as is illustrated in FIG. 8F, the relationship line 425 between CI and MAP is accented or highlighted by a dashed line in comparison to the relationship line 417 between MAP and SVRI. The relationship line may be accented when a property or value of the influencing parameter is contributing to the current value of the main parameter. The accenting may be implemented as an alert for different scenarios. The alert may be turned on or off based on a user input. Advantageously, this can allow a caregiver to quickly perceive the source of an issue and respond to a patient with a new treatment regimen if necessary or understand if applied treatments are working. Table 1 illustrates some example clinical scenarios where MAP relationships between parameters may be accented. It is of note that merely using MAP as an indicator for diagnosing hemodynamic conditions can result in inaccurate diagnoses. Thus, having multiple parameters contributing to the MAP and what is influencing the MAP may be useful in a clinical setting for improved medical care.

TABLE 1

Displaying different clinical scenarios for the state of influencing parameters on MAP scores that may be indicated by a hierarchical tree and relationship display such as described herein.

| Scenario | MAP | CO | SVR | HR | SV | SVV |
|---|---|---|---|---|---|---|
| Aesthetic Induced Hypotension | Low | | Low | | | |
| Sepsis induced Hypotension | Low | High | Low | High | Low | High |
| Fluid Responsive | Normal/ Low | | | | Low | High |
| Shock State - Hypovolemic | Low | High | | | | High |
| Shock State - Cardiogenic | Low | Low | High | | | Normal/ Low |
| Shock State - Neurogenic | Low | Normal/ Low | Low | | | High |
| Shock State - Anaphylactic | High/ Normal | Low | | | | High |
| Shock State - Septic (early) | Low | High | Low | High | | High |
| Shock State - Septic (late) | Low | Low | High | Low | | Low |

TABLE 1-continued

Displaying different clinical scenarios for the state of influencing parameters on MAP scores that may be indicated by a hierarchical tree and relationship display such as described herein.

| Scenario | MAP | CO | SVR | HR | SV | SVV |
|---|---|---|---|---|---|---|
| Shock State - Obstructive | Low | Low | High | | | |

Figure 8H:
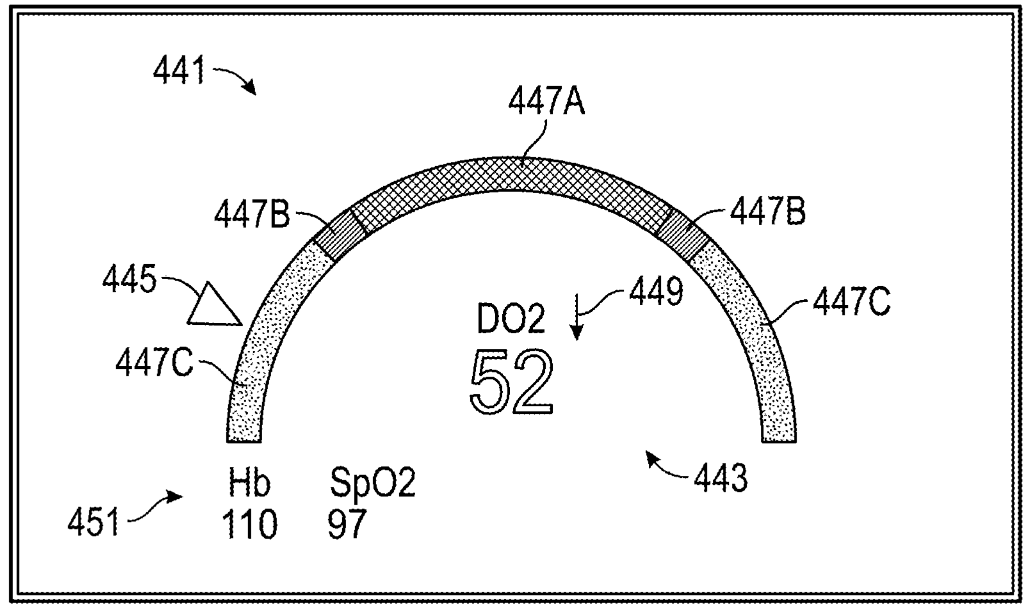

Parameter values may be indicated in one or more ways on the interface. For example, a parameter value may be indicated by display of the numerical value, an approximation of the numerical value, an index associated with a numerical value, or another alphanumeric representation of the parameter value. Parameter values may be indicated through a graphical representation of the parameter value. For example, a parameter value may be displayed as or in association with a radial gauge. The radial gauge may be a graphic, such as an image updated at intervals or an animation. FIG. 8H illustrates example radial gauge displays 441 that may be utilized as part of an interface. For purposes of clarity in the figures, only one of the radial gauge displays are indicated 441. However, each of the parameters, such as SVI 443, are shown to have a corresponding radial gauge display. In some examples, some or all of the displayed parameters may have an associated radial gauge display 441. In the illustrated example, the radial gauge 441 may be configured to indicate a value of the parameter in relation to a reference value and/or range of values. In some examples, the radial gauge may be a radial gauge. For example, a radial gauge may have a plurality of segments 447A, 447B, 447B and/or an indicator 445. The indicator 445 may be an arrow, needle or other image or animation configured to move or otherwise indicate a location of a value in relation to the segments 447A, 447B, 447C. The segments 447A, 447B, 447C may indicate ranges or zones in which a parameter value is normal or abnormal. For example, a segment 447A may indicate a normal or healthy range of values for a parameter. One or more segments 447B may indicate warning or slightly abnormal values for a parameter. If an indicator 445 is illustrated as pointing or near a particular segment, the parameter may be within those range of values associated with that particular segment. Additionally or alternatively to the radial gauge, a graphic 449 may be displayed to indicate information associated with the parameter being illustrated. For example, a graphic 449 may include an arrow, emoji, or other graphic to indicate a trend, health, accuracy, or other information associated with a parameter value. In the illustrated example, a graphic 449 includes an arrow. The direction of the arrow may correspond to a rate of the trend. For example, an arrow pointing down may indicate a downward trend and an arrow pointing up may indicate an upward trend. The arrow is shown as pointing down in order to indicate a downward trend of the parameter value. The arrow may have a color configured to illustrate a current status of the value. For example, a red arrow may indicate that the value is within an unhealthy range of values, a yellow arrow may indicate that the value is within a warning range of values, and a green arrow may indicate that the value is within a healthy range of values. In some examples, one or more associated parameters 451 may be displayed at or near the radial gauge and/or parameter value 443.

Figure 8I:
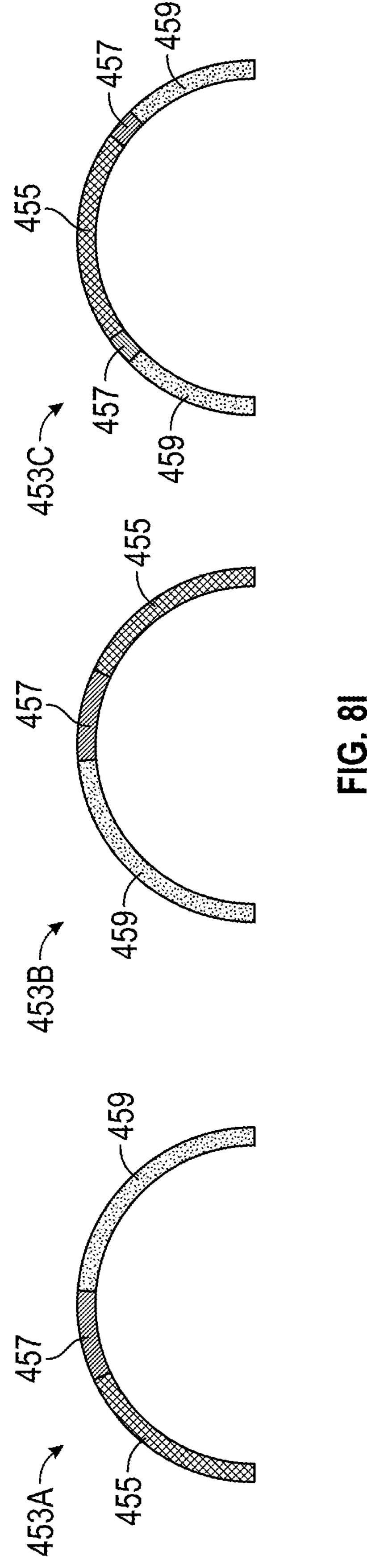
Figure 8J:
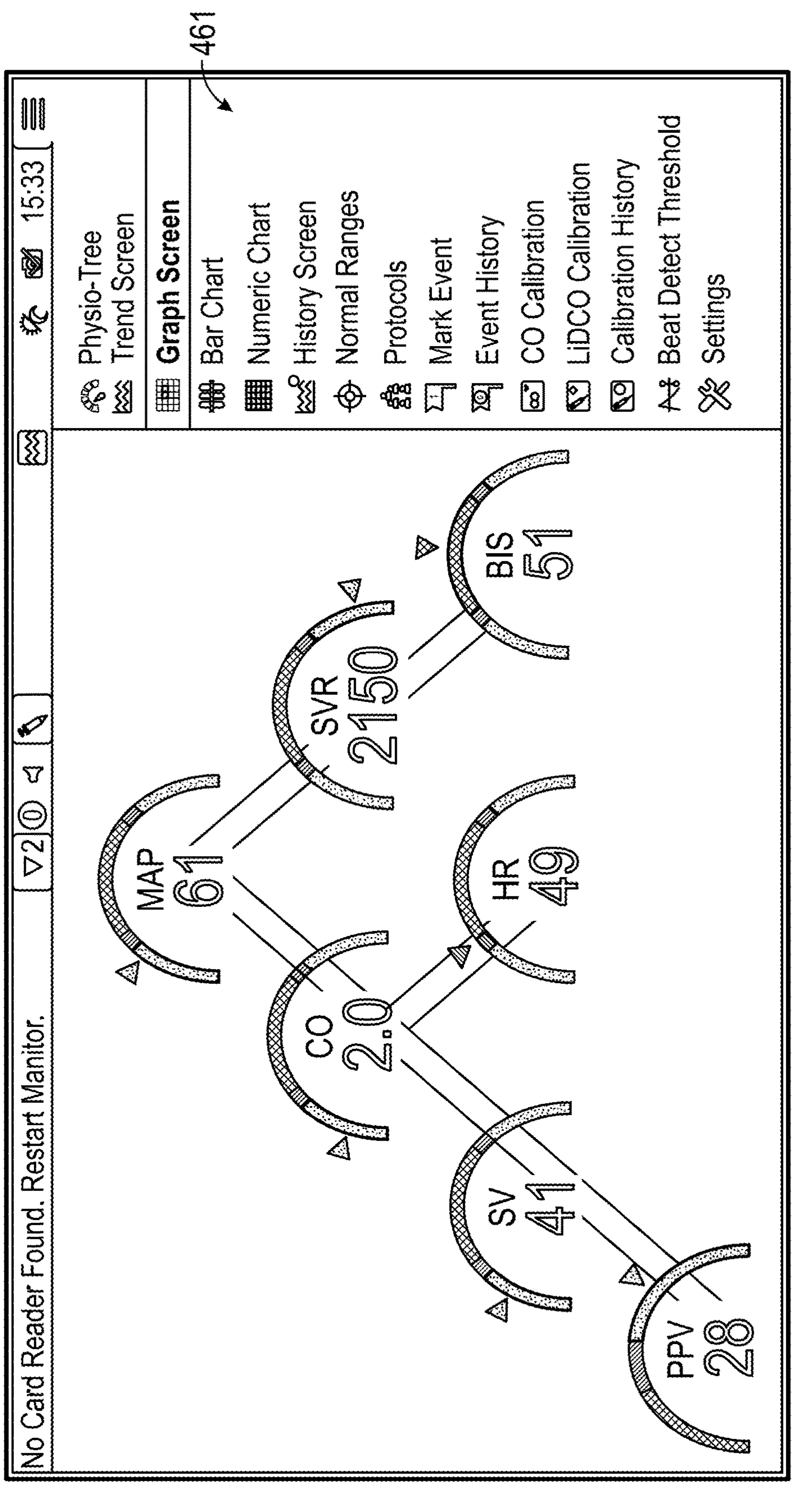

One or more segments 447C may indicate highly abnormal, cautionary, or otherwise bad range of values for a parameter. FIGS. 8I-8J illustrate details of how segments may be illustrated on a radial gauge. For example, a radial gauge may have a plurality of colors. Each segment have an associated color. The colors may be contrasting for ease of readability. In some examples, the colors of the segments may be shaded differently based on whether a value is within a range associated with the present segment. For example, FIG. 81 illustrates a plurality of different types of radial gauge components 453A, 453B, 453C. Radial gauge component 453A illustrates an example single sided radial gauge segment orientation wherein a lower range is normal. Radial gauge component 453B illustrates an example single sided radial gauge segment orientation wherein an upper range is normal. Radial gauge component 435C illustrates an example double sided set of limits where a central range is normal and lower or higher ranges are both abnormal. A radial gauge component type may be based on the type of parameter. For example, a radial gauge component 435A associated with a normal lower range may be associated with PPV and SVV and/or a radial gauge component 435C associated with a normal central range may be associated with HR, MAP, SV, CO, DO2, SVR, and BIS. Other radial gauge component types and other parameter associations are also possible.

A layout of the radial gauge segments for a particular radial gauge component may be fixed for a particular parameter. For example, a radial gauge segment may have a fixed size and position. A value for ranges associated with one or more of the segments may be normalized or otherwise selected so that the interface is consistent and easy to read. An overall range may change from parameter to parameter. For example, a distribution of range among segments may include: 40% for normal segments, 5-15% for abnormal segments and 35-45% fir abnormal segments. Other distributions may also be possible and distributions may be dependent on radial gauge type and layout.

In the illustrated examples, a normal range is associated with segment 455. Segment 455 may be shaded green or other permissive color. Further, a warning range is associated with segment 457 that is slightly outside the range associated with range 455 (such as above or below segment 455). Segment 457 may be shaded a different color from segment 455, such as a yellow or warning associated color. Further, an abnormal or danger range is associated with segment 459 that is outside the range associated with segment(s) 457. Segment 459 may be shaded a different color from segments 455 and 457, such as a red or non-permissive color. When a value of the parameter or indicator of the value is within a particular segment or associated segment range, such as segment 455, a color or other aspect of the segment may change. For example, segment 455 may be accented, such as by being brightened in color when the value falls within that range.

An interface may display a trend status. As illustrated in FIG. 8H, a trend status 449 may be indicated near a parameter 443 or radial gauge 441. A trend status may depict a direction of a parameter trend over a course of time relative to a baseline taken at a prior time. The baseline and/or time range may be user adjustable, such as a minute to 10 minute trend over a baseline of 30 seconds prior to the start of the time period. A baseline value may be an average of all data above a certain confidence level over a determined time period prior to a trend period. For example, a baseline value may be a 30 second average of all good beat data prior to a trend period. The baseline value may be considered valid for use if the ratio of good data is greater than or equal to 70% or another percentage. Good data may include data that is over a determined confidence level. A trend period may include 5, 15, 30, or 60 minutes. The trend period may be adjustable in 5 minute increments. The longer the trend period, the slower to change the trend indicator. A trend calculation may be a sample of 30 seconds of data at the end of a trend period over the baseline value. The baseline value may be considered valid for use if the ratio of good data is greater than or equal to 70% or another percentage. A trend calculation may be updated at intervals or beat to beat. In some examples, a trend calculation may be updated at intervals that is not beat to beat in order to reduce jitter. A trend direction may be determined based on a range. For example, an upward trend may be associated with a greater than or equal to a limit percentage (for example, 10 percent, 15 percent, or 20 percent) increase from baseline. In another example, a downward trend may be associated with a greater than or equal to a limit percentage (for example, 10 percent, 15 percent, or 20 percent) decrease from baseline. In another example, a stable trend may be associated with a range less than or equal to the determined limit percentage for the upward or downward trend. In some example, the stable trend may be associated with a range, of for example, between −8% and +8% and the upward and/or downward limit percentage may be 10 percent. A gap between the limit percentages and the stable range (such as 2 percent or other) may be used in order to reduce sudden trend changes. Accordingly, a trend indicator may be maintained until a new condition occurs.

A trend status may convey not only direction of the trend, such as an increase or decrease or stability of the trend, but also the zone that the trend is heading towards, such as normal or abnormal. The trend status may facilitate eased understanding of a patient's physiological condition at a glance. In some examples, a trend status color may be determined by a the zone or range of values in which the current parameter value lies. A green trend status indicator may indicate a trend direction (either positive or negative) while in a stable, healthy, normal, or green zone. A red status indicator may indicate a trend direction while outside of a stable, healthy, normal, or green zone. A grey or hollow status indicator may indicate a trend direction regardless of location of the parameter, the trend is stable. For example, a parameter may be abnormal currently, but trending towards normal. The trend status would thus indicate trending upwards towards normal. In another example, a parameter may be currently normal but trending towards abnormal. The trend status would thus indicate trending towards abnormal. In some examples, a color of a trend status may indicate a rate of a trend. In some examples, a color may indicate the current range of the parameter while a shape or orientation of an arrow associated with the trend status indicates the trend. For example, a trend status indicator can include a single sided or double sided arrow. An up arrow may indicate trending towards an upward direction. A downward arrow may indicate trending towards a downward direction. A double sided flat arrow may indicate a stable parameter or no or flat trend. A size of a trend may be an aspect of the graphic associated with the trend status, for example, a size of trend may be indicated by color, angle of the arrow, size of the arrow, or a combination thereof. An interface may include a plurality of settings and/or display options that may be accessed through a menu. FIG. 8J illustrates an example menu 461 that may be part of an interface, such as illustrated in FIG. 8F, that may be used to access different aspects of the interface, display options, and/or update or personalize display settings. Aspects of the interface may include a physio-tree (or hierarchy display such as described above). The interface may additionally or alternatively include a trend screen, graph screen, bar chart, numeric chart, history screen, normal ranges, protocols, mark event, event history, CO calibration, LiDCO calibration, calibration history, beat detect threshold, and settings. The menu 461 may be accessed through a menu icon. The interface may be configured to change color theme based on a user selection of a theme setting, such as a day or night theme.

Figure 8K:
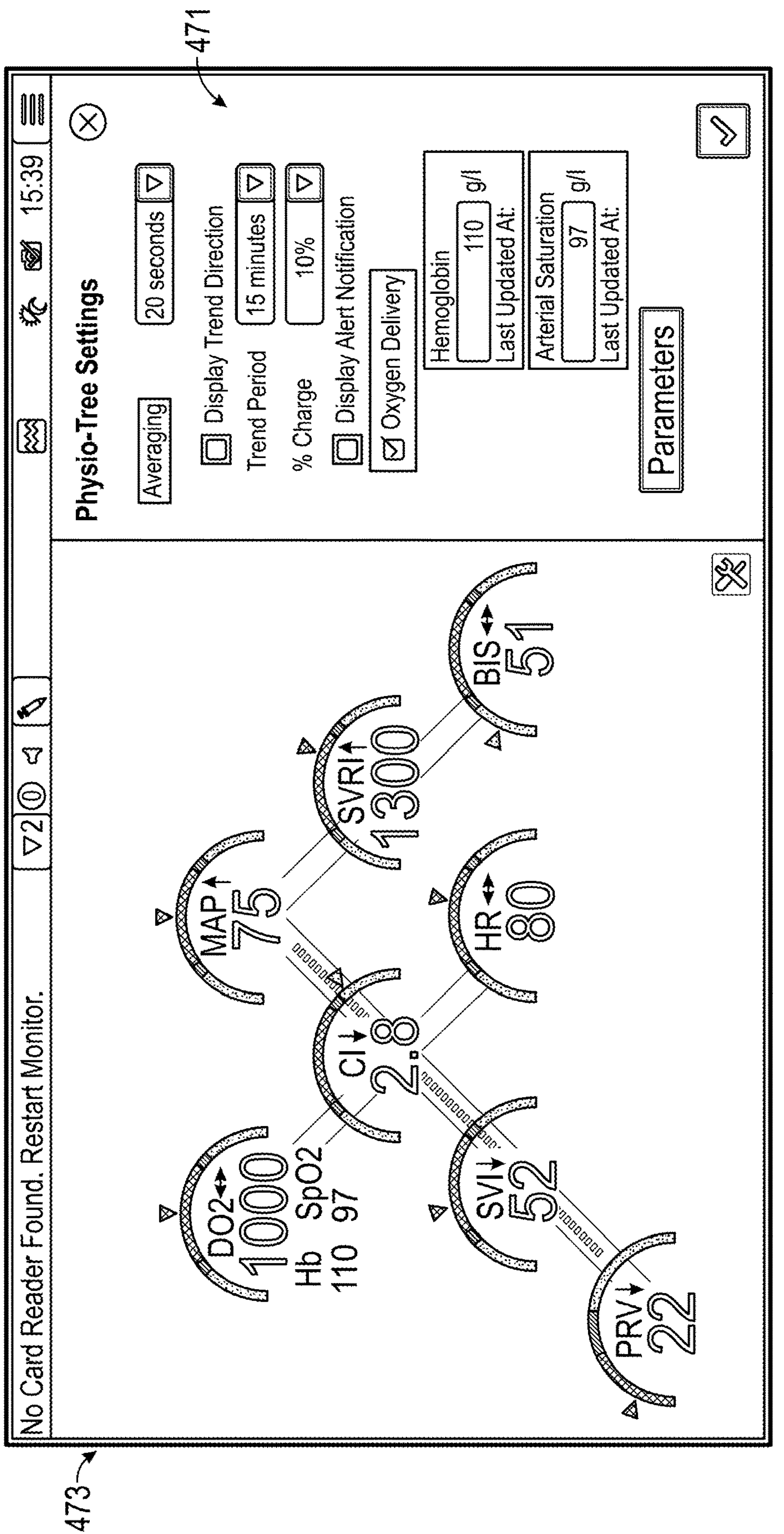

FIG. 8K illustrates an example settings screen 471 of an interface 401. In the illustrated example, the interface 401 may allow a user to update settings of the physio-tree or hierarchy layout 473. Settings may include, but are not limited to a selection for averaging time, a selection for whether to display a trend direction, a setting for trend period, a setting for percentage limit or percentage change for the trend, a setting to display alert notifications, settings for displaying of oxygen delivery related parameters, and/or settings for updating the parameters to display.

Figure 8L:
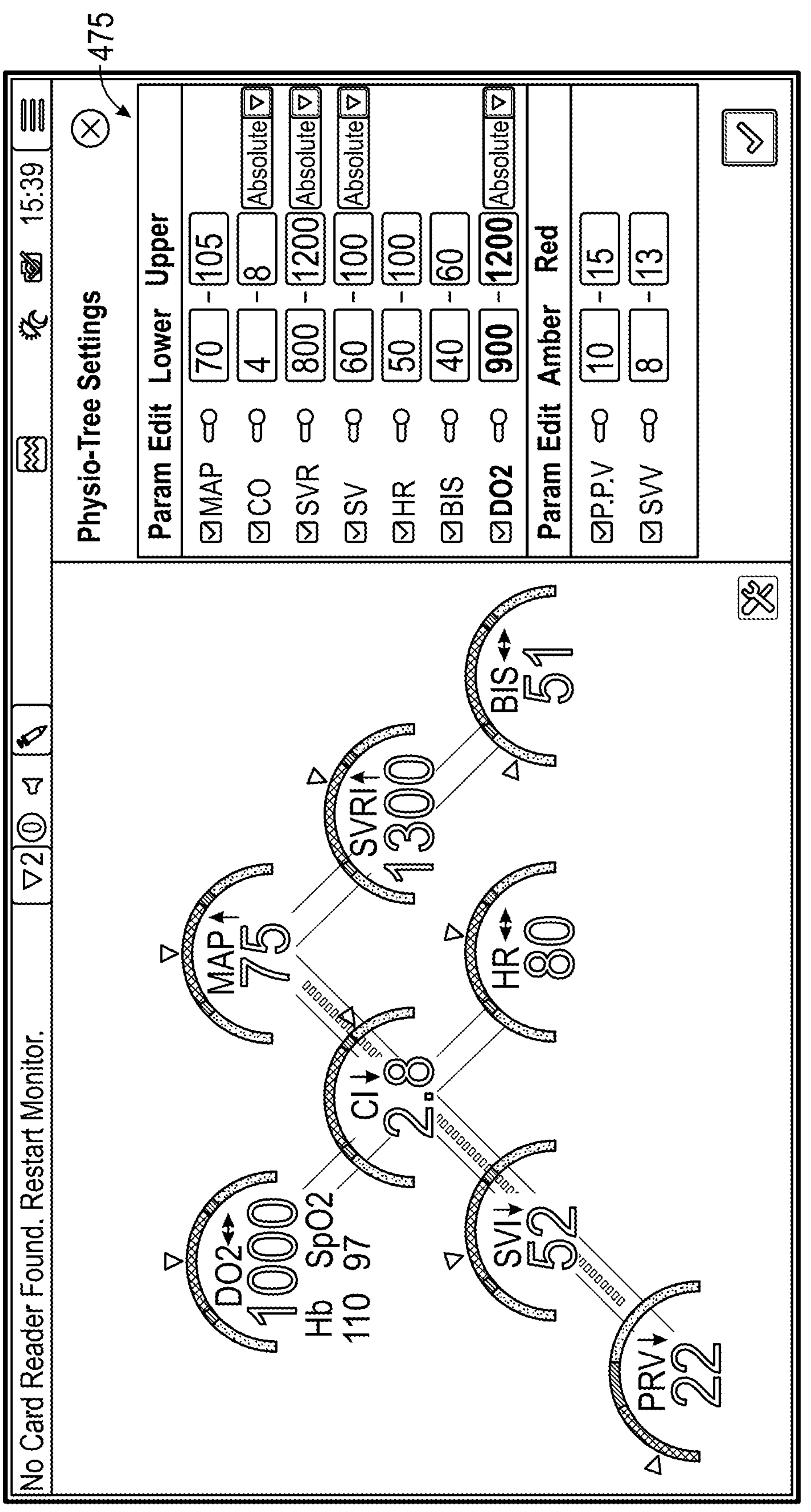

FIG. 8L illustrates an example parameter setting screen in which parameters may be selected for display. In some examples, the parameter setting screens may allow a user to select one or more parameters for display, including but not limited to MAP, CO, SVR, SV, HR, BIS, DO2, PPV, and SVV. The parameter setting screen may allow a user to additionally set ranges for normal and abnormal rangers, such as through upper and lower limits for normal ranges.

Figure 9A:
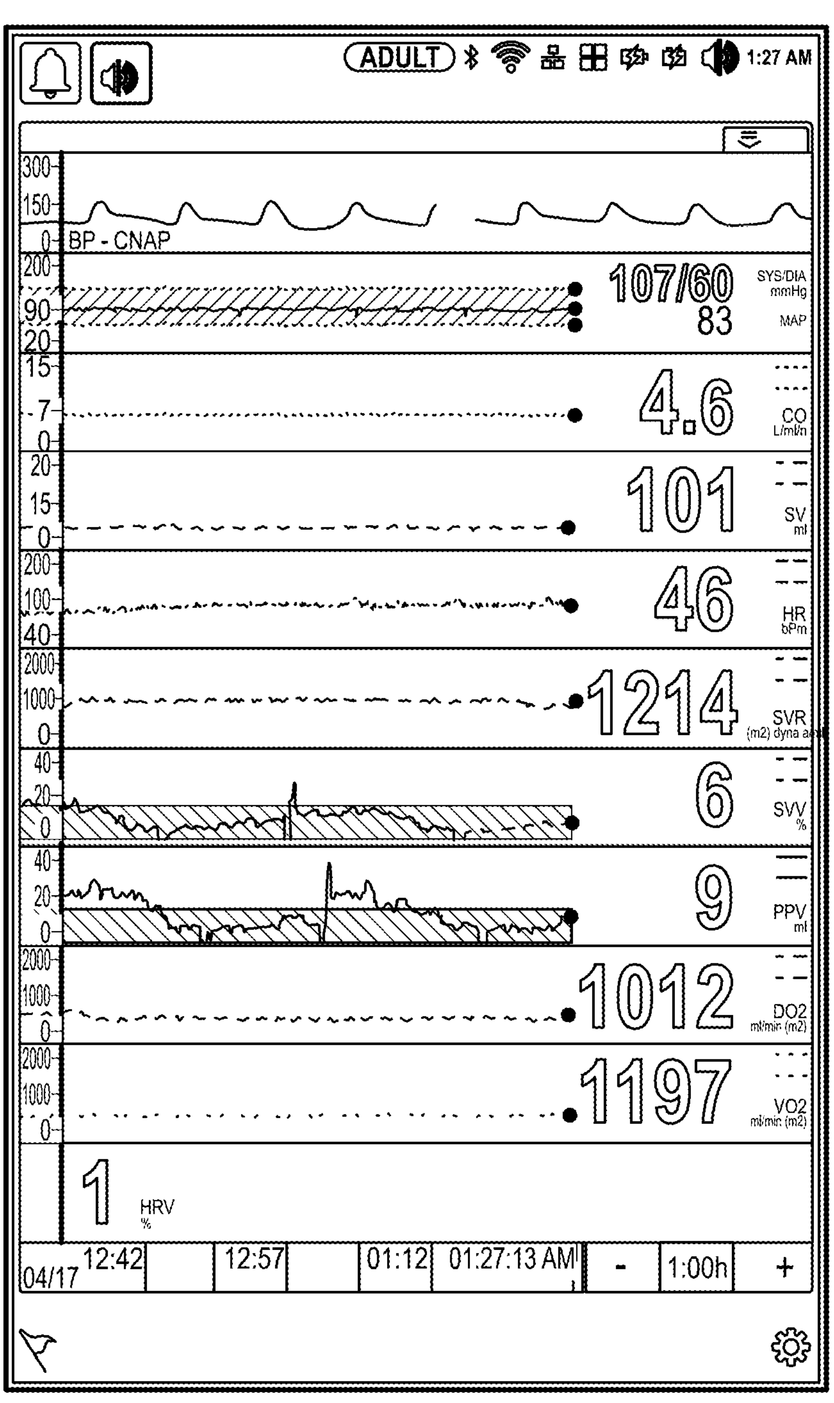
Figure 9B:
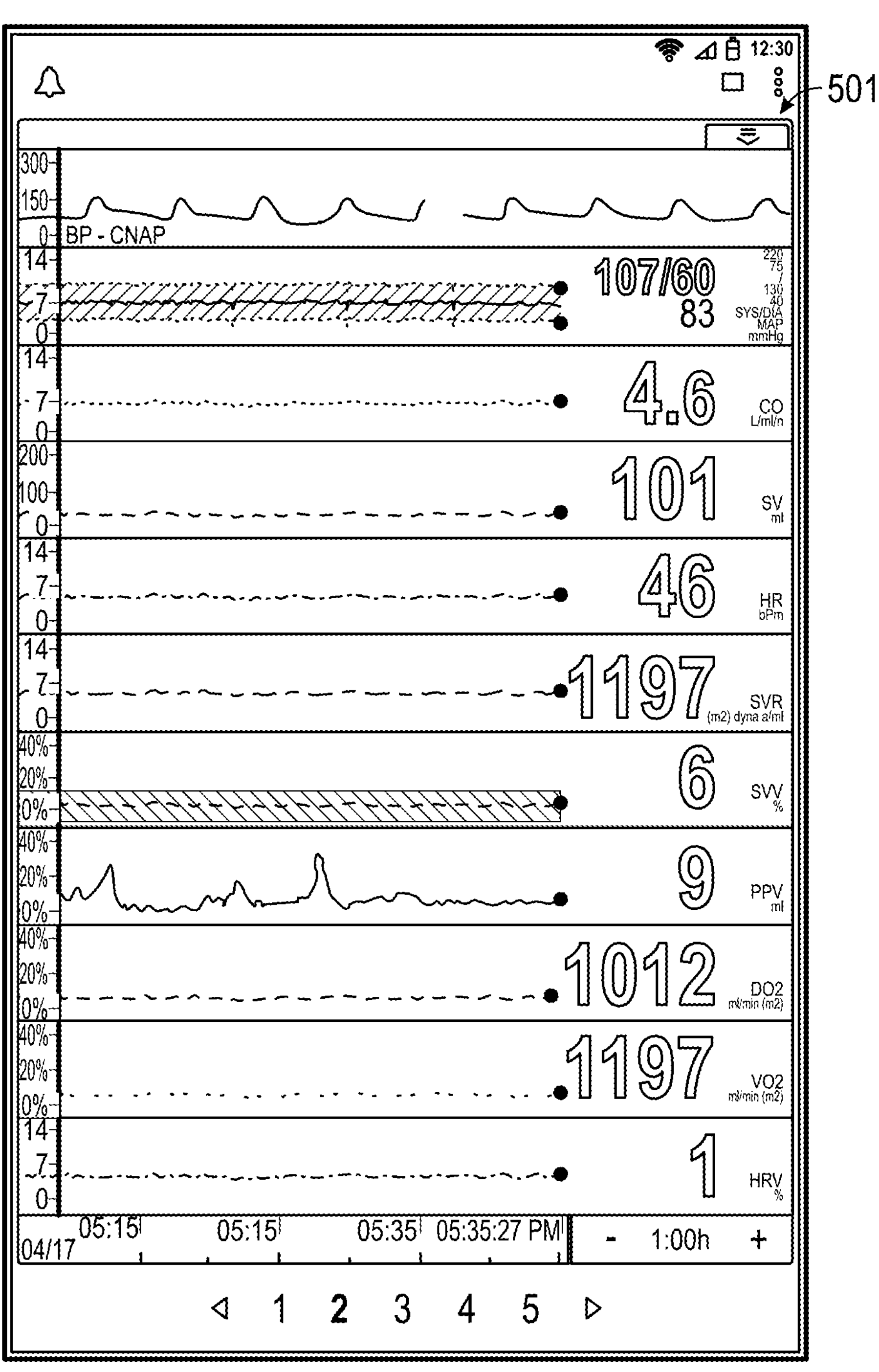

FIGS. 9A and 9B show example user interfaces that may display parameters or information relating to a patient's hemodynamic status and/or other physiological parameters or information. A user may select component 501 to navigate to a different user interface (such as shown in FIG. 9C) to select various physiological protocols.

Figure 9C:
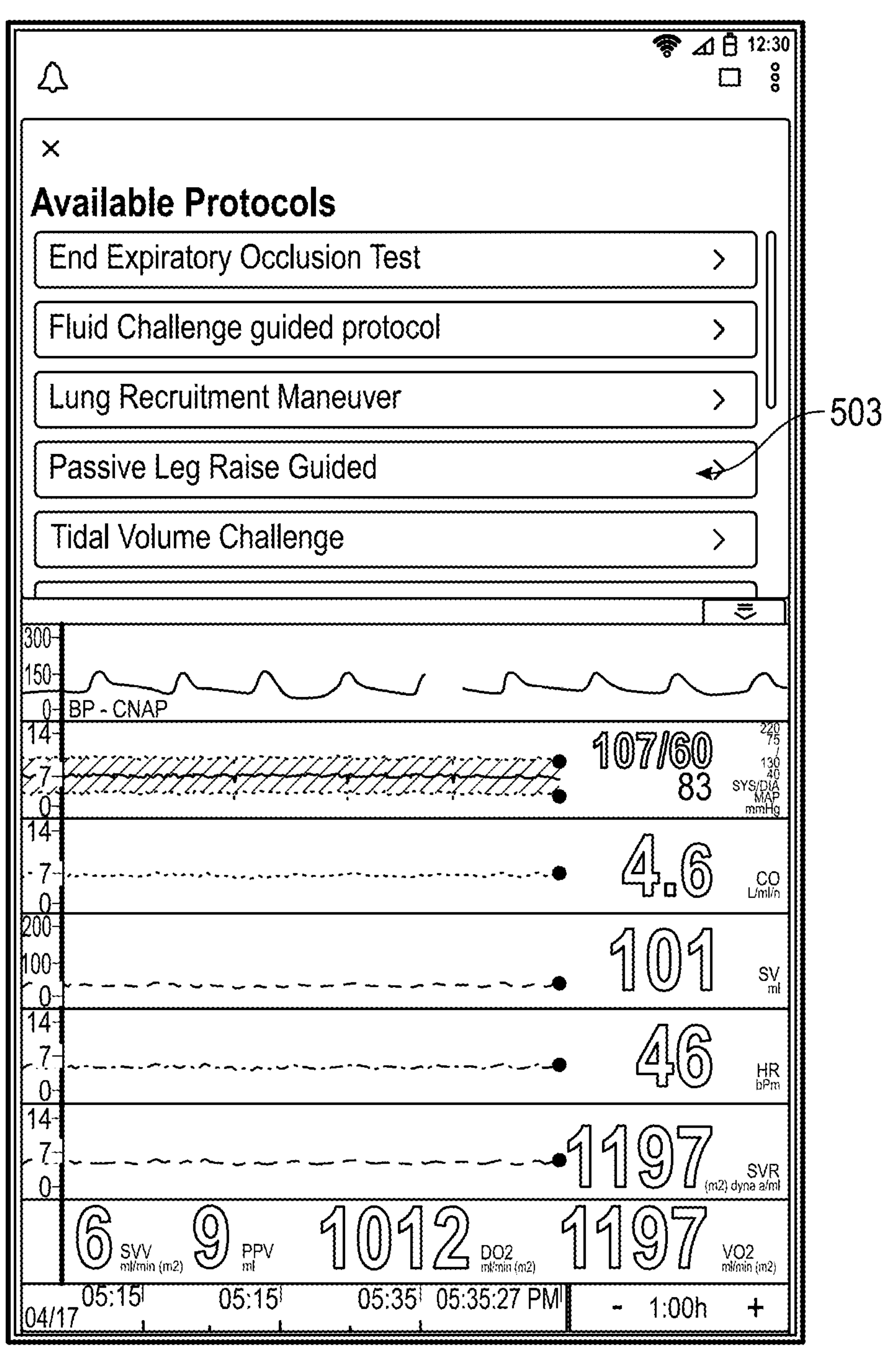

FIG. 9C shows an example user interface for selecting various physiological protocols. As shown the user interface may display a list of available protocols. In some embodiments, the user interface may display icons related to the protocols rather than a list. A user may select any of the displayed protocols to navigate to user interfaces relating to the selected protocol (for example, as shown and discussed with reference to FIGS. 10A-10D, 11A-11D, 12A-12C, 13A-13F). For example, a user may select component 503 to navigate to a "passive leg raise guided" protocol, as is shown and discussed with reference to FIGS. 9A-9G.

Figure 9D:
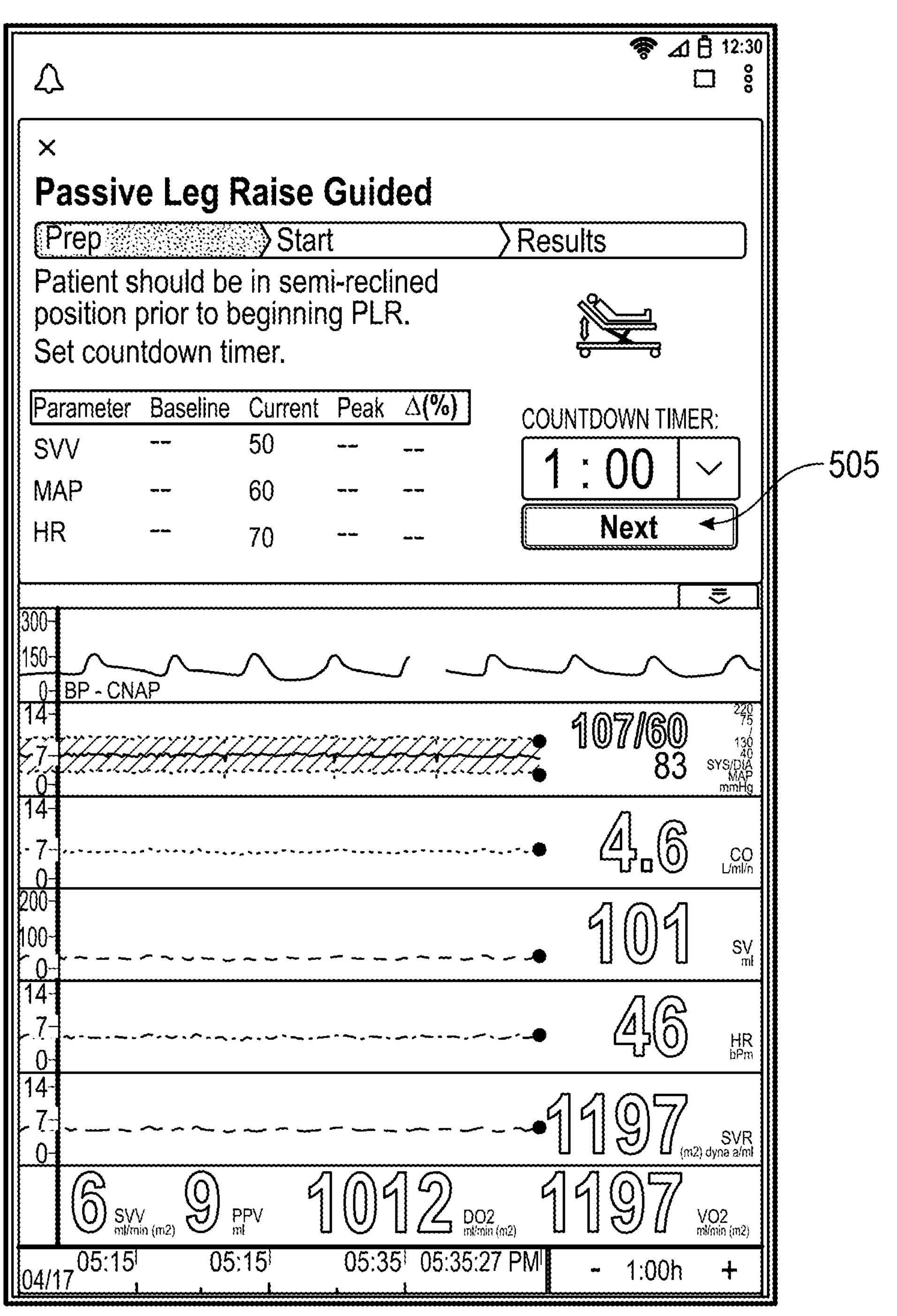
Figure 9E:
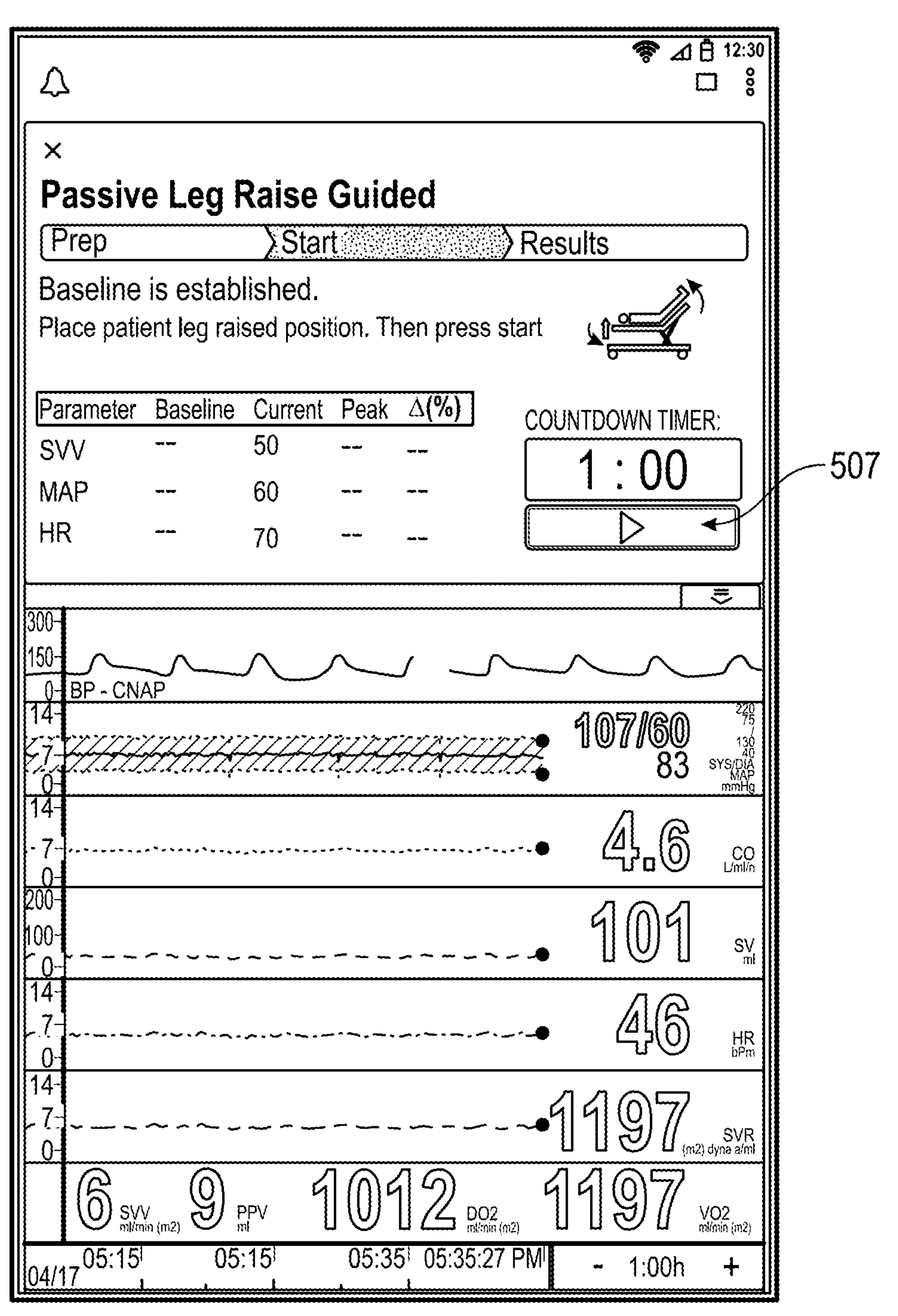
Figure 9F:
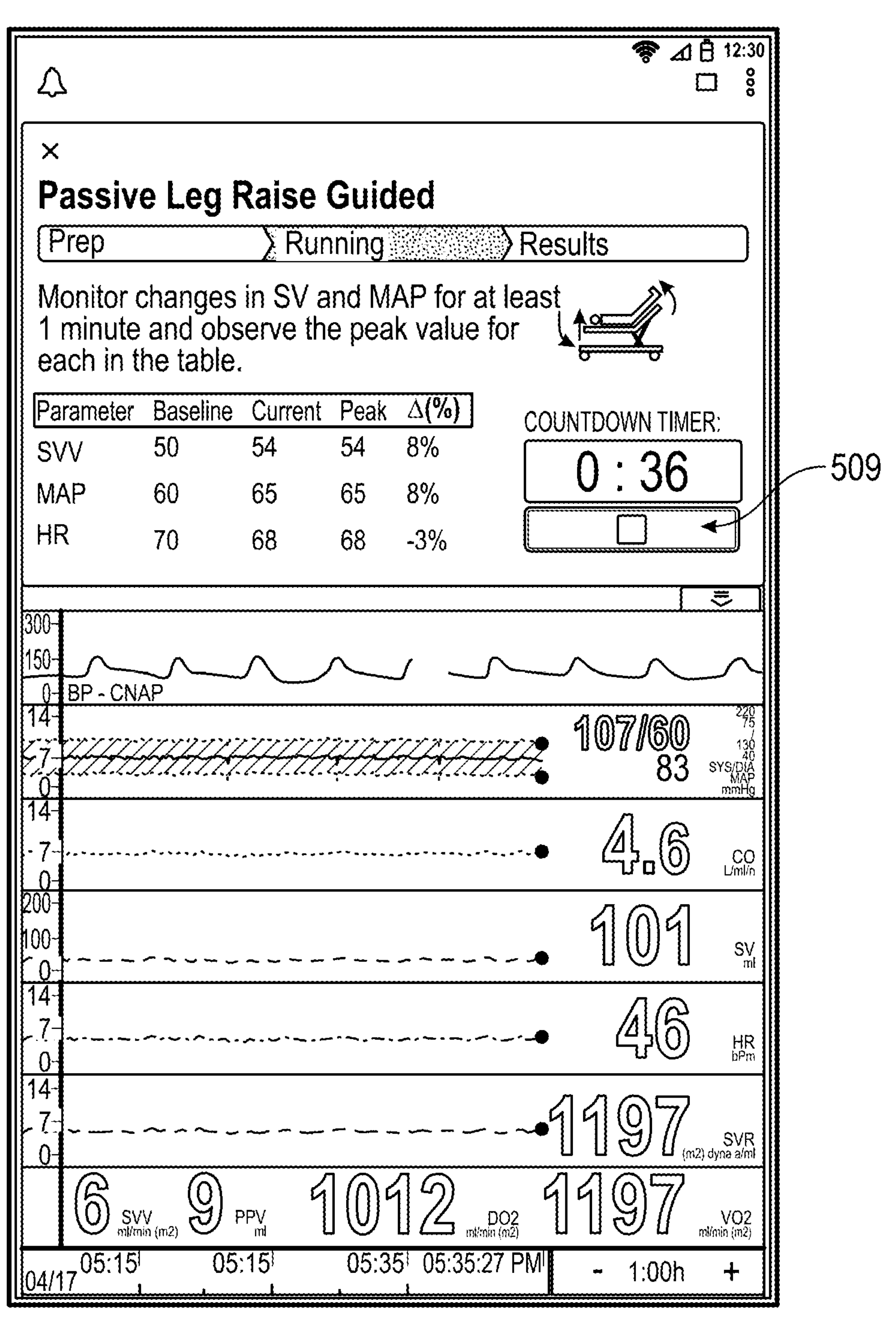
Figure 9G:
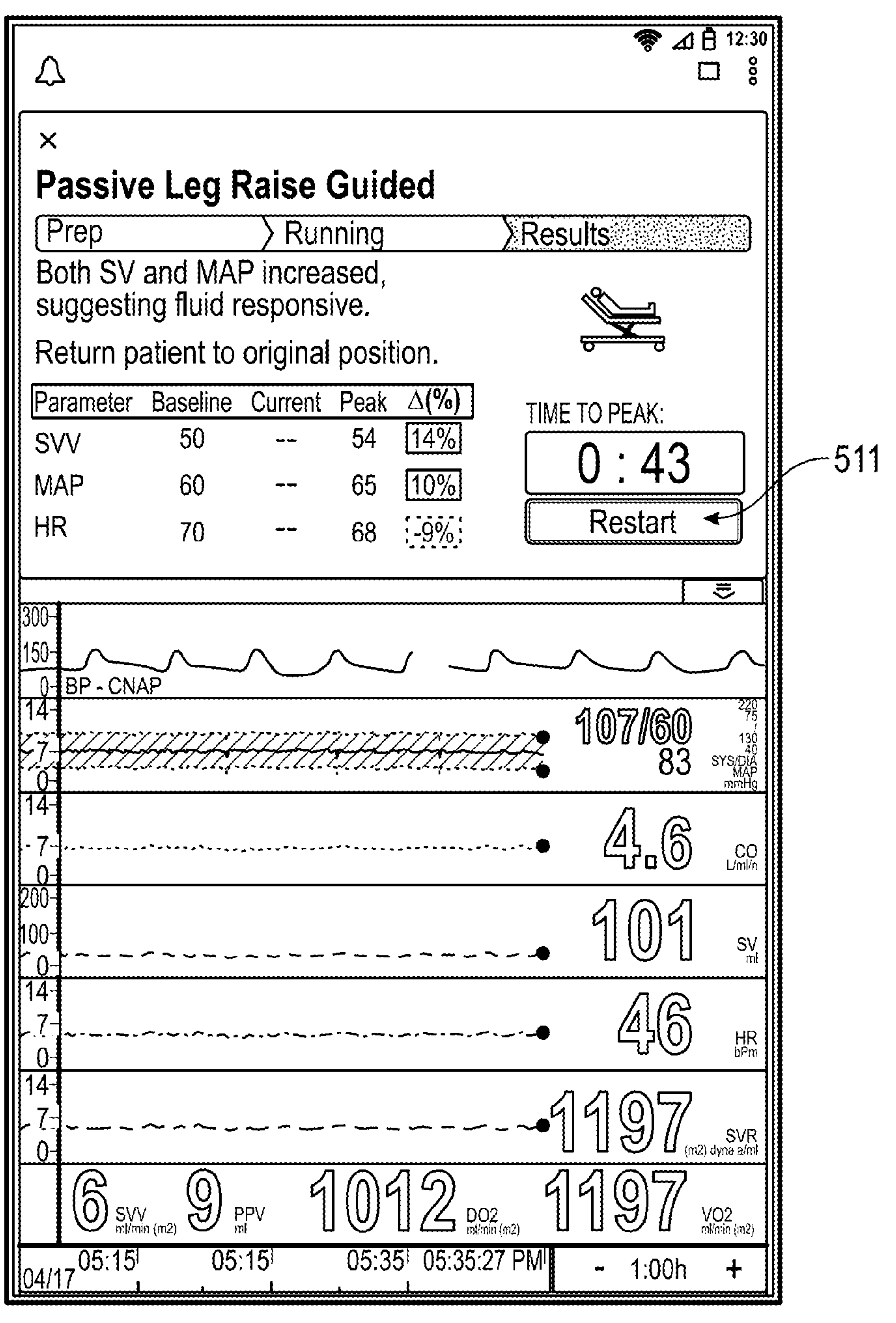

FIGS. 9D-9G show example user interfaces relating to a "passive leg raise guided" protocol. An example protocol may include systems and methods such as described with reference to U.S. patent application Ser. No. 16/673,335, entitled "SYSTEM TO MANAGE PATIENT HYDRATION" filed on Nov. 4, 2019, having a U.S. Patent Publication No. US 2020/0138368, the entirety of which is hereby incorporated by reference herein in its entirety. As shown in FIG. 9D, a user may select component 505 to navigate to the user interface shown in FIG. 9E. As shown in FIG. 9E, a user may select component 507 to initiate the protocol and which may navigate the user to the user interface shown in FIG. 9F. As shown in FIG. 9F, a user may select component 509 to stop or pause the protocol and/or restart a stopped or paused protocol. As shown in FIG. 9G, the user interface may display the results of the protocol which may include a patient's hemodynamic status during and/or after the protocol. A user may select component 511 to navigate to the user interface shown in FIG. 9D or 9E to have the option to restart the protocol.

FIGS. 10A-10D, 11A-11D, 12A-12C, 13A-13F show additional example user interfaces relating to additional example protocols which may be displayed as an overlay of the user interfaces of FIGS. 9A or 9B, as is shown with reference to the "passive leg raise guided" protocol user interfaces of FIGS. 9D-9G.

Figure 10A:
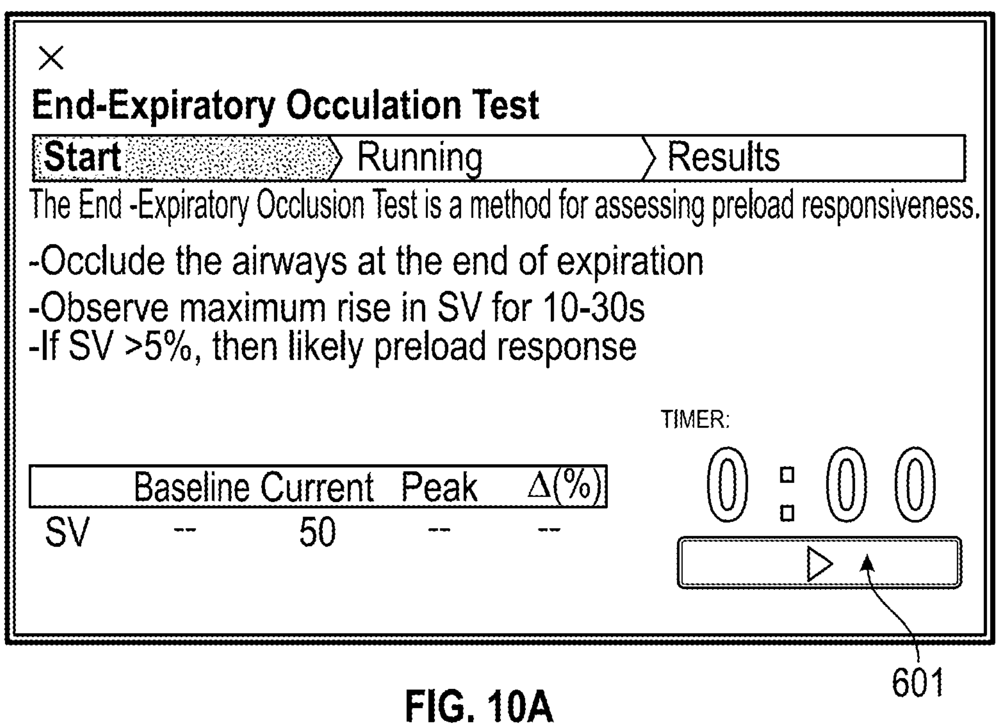
Figure 10B:
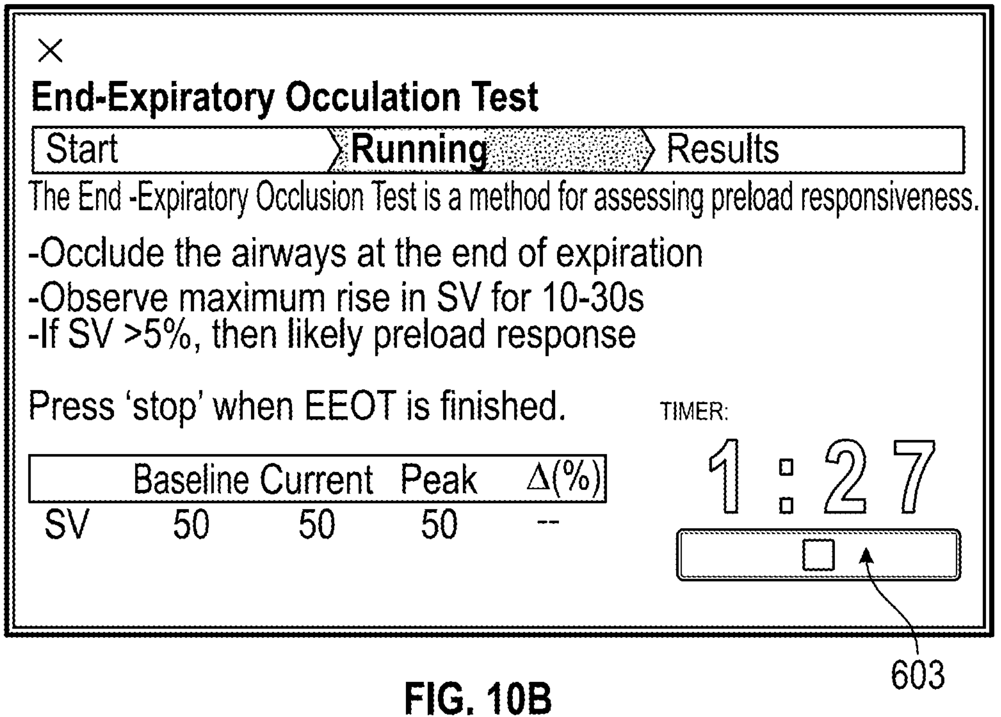
Figures 10C, 10D:
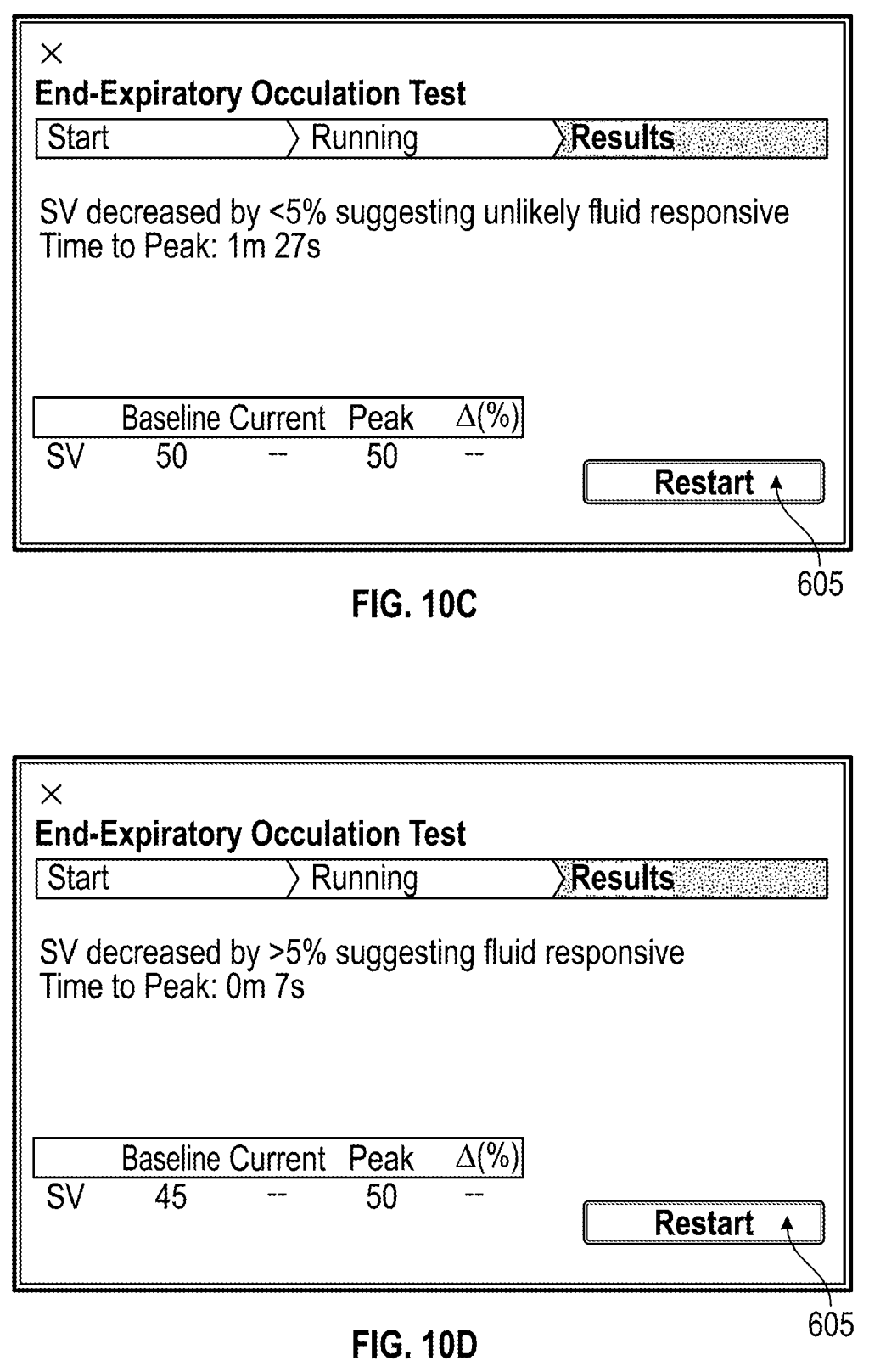

FIGS. 10A-10D show example user interfaces relating to a "end-expiratory occlusion test" protocol. A user may navigate to the user interface of FIG. 10A by selecting the corresponding protocol displayed in FIG. 9C, for example. As shown in FIG. 10A, a user may select component 601 to initiate the protocol and which may navigate the user to the user interface shown in FIG. 10B. As shown in FIG. 10B, a user may select component 603 to stop or pause the protocol and/or restart a stopped or paused protocol. As shown in FIG. 10C or 10D, the user interface may display the results of the protocol which may include a patient's hemodynamic status during and/or after the protocol. A user may select component 605 to navigate to the user interface shown in FIG. 10A to have the option to restart the protocol.

Figures 11A, 11B:
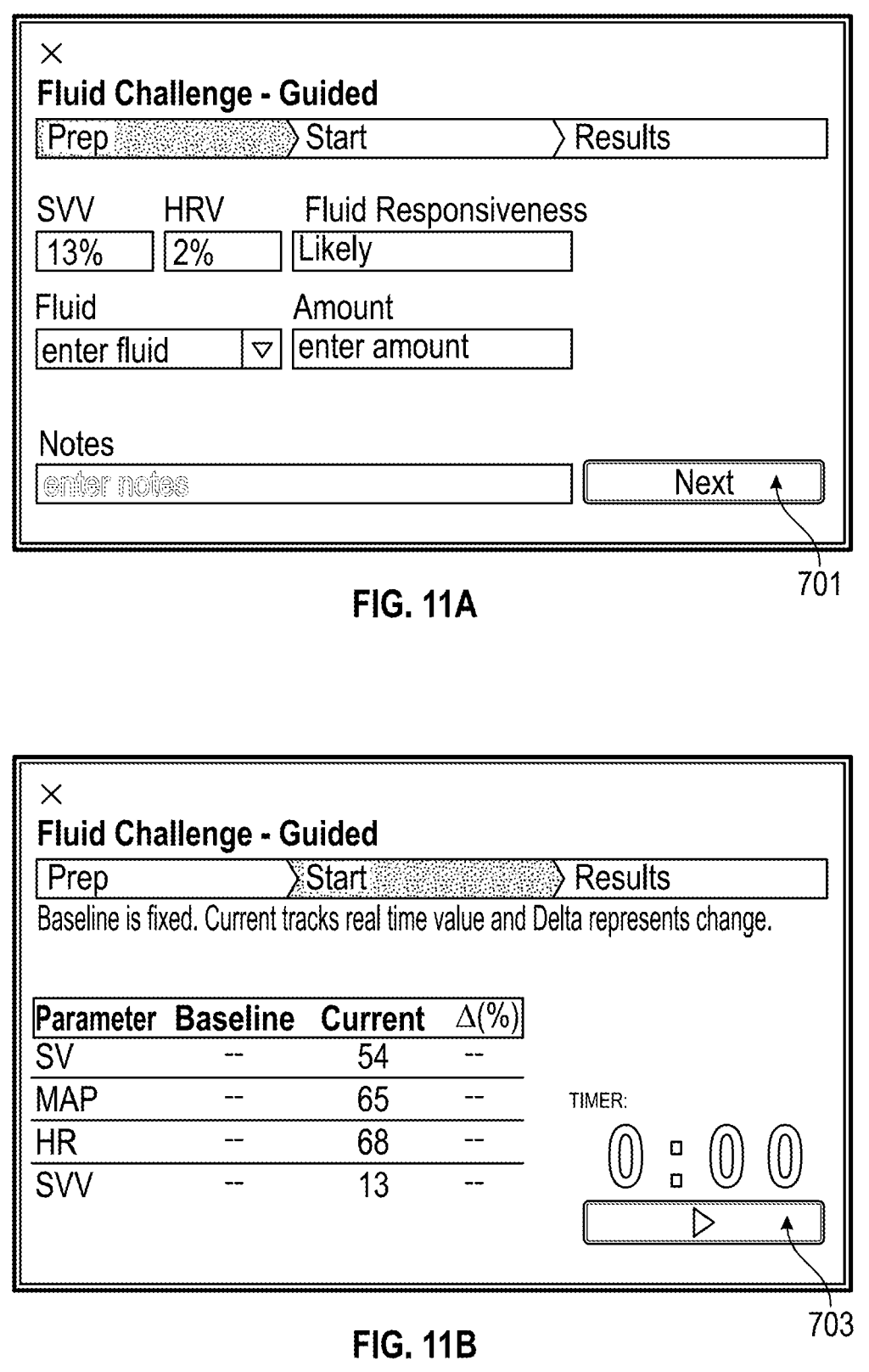
Figure 11C:
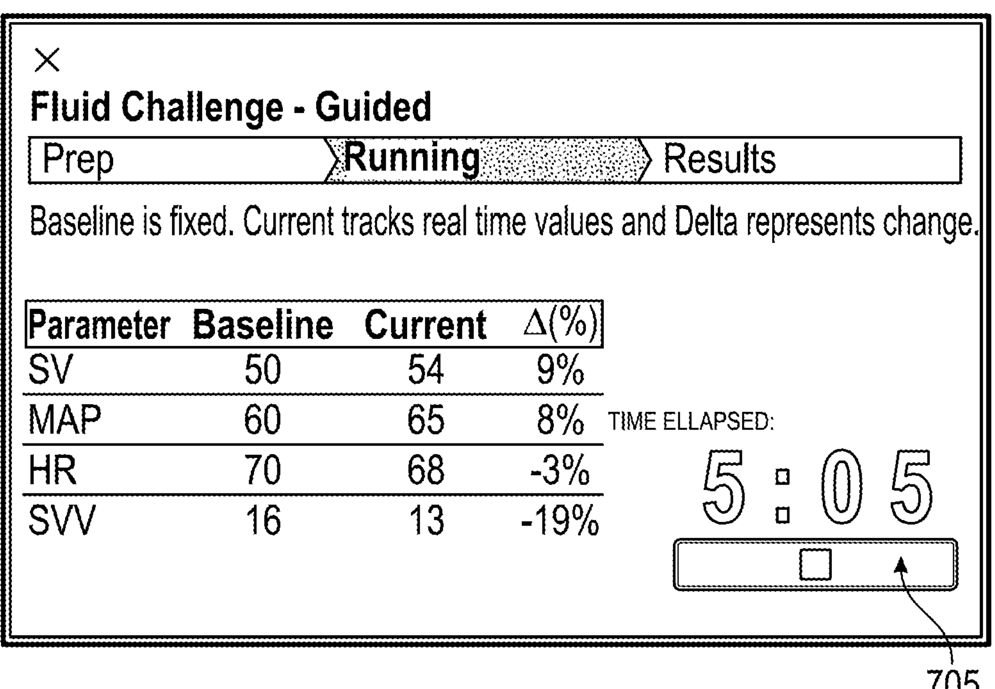
Figure 11D:
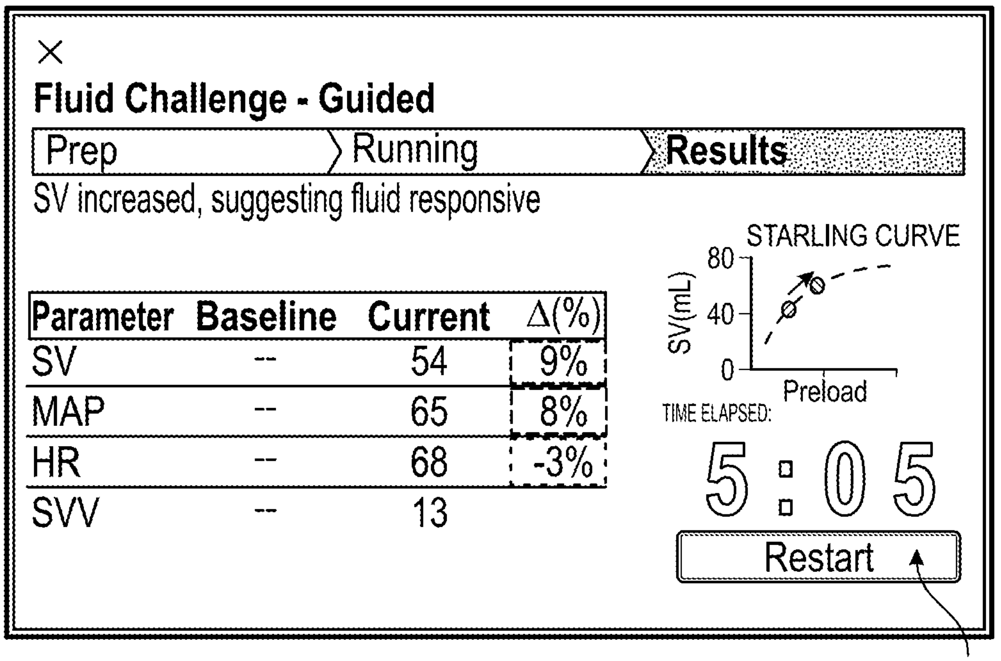

FIGS. 11A-11D show example user interfaces relating to a "fluid challenge-guided" protocol. A user may navigate to the user interface of FIG. 11A by selecting the corresponding protocol displayed in FIG. 9C, for example. As shown in FIG. 11A, a user may select component 701 to navigate to the user interface shown in FIG. 11B. As shown in FIG. 11B, a user may select component 703 to initiate the protocol and which may navigate the user to the user interface shown in FIG. 11C. As shown in FIG. 11C, a user may select component 705 to stop or pause the protocol and/or restart a stopped or paused protocol. As shown in FIG. 11D, the user interface may display the results of the protocol which may include a patient's hemodynamic status during and/or after the protocol. A user may select component 707 to navigate to the user interface shown in FIG. 11A or 11B to have the option to restart the protocol.

Figure 12A:
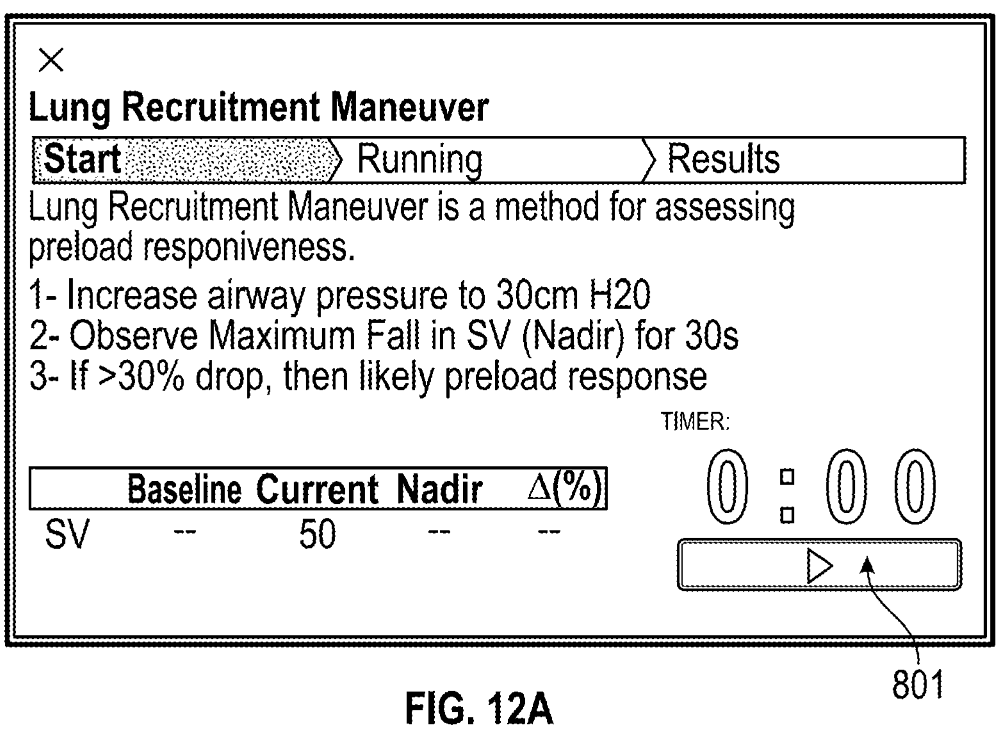
Figure 12B:
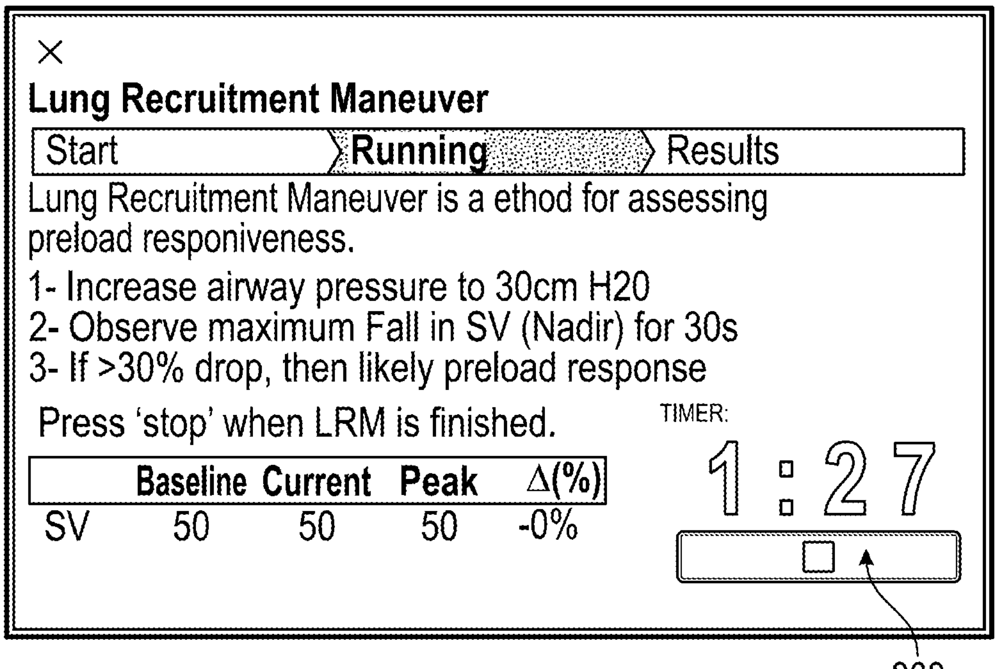
Figure 12C:
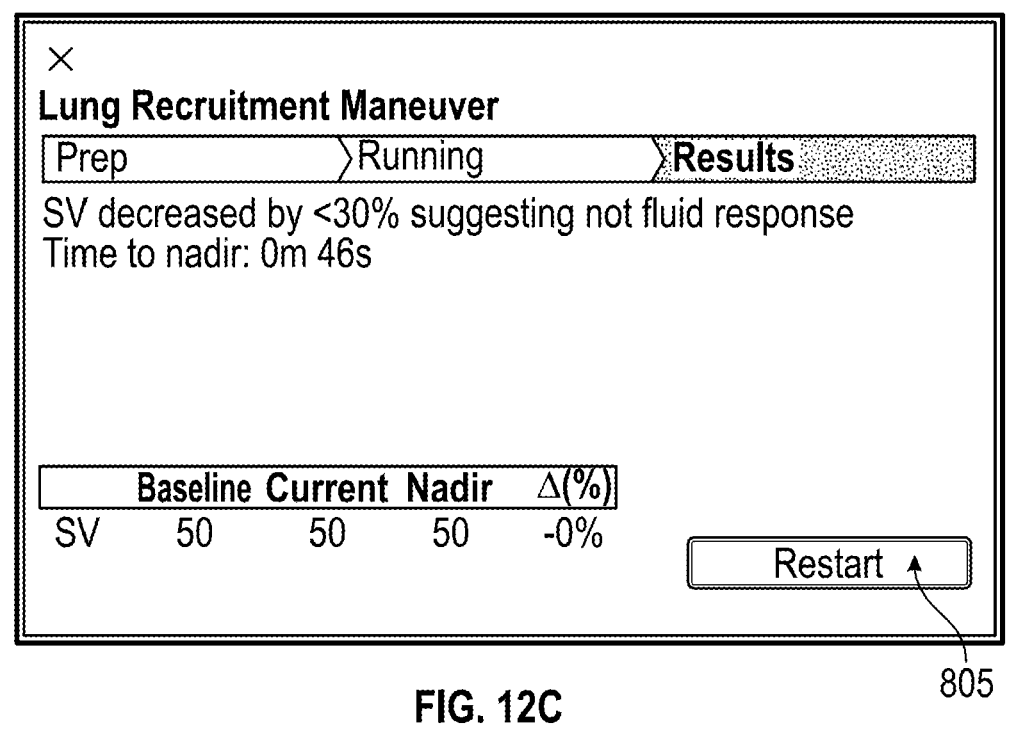

FIGS. 12A-12C show example user interfaces relating to a "lung recruitment maneuver" protocol. A user may navigate to the user interface of FIG. 12A by selecting the corresponding protocol displayed in FIG. 9C, for example. As shown in FIG. 12A, a user may select component 701 to initiate the protocol and which may navigate the user to the user interface shown in FIG. 12B. As shown in FIG. 12B, a user may select component 803 to stop or pause the protocol and/or restart a stopped or paused protocol. As shown in FIG. 12C, the user interface may display the results of the protocol which may include a patient's hemodynamic status during and/or after the protocol. A user may select component 805 to navigate to the user interface shown in FIG. 12A to have the option to restart the protocol.

Figures 13A, 13B:
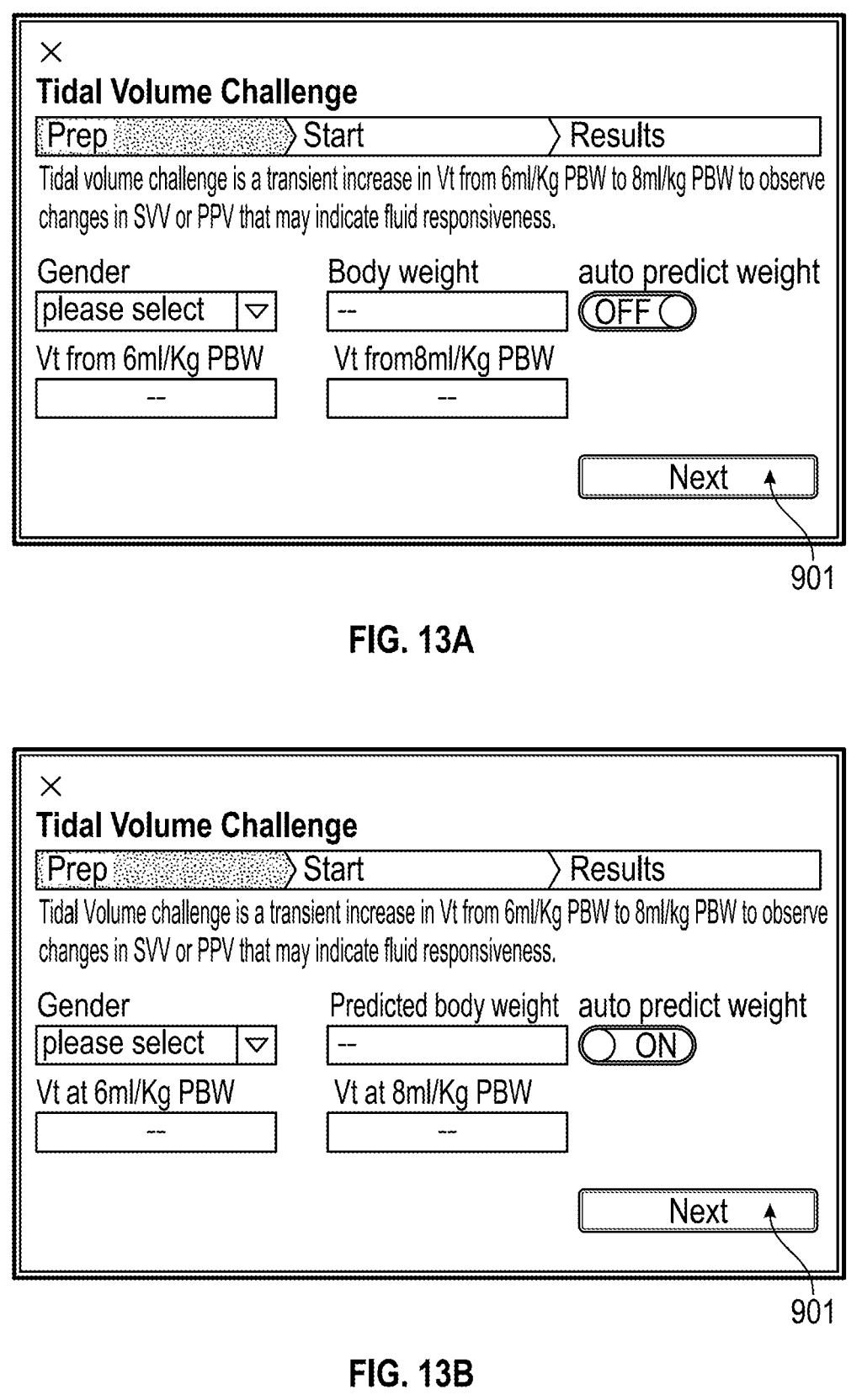
Figures 13C, 13D:
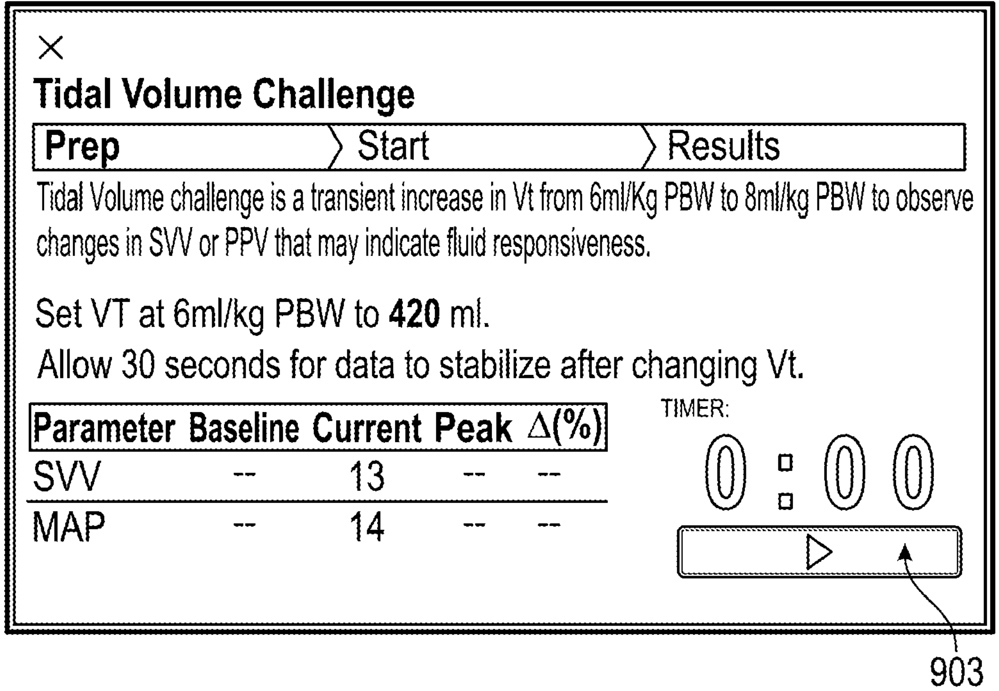
Figure 13E:
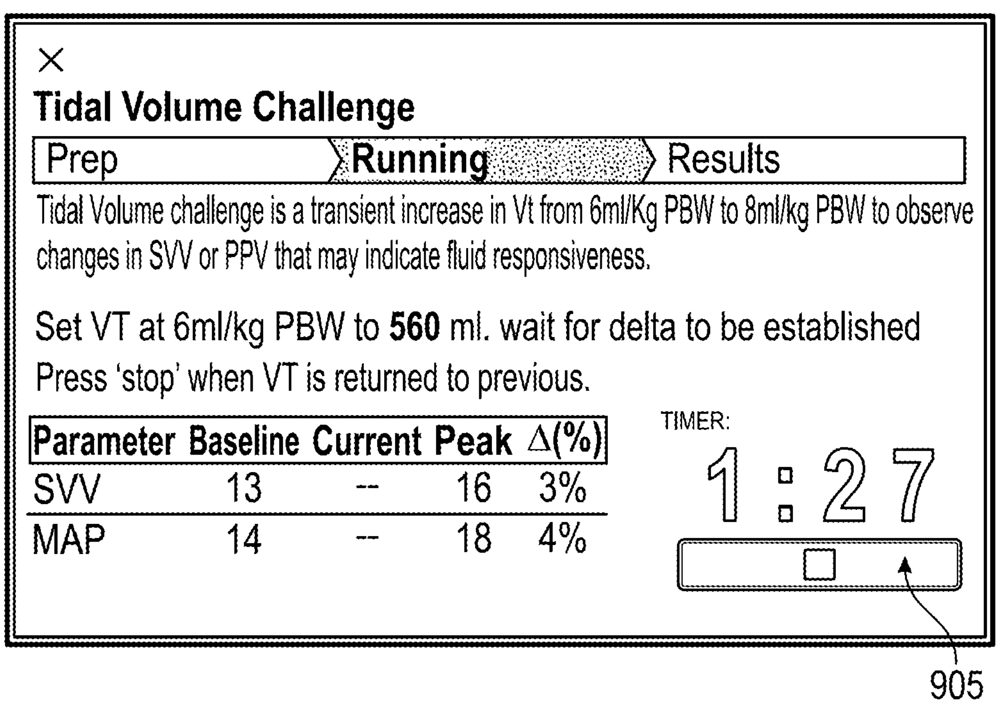
Figure 13F:
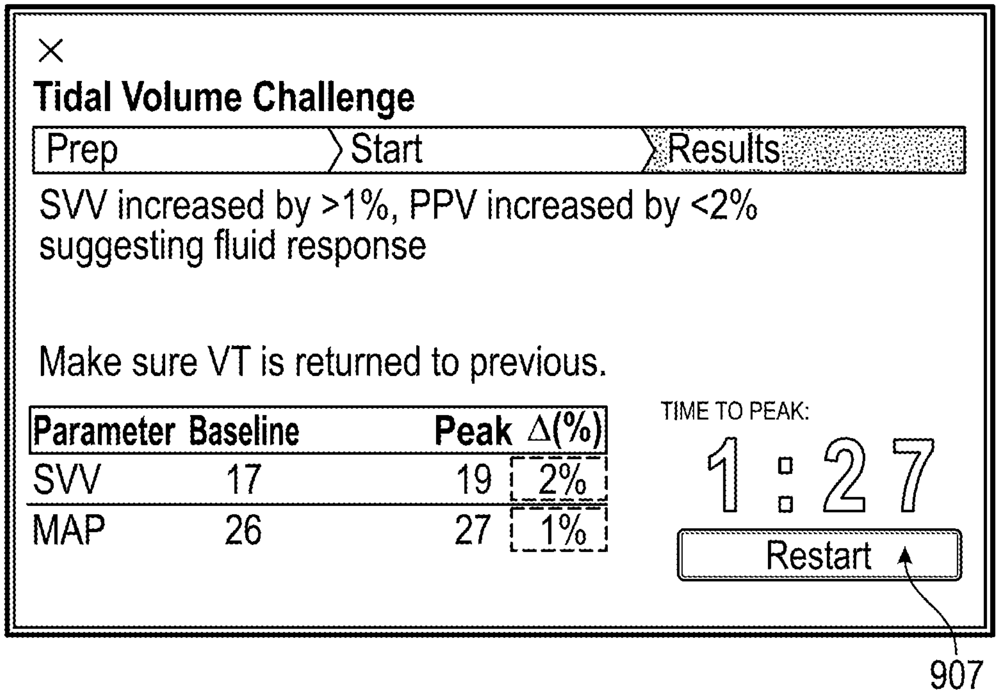

FIGS. 13A-13F show example user interfaces relating to a "tidal volume challenge" protocol. A user may navigate to the user interface of FIG. 13A or 13B or 13C by selecting the corresponding protocol displayed in FIG. 9C, for example. As shown in FIG. 13A or 13B a user may not be able to select component 901 to initiate the protocol. As shown in FIG. 13C, a user may be able to select component 901 to navigate to the user interface shown in FIG. 13D. As shown in FIG. 13D, a user may select component 903 to initiate the protocol and which may navigate the user to the user interface shown in FIG. 9E. As shown in FIG. 9E, a user may select component 905 to stop or pause the protocol and/or restart a stopped or paused protocol. As shown in FIG. 13F, the user interface may display the results of the protocol which may include a patient's hemodynamic status during and/or after the protocol. A user may select component 907 to navigate to one of the user interfaces shown in one of FIGS. 13A, 13B, 13C or 13D to have the option to restart the protocol.

Additional Considerations

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by one or more hardware processors, such as microprocessor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. Hardware processors can include electrical circuitry configured to process computer-executable instructions. In another embodiment, a hardware processor includes an FPGA or other programmable device that performs logic operations without processing computer-executable instructions. A hardware processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the hardware processor such that the hardware processor can read information from, and write information to, the storage medium. In the alternative, the storage medium can be integral to the hardware processor. The storage medium can be volatile or nonvolatile.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses, systems, and/or methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A system for displaying a physiological status of a patient, the system comprising:

a monitor comprising a display and configured to display graphical user interfaces via the display and receive user input via the display; and one or more hardware processors in communication with the display, the one or more hardware processors configured to:

generate one or more signals in response to a measurement of a physiological sensor;

process the one or more signals to generate one or more physiological parameters;

generate, based at least in part on the one or more signals or the one or more physiological parameters, user interface data for rendering a graphical user interface, wherein the graphical user interface comprises:

at least one first radial dial gauge associated with a first physiological parameter derived from a second physiological parameter of the one or more physiological parameters, the second physiological parameter having an influencing relationship with the first physiological parameter;

at least one second radial dial gauge displayed on a level below the first radial dial gauge, the second radial dial gauge associated with the second physiological parameter; and a branch displayed between the at least one first radial dial gauge and the at least one second radial dial gauge, the branch indicating the influencing relationship between the first physiological parameter and the second physiological parameter, the branch being displayed differently upon determining, based on the influencing relationship between the first and second physiological parameters, that an abnormal current value or trend of the first physiological parameter is caused by an abnormal value or trend of the second physiological parameter; and cause to display on the monitor, the user interface data, wherein the determining comprises evaluating trends of the first and second physiological parameters relative to a baseline value that is an average of all data above a confidence level over a determined time period prior to a trend period, and determining a trend direction based on a range.

2. The system of claim 1, wherein the physiological sensor comprises a transducer.

3. The system of claim 1, wherein the branch is emphasized based on an abnormal value of the second physiological parameter and an abnormal value of the first physiological parameter.

4. The system of claim 3, wherein an emphasis of the branch comprises a change to a highlighting or coloring of the branch.

5. The system of claim 1 wherein the branch is emphasized based at least in part on an abnormal trend of the second physiological parameter or an abnormal trend of the first physiological parameter.

6. The system of claim 1 wherein the at least one first radial dial gauge comprises at least one radial dial gauge segment, wherein each segment is associated with a range of physiological parameter values.

7. The system of claim 6, wherein a first range associated with a first segment comprises a normal range and a second range associated with a second segment comprises an abnormal range.

8. The system of claim 1, wherein the at least one first radial dial gauge comprises a dial configured to indicate a current value of the first physiological parameter.

9. The system of claim 1, wherein the first physiological parameter comprises a blood pressure parameter and wherein the second physiological parameter comprises cardiac index (CI) or system vascular resistance index (SVRI).

10. The system of claim 1, wherein the first physiological parameter comprises cardiac index (CI) and wherein the second physiological parameter comprises stroke volume index (SVI) or heart rate (HR).

11. The system of claim 1, wherein first physiological parameter comprises stroke volume index (SVI) and the second physiological parameter comprises pulse pressure variation (PPV).

12. The system of claim 1, wherein the at least one first radial dial gauge comprises at least one textual and at least one graphical representation of a current value of the first physiological parameter.

13. The system of claim 12, wherein the at least one first radial dial gauge comprises a graphical indication of a current trend associated with the first physiological parameter.

14. The system of claim 12, wherein the first physiological parameter is based on a function of at least the second physiological parameter.

15. The system of claim 14, wherein the first physiological parameter is determined based on the second physiological parameter.

16. The system of claim 15, wherein the second physiological parameter is determined based on a third physiological parameter.

17. A system for displaying a physiological status of a patient, the system comprising:

a monitor comprising a display and configured to display graphical user interfaces via the display and receive user input via the display; and one or more hardware processors in communication with the display, the one or more hardware processors configured to:

generate one or more signals in response to a measurement of a physiological sensor;

process the one or more signals to generate one or more physiological parameters;

generate, based at least in part on the one or more signals or the one or more physiological parameters, user interface data for rendering a graphical user interface, wherein the graphical user interface comprises:

a tree diagram of graphical representations of a plurality of physiological parameters, wherein a location of a graphical representation of a physiological parameter of the plurality of physiological parameters is associated with an influencing relationship of the physiological parameter with a primary physiological parameter, wherein branches of the tree diagram are emphasized upon determining, based on the influencing relationship, that a current value or trend of a primary physiological parameter of the plurality of physiological parameters is abnormal and that the abnormal current value or trend of the primary physiological parameter is caused by an abnormal current value or trend of an influencing one-physiological parameter of the plurality of physiological parameters; and cause to display on the monitor, the user interface data, wherein the determining comprises evaluating trends of the primary and influencing physiological parameters relative to a baseline value that is an average of all data above a confidence level over a determined time period prior to a trend period, and determining a trend direction based on a range.

18. The system of claim 17, wherein a branch between a primary physiological parameter of the plurality of physiological parameters and an influencing physiological parameter of the plurality of physiological parameters is emphasized if the current value of both the primary physiological parameter and the influencing physiological parameter are outside respective normal ranges.

19. The system of claim 18, wherein the primary physiological parameter comprises a blood pressure parameter and the influencing physiological parameter comprises cardiac index (CI) or system vascular resistance index (SVRI).

20. The system of claim 18, wherein the primary physiological parameter comprises CI and wherein the influencing physiological parameter comprises stroke volume index (SVI) or heart rate (HR).

21. The system of claim 18, wherein the primary physiological parameter comprises SVI and the influencing physiological parameter comprises pulse pressure variation (PPV).

22. The system of claim 17, wherein at least one graphical representation of a physiological parameter comprises a radial gauge.

* * * * *